United States Patent
McNamara et al.

(10) Patent No.: US 10,619,219 B2
(45) Date of Patent: Apr. 14, 2020

(54) OLIGONUCLEOTIDE-BASED PROBES AND METHODS FOR DETECTION OF MICROBES

(71) Applicant: UNIVERSITY OF IOWA RESEARCH FOUNDATION, Iowa City, IA (US)

(72) Inventors: James O. McNamara, Iowa City, IA (US); Katie R. Flenker, Iowa City, IA (US); Hyeon Kim, Iowa City, IA (US); Alexander R. Horswill, Iowa City, IA (US); Frank J. Hernandez, Iowa City, IA (US); Mark Behlke, Coralville, IA (US); Lingyan Huang, Coralville, IA (US); Richard Owczarzy, Coralville, IA (US); Elliot Burghardt, Iowa City, IA (US); Karen Clark, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 256 days.

(21) Appl. No.: 15/117,414

(22) PCT Filed: Feb. 9, 2015

(86) PCT No.: PCT/US2015/015062
§ 371 (c)(1),
(2) Date: Aug. 8, 2016

(87) PCT Pub. No.: WO2015/120406
PCT Pub. Date: Aug. 13, 2015

(65) Prior Publication Data
US 2016/0340717 A1    Nov. 24, 2016

Related U.S. Application Data

(60) Provisional application No. 61/937,359, filed on Feb. 7, 2014, provisional application No. 61/980,498, filed on Apr. 16, 2014, provisional application No. 61/992,034, filed on May 12, 2014.

(51) Int. Cl.
| | | |
|---|---|---|
| C12Q 1/68 | (2018.01) | |
| C12Q 1/689 | (2018.01) | |
| C07H 21/00 | (2006.01) | |
| C07H 21/02 | (2006.01) | |
| C07H 21/04 | (2006.01) | |
| A61K 49/00 | (2006.01) | |
| C12Q 1/70 | (2006.01) | |
| G01N 21/64 | (2006.01) | |
| G01N 33/58 | (2006.01) | |

(52) U.S. Cl.
CPC .......... *C12Q 1/689* (2013.01); *A61K 49/0054* (2013.01); *C07H 21/02* (2013.01); *C07H 21/04* (2013.01); *C12Q 1/701* (2013.01); *G01N 21/6428* (2013.01); *G01N 33/581* (2013.01); *G01N 2021/6432* (2013.01)

(58) Field of Classification Search
CPC .......... G01N 33/50; C12Q 1/68; C07H 21/00
See application file for complete search history.

(56) References Cited

U.S. PATENT DOCUMENTS

| | | | |
|---|---|---|---|
| 6,773,885 B1 | 8/2004 | Walder et al. | |
| 7,041,807 B1* | 5/2006 | Cashman | C07K 16/18 424/130.1 |
| 7,439,341 B2 | 10/2008 | Laikhter et al. | |
| 7,803,536 B2 | 9/2010 | Behlke et al. | |
| 2005/0026284 A1* | 2/2005 | Kudlicki | C07K 16/40 435/455 |
| 2006/0088833 A1* | 4/2006 | Bange | C12Q 1/689 435/6.15 |
| 2007/0238957 A1* | 10/2007 | Yared | A61B 5/0059 600/407 |
| 2010/0221717 A1* | 9/2010 | Chen | C12Q 1/6858 435/6.14 |
| 2010/0323348 A1 | 12/2010 | Hamady et al. | |
| 2011/0003290 A1* | 1/2011 | Gale | C12Q 1/6827 435/6.12 |
| 2012/0329160 A1* | 12/2012 | Hong | C07K 14/39 435/471 |

FOREIGN PATENT DOCUMENTS

| | | |
|---|---|---|
| EP | 2669663 A1 | 12/2013 |
| WO | 2001021830 A1 | 3/2001 |
| WO | 2011133433 A2 | 10/2011 |
| WO | 2013033436 A1 | 3/2013 |
| WO | 2013048583 A2 | 4/2013 |

OTHER PUBLICATIONS

Brakstad et al., APMIS 103:219 (Year: 1995).*
Lachica et al., Applied Microbiology 21 (4) ::585 (Year: 1971).*
Lagacé-Wiens et al., J. of Clinical Microbiology 45(10) :3478 (Year: 2007).*
Madison et al., J. of Clinical Microbiology 18(3) :722 (Year: 1983).*
Micrococcal Nuclease Thermo Sientific (Year: 2013).*
Ratner et al., J. of Clinical Microbiology 21(6) : 722 (Year: 1985).*
Rosman, et al., "Ex Vivo Tracer Efficacy in Optical Imaging of *Staphylococcus aureus* Nuclease Activity", Scientific Reports 8, 1305, 8 pages (2018).
Taylor, et al., "*E. coli* host strains significantly affect the quality of small scale plasmid DNA preparations used for sequencing", Nucleic Acids Res. 21(7): 1677-1678 (1993).

(Continued)

*Primary Examiner* — Ethan C Whisenant
(74) *Attorney, Agent, or Firm* — Viksnins Harris Padys Malen LLP

(57) ABSTRACT

The present invention relates to a rapid detection of microbial-associated nuclease activity with chemically modified nuclease (e.g., endonuclease) substrates, and probes and compositions useful in detection assays.

26 Claims, 42 Drawing Sheets

Specification includes a Sequence Listing.

(56) References Cited

OTHER PUBLICATIONS

Tiet, et al., "Colorimetric Detection of *Staphylococcus aureus* Contaminated Solutions without Purification", Bioconjugate Chem 28(1), 183-193 (2017).
Van Hal, et al., "Predictors of mortality in *Staphylococcus aureus* Bacteremia.", Clin Microbiol Rev. vol. 25(2) p. 362-386 (2012).
Wannamaker, et al., "Streptococcal nucleases. II. Characterization of DNAse D", J Exp Med 126(3), 497-508 (1967).
Weissleder, et al., "In vivo imaging of tumors with protease-activated near-infrared fluorescent probes.", Nat Biotechnol. vol. 17(4) p. 375-378 (1999).
Weissleder, et al., "Shedding light onto live molecular targets", Nat Med. vol. 9(1), 123-128 (2003).
Wilson, et al., "Laboratory diagnosis of urinary tract infections in adult patients.", Clin Infect Dis. vol. 38(8) p. 1150-1158 (2004).
Xiong, et al., "Real-time in vivo bioluminescent imaging for evaluating the efficacy of antibiotics in a rat *Staphylococcus aureus* endocarditis model.", Antimicrob Agents Chemother. vol. 49(1) p. 380-387 (2005).
Asahara, "Purification and characterization of *Escherichia coli* endonuclease III from the cloned nth gene.", Biochemistry. vol. 28, No. (10) p. 4444-4449 (1989).
Baba, et al., "Construction of *Escherichia coli* K-12 in-frame, single-gene knockout mutants: the Keio collection", Mol Syst Biol. vol. 2: 2006.0008. (2006).
Baba, et al., "Genome sequence of *Staphylococcus aureus* strain Newman and comparative analysis of staphylococcal genomes: polymorphism and evolution of two major pathogenicity islands.", J Bacteriol. vol. 190(1) p. 300-310 (2008).
Beenken, et al., "Epistatic relationships between sarA and agr in *Staphylococcus aureus* biofilm formation.", PLoS One. vol. 5(5) e10790 (2010).
Behlke, "Chemical modification of siRNAs for in vivo use", Oligonucleotides 18, 305-319 (2008).
Borsa, et al., "*Staphylococcus aureus* detection in blood samples by silica nanoparticle-oligonucleotides conjugates", Biosens Bioelectron 86, 27-32 (2016).
Burghardt, et al., "Rapid, Culture-Free Detection of *Staphylococcus aureus* Bacteremia", PLoS One 11(6), e0157234 (2016).
Choppa, et al., "Multiplex PCR for the detection of Mycoplasma fermentans, M. hominis and M. penetrans in cell cultures and blood samples of patients with chronic fatigue syndrome.", Mol Cell Probes. vol. 12(5) p. 301-308 (1998).
Connelly, et al., "Biosensors for the detection of waterborne pathogens.", Anal Bioanal Chem. vol. 402(1), 117-127 (2012).
Cuatrecasas, et al., "Catalytic properties and specificity of the extracellular nuclease of *Staphylococcus aureus*.", J Biol Chem. vol. 242(7) p. 1541-1547 (1967).
Dickey, et al., "Rapid and Sensitive Detection of Circulating Tumor Cells with Nuclease-Activated Oligonucleotide Probes", 18th Annual Meeting of the American-Society-of-Gene-and-Cell-Therapy (ASGCT), New Orleans, LA, May 13-16, 2015, published in Molecular Therapy, 23, pp. S28-S28, Supp: 1, Meeting Abstract: 63, Published: May 2015.
Ferrieri, et al., "Biochemical and immunological characterization of the extracellular nucleases of group B streptococci", J Exp Med 151(1), 56-68 (1980).
Ferrieri, et al., "Production of bacteremia and meningitis in infant rats with group B streptococcal serotypes", Infect Immun 27(3), 1023-1032 (1980).
Flenker, et al., "Rapid Detection of Urinary Tract Infections via Bacterial Nuclease Activity", Molecular Therapy 25 (6), 1353-1362 (2017).
Foxman, et al., "Epidemiology of urinary tract infections: incidence, morbidity, and economic costs.", Am J Med. vol. 113 Suppl 1A p. 5S-13S (2002).
Foxman, "The epidemiology of urinary tract infection.", Nat Rev Urol. vol. 7(12) p. 653-660 (2010).
Giangrande, et al., "Nuclease-activated oligonucleotide probes for detection of breast cancer circulating tumor cells (CTCs): Early clinical results", Early clinical results [abstract]. In: Proceedings of the 2016 San Antonio Breast Cancer Symposium; San Antonio, TX. Philadelphia (PA), Dec. 6-10, 2016: AACR; Cancer Res 2017;77(4 Suppl):Abstract nr P1-01-14.
Gillaspy, et al., "Role of the accessory gene regulator (agr) in pathogenesis of staphylococcal osteomyelitis.", Infect Immun. vol. 63(9) p. 3373-3380 (1995).
Green, et al., "Nuclease-resistant nucleic acid ligands to vascular permeability factor/vascular endothelial growth factor", Chem Biol 2(10), 683-695 (1995).
Guo, et al., "nfi, the gene for endonuclease V in *Escherichia coli* K-12.", J Bacteriol. vol. 179, No.(2) p. 310-316 (1997).
Heilbronner, et al., "Genome sequence of *Staphylococcus lugdunensis* N920143 allows identification of putative colonization and virulence factors.", FEMS Microbiol Lett. vol. 322(1) p. 60-67 (2011).
Hernandez, et al., "Degradation of nuclease-stabilized RNA oligonucleotides in Mycoplasma-contaminated cell culture media", Nucleic Acid Ther 22, 58-68 (2012).
Hernandez, et al., "NanoKeepers: stimuli responsive nanocapsules for programmed specific targeting and drug delivery", Chemical Communications 50(67), 9489-9492 (2014).
Hernandez, et al., "Noninvasive imaging of *Staphylococcus aureus* infections with a nuclease-activated probe.", Nat Med. vol. 20(3) p. 301-306 (2014).
Hernandez, et al., "Nuclease activity as a specific biomarker for breast cancer", Chem Commun 52(83), 12346-12349 (2016).
Hernandez, et al., "Optical imaging of *S. aureus* infections with a quenched fluorescent oligonucleotide probe", Abstract presented in Boston, MA at the Annual Meeting of the Oligonucleotide-Therapeutics-Society on Oct. 28-31, 2012.
Hernandez, et al., "Optical imaging of *S. aureus* infections with a quenched fluorescent oligonucleotide probe", Presented Oct. 28-31, 2012 in Boston, MA at the Annual Meeting of the Oligonucleotide-Therapeutics-Society.
Kaper, et al., "Pathogenic *Escherichia coli*.", Nat Rev Microbiol. vol. 2(2) p. 123-140 (2004).
Kelemen, et al., "Hypersensitive substrate for ribonucleases.", Nucleic Acids Res. vol. 27(18) p. 3696-3701 (1999).
Kiedrowski, et al., "Nuclease modulates biofilm formation in community-associated methicillin-resistant *Staphylococcus aureus*.", PLoS One. vol. 6(11) e26714 (2011).
Kiedrowski, et al., "*Staphylococcus aureus* Nuc2 is a Functional, Surface-Attached Extracellular Nuclease", PLOS One vol. 9 (4), E95574, 13 pages (2014).
Klevens, et al., "Invasive methicillin-resistant *Staphylococcus aureus* infections in the United States.", JAMA. vol. 298(15) p. 1763-1771 (2007).
Lau, et al., "Identification of Klebsiella pneumoniae genes uniquely expressed in a strain virulent using a murine model of bacterial pneumonia.", Microb Pathog. vol. 42(4) p. 148-155 (2007).
Lehman, et al., "The deoxyribonucleases of *Escherichia coli*. II. Purification and properties of a ribonucleic acid-inhibitable endonuclease.", J Biol Chem. vol. 237 p. 819-828 (1962).
McNamara, et al., "Degradation of Nuclease-Stabilized RNA Oligonucleotides in a Cell Culture Contaminated with Mycoplasma", 7th Annual Meeting of the Oligonucleotide-Therapeutics-Society, Abstract, Copenhagen, Denmark, Sep. 8-10, 2011.
McNamara, et al., "Degradation of Nuclease-Stabilized RNA Oligonucleotides in a Cell Culture Contaminated with Mycoplasma", Presented Sep. 8-10, 2011, in Copenhagen, Denmark, at the 7th Annual Meeting of the Oligonucleotide-Therapeutics-Society.
McNamara, "Non-invasive Imaging of *S. aureus* Infections with a Nuclease-Activated Probe", Seminar at the 7th Edition of Nosocomial Infection Day, Lyon France, presented via Skype, Dec. 10, 2015.
McNamara, "Nuclease-activated probes for rapid, target-specific detection of bacterial pathogens", Presentation at Biological and Chemical Sensors Summit, 2016, La Jolla, CA, Dec. 6, 2016.
McNamara, "Nuclease-activated probes for rapid, target-specific detection of bacterial pathogens", Presentation at the Biodefense World Summit in Alexandria, VA. on Jun. 26-29, 2017.

(56) References Cited

OTHER PUBLICATIONS

McNamara, et al., "Optical imaging of *S. aureus* infections with a quenched fluorescent oligonucleotide probe", Presention at RNAIowa meeting on campus on Oct. 25, 2012.

McNamara, "Rapid Nuclease-Based Assays for Infectious Diseases", Presented at the GTCBio Conference 7th Non-Coding RNA & RNAi Therapeutics Conference in Boston, MA on Sep. 14-15, 2016.

Moon, et al., "Structural insights into catalytic and substrate binding mechanisms of the strategic EndA nuclease from *Streptococcus pneumoniae*.", Nucleic Acids Res. vol. 39(7) p. 2943-2953 (2011).

Niu, et al., "Isolation and characterization of an autoinducer synthase from Acinetobacter baumannii.", J Bacteriol. vol. 190(9) p. 3386-3392 (2008).

Novick, "Genetic systems in staphylococci", Methods Enzymol 204, 587-636 (1991).

Patent Cooperation Treaty, International Searching Authority, Search Report and Written Opinion for PCT/US2015/15062, 7 pages, dated Jul. 20, 2015.

Schilcher, et al., "Increased neutrophil extracellular trap-mediated *Staphylococcus aureus* clearance through inhibition of nuclease activity by clindamycin and immunoglobulin.", J Infect Dis. vol. 210(3) p. 473-482 (2014).

Schlievert, et al., "Endotoxin enhancement as a possible etiology of early-onset group B beta-hemolytic Streptococcal sepsis in the newborn.", Obstet Gynecol. vol. 61(5) p. 588-592 (1983).

Stoltz, et al., "Cystic fibrosis pigs develop lung disease and exhibit defective bacterial eradication at birth", Sci Transl Med 2, 29ra31, 18 pages (2010).

Stover, et al., "Complete genome sequence of Pseudomonas aeruginosa PAO1, an opportunistic pathogen.", Nature vol. 406(6799) p. 959-964 (2000).

Straub, et al., "Towards a unified system for detecting waterborne pathogens.", J Microbiol Methods. vol. 53(2) p. 185-197 (2003).

* cited by examiner

FAM—5′—CTACGTAG—3′—ZEN—RQ
         ||||||||
RQ—ZEN—3′—GATGCATC—5′—FAM

Figure 4

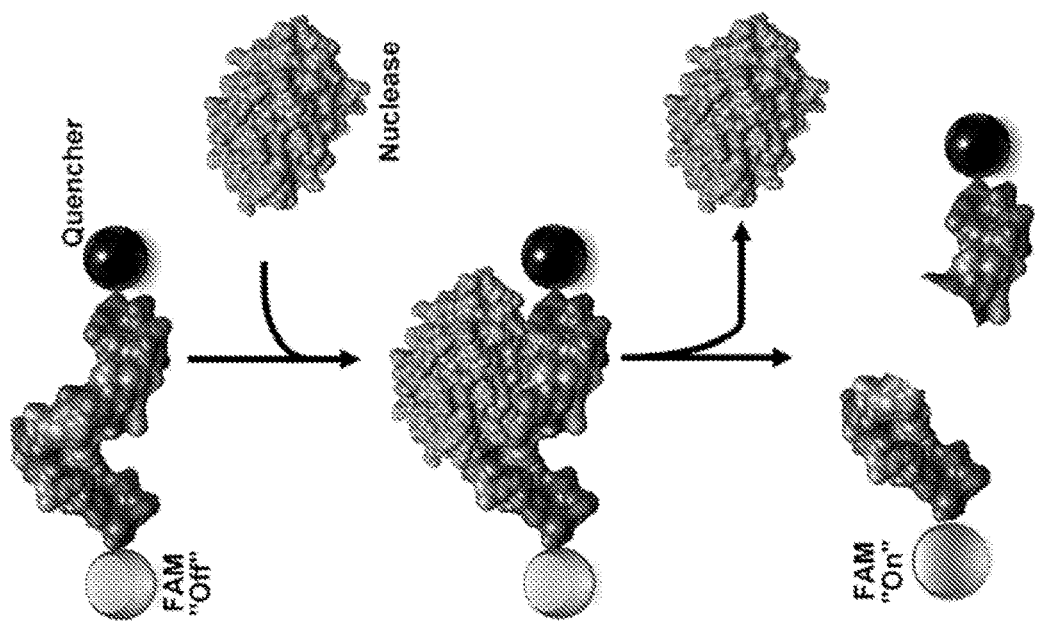

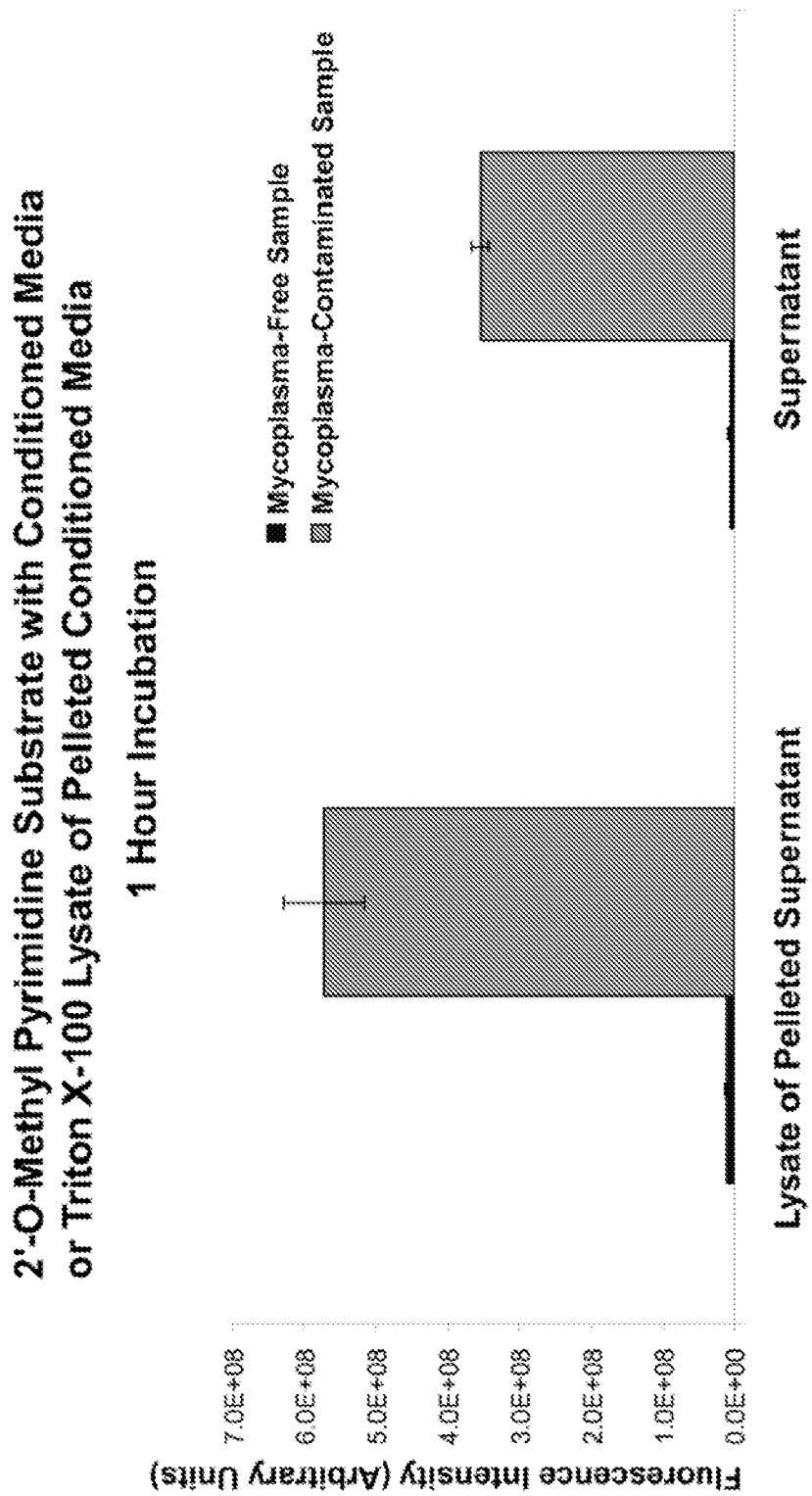

2'-Fluoro Pyrimidine and 2'-O-Methyl Pyrimidine Substrates with Triton X-100 Lysate of *M. fermentans* Bacteria

Figures 18A-D

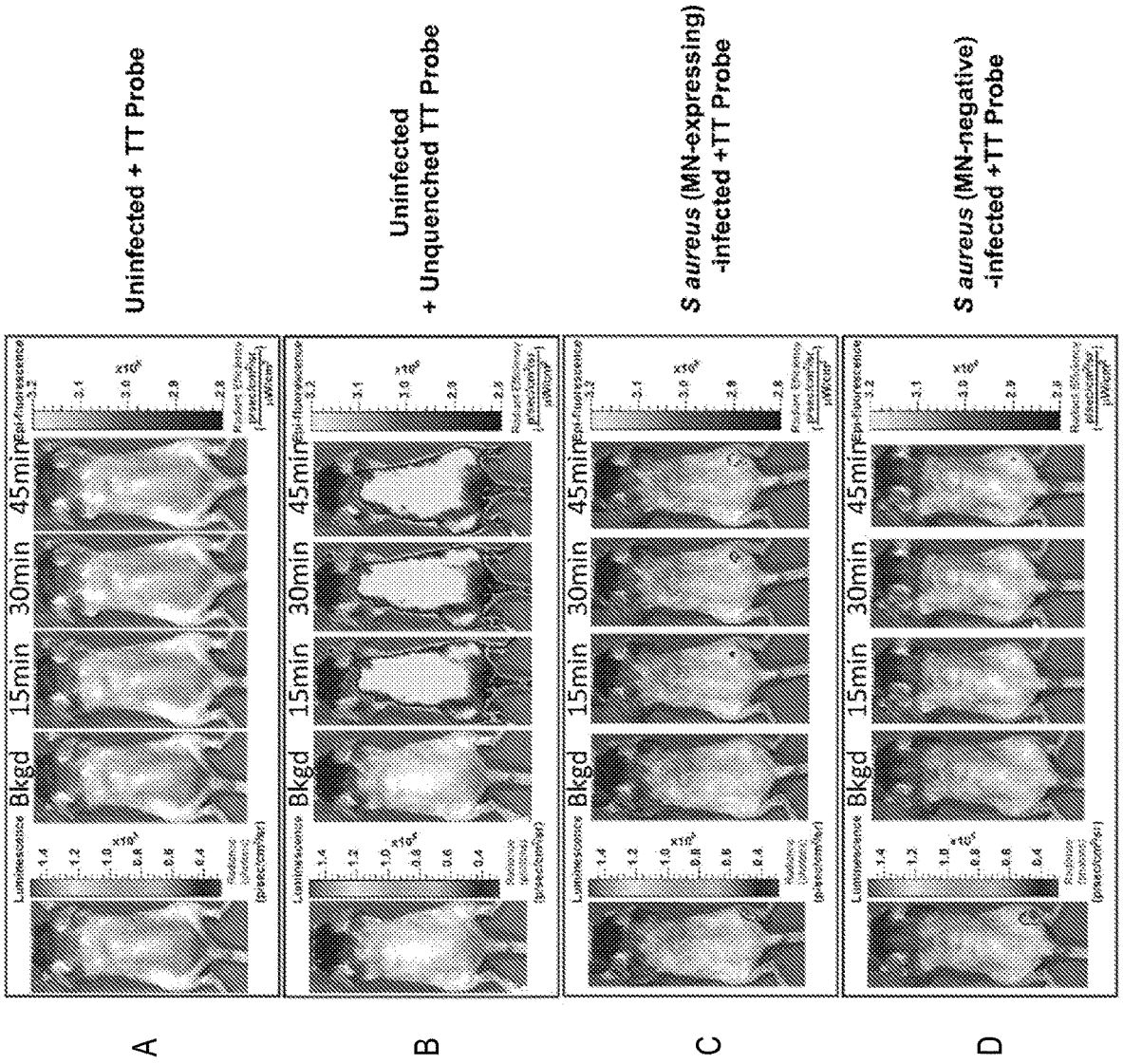
Figures 23A-D

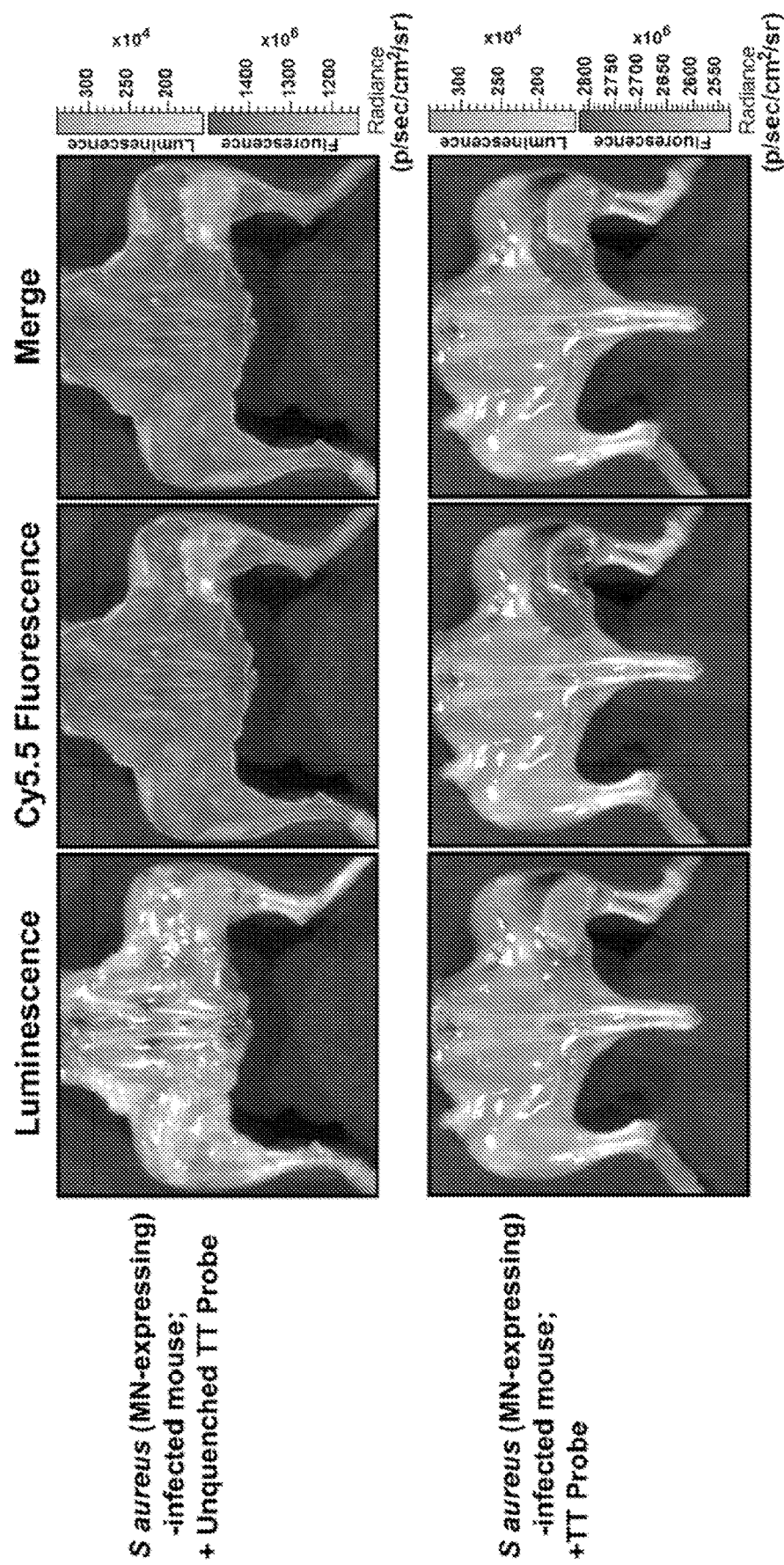

SEQUENCE LISTING

```
<160> NUMBER OF SEQ ID NOS: 56

<210> SEQ ID NO 1
<211> LENGTH: 8
<212> TYPE: DNA
<213> ORGANISM: Unknown
<220> FEATURE:
<223> OTHER INFORMATION: Description of Unknown: Endonuclease
      restriction site oligonucleotide

<400> SEQUENCE: 1 ctacgtag                                                                 8

<210> SEQ ID NO 2
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2 cuacguag                                                                 8

<210> SEQ ID NO 3
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 tggatcca                                                                 8

<210> SEQ ID NO 4
<211> LENGTH: 8
<212> TYPE: RNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 56-FAM
<220> FEATURE:
<221> NAME/KEY: modified_base
<222> LOCATION: (1)..(8)
<223> OTHER INFORMATION: 2'-fluoro nucleotide
<220> FEATURE:
<223> OTHER INFORMATION: 3' ZEN fluorescence quencher-Iowa Black
      fluorescence quencher
```

-continued

```
<400> SEQUENCE: 4 cuacguag                                                              8

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 6-FAM
<220> FEATURE:
<223> OTHER INFORMATION: 3' ZEN dark quencher-Iowa Black dark quencher

<400> SEQUENCE: 5
tttttttttt t                                                          11

<210> SEQ ID NO 6
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' FAM
<220> FEATURE:
<223> OTHER INFORMATION: 3' ZEN fluorescence quencher-Iowa Black
      fluorescence quencher

<400> SEQUENCE: 6
ucucguacgu uc                                                         12

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (3)..(10)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 7
ttuuuuuuuu u                                                          11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
```

-continued

```
<221> NAME/KEY: modified_base
<222> LOCATION: (1)..(2)
<223> OTHER INFORMATION: 2'-O-methyl nucleotide
<220> FEATURE:
<221> NAME/KEY: modified_base
<222> LOCATION: (5)..(11)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 8
uuttuuuuuu u                                                              11

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 9
uuuuttuuuu u                                                              11

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(7)
<223> OTHER INFORMATION: 2'-O-methyl nucleotide
<220> FEATURE:
<221> NAME/KEY: modified_base
<222> LOCATION: (10)..(11)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 10
uuuuuuuttu u                                                              11

<210> SEQ ID NO 11
<211> LENGTH: 11
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(9)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 11
uuuuuuuuut t                                                              11

<210> SEQ ID NO 12
<211> LENGTH: 8
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (6)..(8)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 12 uuuttuuu                                                                   8

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(2)
<223> OTHER INFORMATION: 2'-O-methyl nucleotide
<220> FEATURE:
<221> NAME/KEY: modified_base
<222> LOCATION: (5)..(6)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 13 uuttuu                                                                     6

<210> SEQ ID NO 14
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(4)
<223> OTHER INFORMATION: Unlocked nucleotide
<220> FEATURE:
<221> NAME/KEY: modified_base
<222> LOCATION: (7)..(11)
<223> OTHER INFORMATION: Unlocked nucleotide
<220> FEATURE:
<223> OTHER INFORMATION: 3' ZEN fluorescence quencher-Iowa Black
      fluorescence quencher

<400> SEQUENCE: 14
uuuuttuuuu u                                                         11

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 15 cccottcccc c                                                         11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (4)..(11)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 16
```
uttuuuuuuu u                                                         11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(3)
<223> OTHER INFORMATION: 2'-O-methyl nucleotide
<220> FEATURE:
<221> NAME/KEY: modified_base
<222> LOCATION: (6)..(11)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 17
uuuttuuuuu u                                                         11

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(2)
<223> OTHER INFORMATION: 2'-O-methyl nucleotide
<220> FEATURE:
<221> NAME/KEY: modified_base
<222> LOCATION: (5)..(11)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 18
ugttguuuuu u                                                         11

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(2)
<223> OTHER INFORMATION: 2'-O-methyl nucleotide
<220> FEATURE:

```
<221> NAME/KEY: modified_base
<222> LOCATION: (5)..(11)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 19
uattauuuuu u                                                              11

<210> SEQ ID NO 20
<211> LENGTH: 6
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (3)..(6)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 20 ttuuuu                                                                     6

<210> SEQ ID NO 21
<211> LENGTH: 8
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (3)..(8)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 21 ttuuuuuu                                                                   8

<210> SEQ ID NO 22
<211> LENGTH: 6
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(1)
<223> OTHER INFORMATION: 2'-O-methyl nucleotide
<220> FEATURE:
```

```
<221> NAME/KEY: modified_base
<222> LOCATION: (4)..(6)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 22 uttuuu                                                                       6

<210> SEQ ID NO 23
<211> LENGTH: 8
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(1)
<223> OTHER INFORMATION: 2'-O-methyl nucleotide
<220> FEATURE:
<221> NAME/KEY: modified_base
<222> LOCATION: (4)..(8)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 23 uttuuuuu                                                                     8

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' ZEN fluorescence quencher-Iowa Black
      fluorescence quencher

<400> SEQUENCE: 24
tttttttttt t                                                                11

<210> SEQ ID NO 25
<211> LENGTH: 6
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' ZEN fluorescence quencher-Iowa Black
      fluorescence quencher

<400> SEQUENCE: 25 tttttt                                                                       6

<210> SEQ ID NO 26
<211> LENGTH: 4
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' ZEN fluorescence quencher-Iowa Black
      fluorescence quencher

<400> SEQUENCE: 26 tttt                                                                    4

<210> SEQ ID NO 27
<211> LENGTH: 8
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 56-FAM
<220> FEATURE:
<223> OTHER INFORMATION: 3' ZEN fluorescence quencher-Iowa Black
      fluorescence quencher

<400> SEQUENCE: 27 ctacgtag                                                                8

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (9)..(12)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 28
ucucaaaagu ac                                                          12

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
```

```
<222> LOCATION: (9)..(12)
<223> OTHER INFORMATION: 2'-O-methyl nucleotide

<400> SEQUENCE: 29
guacttttga ga                                                          12

<210> SEQ ID NO 30
<211> LENGTH: 8
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' ZEN fluorescence quencher-Iowa Black
      fluorescence quencher

<400> SEQUENCE: 30 ctacgtag                                                                8

<210> SEQ ID NO 31
<211> LENGTH: 8
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (1)..(8)
<223> OTHER INFORMATION: Locked nucleotide
<220> FEATURE:
<223> OTHER INFORMATION: 3' ZEN fluorescence quencher-Iowa Black
      fluorescence quencher

<400> SEQUENCE: 31 ctacgtag                                                                8

<210> SEQ ID NO 32
<211> LENGTH: 8
<212> TYPE: RNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (1)..(8)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 32 cuacguag                                                                8

<210> SEQ ID NO 33
<211> LENGTH: 8
<212> TYPE: RNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
```

```
<220> FEATURE:
<221> NAME/KEY: modified_base
<222> LOCATION: (1)..(8)
<223> OTHER INFORMATION: 2'-fluoro nucleotide
<220> FEATURE:
<223> OTHER INFORMATION: 3' ZEN fluorescence quencher-Iowa Black
      fluorescence quencher

<400> SEQUENCE: 33 cuacguag                                                                  8

<210> SEQ ID NO 34
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gggaggacga ugcgggacua gcgaucuguu acgcacagac gacucgcccg a                 51

<210> SEQ ID NO 35
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-fluoro nucleotide
<220> FEATURE:
<221> NAME/KEY: modified_base
<222> LOCATION: (11)..(11)
<223> OTHER INFORMATION: 2'-fluoro nucleotide
<220> FEATURE:
<221> NAME/KEY: modified_base
<222> LOCATION: (13)..(13)
<223> OTHER INFORMATION: 2'-fluoro nucleotide
<220> FEATURE:
<221> NAME/KEY: modified_base
<222> LOCATION: (18)..(19)
<223> OTHER INFORMATION: 2'-fluoro nucleotide
<220> FEATURE:
<221> NAME/KEY: modified_base
<222> LOCATION: (22)..(22)
<223> OTHER INFORMATION: 2'-fluoro nucleotide
<220> FEATURE:
<221> NAME/KEY: modified_base
<222> LOCATION: (25)..(27)
<223> OTHER INFORMATION: 2'-fluoro nucleotide
<220> FEATURE:
<221> NAME/KEY: modified_base
<222> LOCATION: (29)..(30)
<223> OTHER INFORMATION: 2'-fluoro nucleotide
<220> FEATURE:
<221> NAME/KEY: modified_base
<222> LOCATION: (32)..(32)
<223> OTHER INFORMATION: 2'-fluoro nucleotide
<220> FEATURE:
<221> NAME/KEY: modified_base
<222> LOCATION: (34)..(34)
<223> OTHER INFORMATION: 2'-fluoro nucleotide
<220> FEATURE:
<221> NAME/KEY: modified_base
<222> LOCATION: (36)..(36)
<223> OTHER INFORMATION: 2'-fluoro nucleotide
<220> FEATURE:
<221> NAME/KEY: modified_base
<222> LOCATION: (40)..(40)
<223> OTHER INFORMATION: 2'-fluoro nucleotide
<220> FEATURE:
<221> NAME/KEY: modified_base
```

```
<222> LOCATION: (43)..(45)
<223> OTHER INFORMATION: 2'-fluoro nucleotide
<220> FEATURE:
<221> NAME/KEY: modified_base
<222> LOCATION: (47)..(49)
<223> OTHER INFORMATION: 2'-fluoro nucleotide
<220> FEATURE:
<223> OTHER INFORMATION: 3' FAM

<400> SEQUENCE: 35
gggaggacga ugcgggacua gcgaucuguu acgcacagac gacucgcccg a          51

<210> SEQ ID NO 36
<211> LENGTH: 11
<212> TYPE: RNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' Cy5.5
<220> FEATURE:
<223> OTHER INFORMATION: 3' ZEN fluorescence quencher-Iowa Black
      fluorescence quencher

<400> SEQUENCE: 36
cucguacguu c                                                      11

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 56-FAM
<220> FEATURE:
<223> OTHER INFORMATION: 3' ZEN fluorescence quencher-Iowa Black
      fluorescent quencher

<400> SEQUENCE: 37
ttccttcctc                                                        10

<210> SEQ ID NO 38
<211> LENGTH: 12
<212> TYPE: RNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 56-FAM
<220> FEATURE:
<221> NAME/KEY: modified_base
<222> LOCATION: (1)..(12)
<223> OTHER INFORMATION: 2'-O-methyl nucleotide
<220> FEATURE:
<223> OTHER INFORMATION: 3' ZEN fluorescence quencher-Iowa Black
      fluorescent quencher

<400> SEQUENCE: 38
ucucguacgu uc                                                     12

<210> SEQ ID NO 39
<211> LENGTH: 12
<212> TYPE: RNA
<213> ORGANISM: Artificial Sequence
<220> FEATURE:
<223> OTHER INFORMATION: Description of Artificial Sequence: Synthetic
      probe
```

```
<220> FEATURE:
<223> OTHER INFORMATION: 5' 56-FAM
<220> FEATURE:
<221> NAME/KEY: modified_base
<222> LOCATION: (1)..(12)
<223> OTHER INFORMATION: 2'-fluoro nucleotide
<220> FEATURE:
<223> OTHER INFORMATION: 3' ZEN fluorescence quencher-Iowa Black
      fluorescent quencher

<400> SEQUENCE: 39
ucucguacgu uc                                                              12

<210> SEQ ID NO 40
<211> LENGTH: 11
<212> TYPE: RNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 56-FAM
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' ZEN fluorescence quencher-Iowa Black
      fluorescent quencher

<400> SEQUENCE: 40
cucgaacguu c                                                               11

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' 56-FAM
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' ZEN fluorescence quencher-Iowa Black
      fluorescent quencher

<400> SEQUENCE: 41
cucgttcguu c                                                               11

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
```

```
      Synthetic probe
<220> FEATURE:
<223> OTHER INFORMATION: 5' 56-FAM
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' ZEN fluorescence quencher-Iowa Black
      fluorescent quencher

<400> SEQUENCE: 42
cucgatcguu c                                                              11

<210> SEQ ID NO 43
<211> LENGTH: 12
<212> TYPE: RNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (1)..(4)
<223> OTHER INFORMATION: 2'-fluoro nucleotide
<220> FEATURE:
<221> NAME/KEY: modified_base
<222> LOCATION: (6)..(6)
<223> OTHER INFORMATION: 2'-fluoro nucleotide
<220> FEATURE:
<221> NAME/KEY: modified_base
<222> LOCATION: (8)..(8)
<223> OTHER INFORMATION: 2'-fluoro nucleotide
<220> FEATURE:
<221> NAME/KEY: modified_base
<222> LOCATION: (10)..(12)
<223> OTHER INFORMATION: 2'-fluoro nucleotide
<220> FEATURE:
<223> OTHER INFORMATION: 3' ZEN fluorescence quencher-Iowa Black
      fluorescence quencher

<400> SEQUENCE: 43
ucucguacgu uc                                                             12

<210> SEQ ID NO 44
<211> LENGTH: 12
<212> TYPE: RNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (6)..(6)
<223> OTHER INFORMATION: 2'-O-methyl nucleotide
<220> FEATURE:
<221> NAME/KEY: modified_base
<222> LOCATION: (8)..(8)
<223> OTHER INFORMATION: 2'-O-methyl nucleotide
<220> FEATURE:
<221> NAME/KEY: modified_base
<222> LOCATION: (10)..(12)
<223> OTHER INFORMATION: 2'-O-methyl nucleotide
```

```
<220> FEATURE:
<223> OTHER INFORMATION: 3' ZEN fluorescence quencher-Iowa Black
      fluorescence quencher

<400> SEQUENCE: 44
ucucguacgu uc                                                          12

<210> SEQ ID NO 45
<211> LENGTH: 12
<212> TYPE: RNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (1)..(12)
<223> OTHER INFORMATION: 2'-fluoro nucleotide
<220> FEATURE:
<223> OTHER INFORMATION: 3' ZEN fluorescence quencher-Iowa Black
      fluorescence quencher

<400> SEQUENCE: 45
ucucguacgu uc                                                          12

<210> SEQ ID NO 46
<211> LENGTH: 12
<212> TYPE: RNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (1)..(12)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 46
ucucguacgu uc                                                          12

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' ZEN fluorescence quencher-Iowa Black
      fluorescence quencher

<400> SEQUENCE: 47
ttccttcctc                                                             10

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

```
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 48
cucgttcguu c                                                          11

<210> SEQ ID NO 49
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' Cy5.5
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 49
cucgttcguu c                                                          11

<210> SEQ ID NO 50
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' Cy5.5
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<221> NAME/KEY: modified_base
<222> LOCATION: (12)..(12)
<223> OTHER INFORMATION: Inverted nucleotide

<400> SEQUENCE: 50
cucgttcguu ct                                                         12
```

```
<210> SEQ ID NO 51
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' FAM
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' ZEN fluorescence quencher-Iowa Black
      fluorescence quencher

<400> SEQUENCE: 51
cucgttcguu c                                                        11

<210> SEQ ID NO 52
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' IRDye800CW fluorophore
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' QC-1 quencher

<400> SEQUENCE: 52
cucgttcguu c                                                        11

<210> SEQ ID NO 53
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' Dy780 fluorophore
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
```

<223> OTHER INFORMATION: 3' QC-1 quencher

<400> SEQUENCE: 53
cucgttcguu c                                                                 11

<210> SEQ ID NO 54
<211> LENTGH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' Dy781 fluorophore
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' QC-1 quencher

<400> SEQUENCE: 54
cucgttcguu c                                                                 11

<210> SEQ ID NO 55
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' DyLight 800 fluorophore
<220> FEATURE:
<221> NAME/KEY: modified_base
<222> LOCATION: (1)..(4)
<223> OTHER INFORMATION: 2'-O-methyl nucleotide
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' QC-1 quencher

<400> SEQUENCE: 55
cucgttcguu c                                                                 11

<210> SEQ ID NO 56
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<223> OTHER INFORMATION: 5' Cy7.5 fluorophore
<220> FEATURE:
<221> NAME/KEY: modified_base
<222> LOCATION: (1)..(4)
<223> OTHER INFORMATION: 2'-O-methyl nucleotide

```
<220> FEATURE:
<221> NAME/KEY: modified_base
<222> LOCATION: (7)..(11)
<223> OTHER INFORMATION: 2'-O-methyl nucleotide
<220> FEATURE:
<223> OTHER INFORMATION: 3' QC-1 quencher

<400> SEQUENCE: 56
cucgttcguu c                                                              11
```

OLIGONUCLEOTIDE-BASED PROBES AND METHODS FOR DETECTION OF MICROBES

RELATED APPLICATION

This application claims priority to U.S. Provisional Patent Application No. 61/937,359, filed Feb. 7, 2014, and to U.S. Provisional Patent Application No. 61/992,034, filed May 12, 2014, and to U.S. Provisional Patent Application No. 61/980,498, filed Apr. 16, 2014, the entirety of which are incorporated herein by reference.

FEDERAL GRANT SUPPORT

This invention was made with government support under AI083211, 1R21AI101391-01A1 and 1R01AI106738-01 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 3, 2015, is named 17023_143WO1_SL.txt and is 27,134 bytes in size.

BACKGROUND OF THE INVENTION

Chemical moieties that quench fluorescent light operate through a variety of mechanisms, including fluorescence resonance energy transfer (FRET) processes and ground state quenching. FRET is one of the most common mechanisms of fluorescent quenching and can occur when the emission spectrum of the fluorescent donor overlaps the absorbance spectrum of the quencher and when the donor and quencher are within a sufficient distance known as the Forster distance. The energy absorbed by a quencher can subsequently be released through a variety of mechanisms depending upon the chemical nature of the quencher. Captured energy can be released through fluorescence or through nonfluorescent mechanisms, including charge transfer and collisional mechanisms, or a combination of such mechanisms. When a quencher releases captured energy through nonfluorescent mechanisms FRET is simply observed as a reduction in the fluorescent emission of the fluorescent donor.

Although FRET is the most common mechanism for quenching, any combination of molecular orientation and spectral coincidence that results in quenching is a useful mechanism for quenching by the compounds of the present invention. For example, ground-state quenching can occur in the absence of spectral overlap if the fluorophore and quencher are sufficiently close together to form a ground state complex.

Quenching processes that rely on the interaction of two dyes as their spatial relationship changes can be used conveniently to detect and/or identify nucleotide sequences and other biological phenomena. As noted previously, the energy transfer process requires overlap between the emission spectrum of the fluorescent donor and the absorbance spectrum of the quencher. This complicates the design of probes because not all potential quencher/donor pairs can be used. For example, the quencher BHQ-1, which maximally absorbs light in the wavelength range of about 500-550 nm, can quench the fluorescent light emitted from the fluorophore fluorescein, which has a wavelength of about 520 nm. In contrast, the quencher BHQ-3, which maximally absorbs light in the wavelength range of about 650-700 nm would be less effective at quenching the fluorescence of fluorescein but would be quite effective at quenching the fluorescence of the fluorophore Cy5 which fluoresces at about 670 nm. The use of varied quenchers complicates assay development because the purification of a given probe can vary greatly depending on the nature of the quencher attached.

Many quenchers emit energy through fluorescence reducing the signal to noise ratio of the probes that contain them and the sensitivity of assays that utilize them. Such quenchers interfere with the use of fluorophores that fluoresce at similar wavelength ranges. This limits the number of fluorophores that can be used with such quenchers thereby limiting their usefulness for multiplexed assays which rely on the use of distinct fluorophores in distinct probes that all contain a single quencher.

Endonucleases (e.g., certain ribonucleases and deoxyribonucleases) are enzymes that cleave the phosphodiester bond within a polynucleotide (DNA or RNA) chain, in contrast to exonucleases, which cleave phosphodiester bonds at the end of a polynucleotide chain. Typically, a restriction site, i.e., a recognition site for an endonuclease, is a palindromic sequence four to six nucleotides long (e.g., TGGATCCA, SEQ ID NO:3).

Endonucleases, found in bacteria and archaea, are thought to have evolved to provide a defense mechanism against invading viruses. Inside a bacterial host, the restriction enzymes selectively cut up foreign DNA in a process called restriction; host DNA is methylated by a modification enzyme (a methylase) to protect it from the restriction enzyme's activity. Collectively, these two processes form the restriction modification system. To cut the DNA, a restriction enzyme makes two incisions, once through each sugar-phosphate backbone (i.e. each strand) of the DNA double helix.

Some cells secrete copious quantities of non-specific RNases such as A and T1. RNases are extremely common, resulting in very short lifespans for any RNA that is not in a protected environment. Similar to restriction enzymes, which cleave highly specific sequences of double-stranded DNA, a variety of endoribonucleases that recognize and cleave specific sequences of single-stranded RNA have been recently classified.

Present technologies for detection of bacterial pathogens are time-consuming and expensive because they usually require the isolation and culturing of the bacteria. Also, many of the existing technologies are toxic and/or use radioactive tracers. Further, technologies for imaging bacterial colonization in humans lack sensitivity. Accordingly, a rapid, inexpensive, non-toxic bacterial-specific assay is needed.

SUMMARY OF THE INVENTION

In certain embodiments, the present invention provides a probe for detecting bacterial or viral endonucleases (e.g., a ribonuclease or a deoxyribonuclease) comprising an oligonucleotide of 2-30 nucleotides in length, at least one fluorophore operably linked to the oligonucleotide, and at least one fluorescence quencher operably linked to the oligonucleotide, wherein the oligonucleotide is capable of being specifically cleaved by bacterial or viral endonuclease but not by a mammalian nuclease or a non-bacterial or non-viral nuclease. In certain embodiments, the oligonucleotide is 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides in length.

In certain embodiments, the present invention provides a probe for detecting bacterial or viral endonuclease comprising an oligonucleotide of 2-30 nucleotides in length, at least one fluorophore operably linked to the oligonucleotide, and at least one fluorescence quencher operably linked to the oligonucleotide, wherein the oligonucleotide comprises at least 4 contiguous nucleotides of CTACGTAG (SEQ ID NO:1) or CUACGUAG (SEQ ID NO:2). In certain embodiments, the oligonucleotide is 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides in length.

In certain embodiments, the present invention provides a probe for detecting bacterial or viral endonuclease comprising an oligonucleotide of 2-30 nucleotides in length, at least one fluorophore operably linked to the oligonucleotide, and at least one fluorescence quencher operably linked to the oligonucleotide, wherein the oligonucleotide comprises CTACGTAG (SEQ ID NO:1) or CUACGUAG (SEQ ID NO:2).

The fluorescence-reporter group and the fluorescence-quencher group are separated by at least one endonuclease-cleavable residue, e.g., RNA base or DNA base. Such residues serve as a cleavage domain for endonucleases. In certain embodiments, the oligonucleotide is 10-15 nucleotides in length. In certain embodiments, the oligonucleotide is 11-13 nucleotides in length.

In certain embodiments, the oligonucleotide comprises 0-50% purines or any value in between. In certain embodiments the oligonucleotide comprises 100% pyrimidines. In certain embodiments one or more of the pyrimidines are chemically modified. In certain embodiments, one or more of the pyrimidines are 2'-O-methyl modified. In certain embodiments, one or more of the pyrimidines are 2'-fluoro modified. In certain embodiments, one or more of the purines are chemically modified. In certain embodiments, one or more of the purines are 2'-O-methyl modified. In certain embodiments, one or more of the purines are 2'-fluoro modified.

In certain embodiments, the at least one fluorophore is selected from the group consisting of the fluorophores listed in Table 1, such as for example, a fluorophore that has an emission in the near infra-red range. In certain embodiments, the fluorophore is a FAM fluorophore.

In certain embodiments, the at least one fluorescence quencher is selected from the group consisting of the quenchers listed in Table 2. In certain embodiments, the at least one fluorescence quencher is ZEN fluorescence quencher and/or Iowa Black fluorescence quencher. In certain embodiments, the fluorophore is a FAM fluorophores, and the at least one fluorescence quencher is ZEN and 3IAbRQSp.

In certain embodiments, the probe comprises two oligonucleotides that are completely self-complementary yielding a double-stranded nucleic acid. In certain embodiments, the oligonucleotide comprises both RNA and DNA. In certain embodiments, the oligonucleotide consists of DNA.

In certain embodiments, the probe consists of 56-FAM/ fCfUfAfCfGfUfAfG/ZEN/3IAbRQSp (SEQ ID NO: 4).

In certain embodiments, the probe consists of FAM/ TTTTTTTTTTT/ZEN/IAbRQSp/(SEQ ID NO:5), wherein 6-FAM is a fluorescein amidite fluorophore, ZEN is a ZEN dark quencher, and IAbRQSp is a Iowa Black dark quencher.

In certain embodiments, the microbial endonuclease is a bacterial endonuclease.

In certain embodiments, the bacterial endonuclease is a Staphylococcus aureus, Staphylococcus epidermidis, Staphylococcus lugdunensis, Staphylococcus saprophyticus, Streptococcus pyogenes, Streptococcus agalactiae, Streptococcus pneumoniae, Streptococcus mutans, Listeria monocytogenes, Corynebacterium diphtheriae, Bordetella pertussis, Clostridium difficile, Clostridium perfringens, Clostridium botulinum, Enterobacter cloacae, Citrobacter freundii, Borrelia burgdorferi, Treponema pallidum, Bacillus anthracis, Bacillus cereus, Enterococcus faecalis, Enterococcus faecium, Pseudomonas aeruginosa, Acinetobacter baumannii, Yersinia pestis, Yersinia pseudotuberculosis, Yersinia enterocolitica, Klebsiella pneumoniae, Vibrio cholerae, Salmonella enterica, Salmonella typhi, Escherichia coli, Neisseria gonorrhoeae, Neisseria meningitidis, Mycobacterium tuberculosis, Haemophilus influenzae, Legionella pneumophila, Francisella tularensis, Bacteroides fragilis, Brucella abortus, Mycoplasma fermentans, Mycoplasma pneumonia, Mycoplasma genitalium, and/or Chlamydia trachomatis endonuclease.

In certain embodiments, the bacterial endonuclease is an E. coli endonuclease.

In certain embodiments, the microbial endonuclease is a viral endonuclease.

In certain embodiments, the viral endonuclease is a Cytomegalovirus, Human Herpes Virus 1, 2, 3, 4, 5, 6A, 6B, 7 and/or 8 endonuclease.

In certain embodiments, the present invention provides a method of detecting the presence of bacteria or viruses (microbes) in a sample comprising measuring fluorescence of a sample that has been contacted with a probe described above, wherein a fluorescence level that is greater than the fluorescence level of a microbe-free control indicates that the sample contains a microbe. In certain embodiments, the test fluorescence level is at least 1-100% greater (or any value in between, e.g., 2%, 10%, 20%, 80% 90%) than the control level.

In certain embodiments, the fluorophore absorbs in the range of 650-850 nm.

In certain embodiments, the method is an in vitro assay, and wherein the fluorophore is FAM or Cy5.5.

In certain embodiments, the fluorophore is Cy5, Cy5.5, Cy7, Licor IRDye 700, Licor IRDye 800 CW, or Alexa Fluor 647, 660, 680, 750, an/or 790.

In certain embodiments, the fluorophore is FAM, TET, HEX, JOE, MAX, Cy3, or TAMRA and the quencher is IBFQ, BHQ1, BHQ2, or Licor IRDye QC-1.

In certain embodiments, the fluorophore is ROX, Texas Red, Cy5, or Cy5.5 and the quencher is IBRQ or BHQ2.

In certain embodiments, the present invention provides a method of in vivo detection of a microbial infection in a mammal comprising measuring fluorescence in the mammal, wherein the mammal has been administered a probe described above, wherein a test fluorescence that is greater than the fluorescence level of an uninfected control indicates that the sample has a microbial infection. In certain embodiments, the fluorophore is detectable at a depth of 7-14 cm in the mammal.

In certain embodiments, the present invention provides a method for detecting bacterial or viral endonuclease activity in a test sample, comprising: (a) contacting the test sample with a probe described above, thereby creating a test reaction mixture, (b) incubating the test reaction mixture for a time sufficient for cleavage of the probe by a bacterial or viral endonuclease in the sample; and (c) determining whether a detectable fluorescence signal is emitted from the test reaction mixture, wherein emission of a fluorescence signal from the reaction mixture indicates that the sample contains a bacterial or viral endonuclease activity.

In certain embodiments, the present invention provides a method for detecting a bacterial or viral endonuclease activity in a test sample, comprising: (a) contacting the test sample with a probe described above, thereby creating a test reaction mixture, (b) incubating the test reaction mixture for a time sufficient for cleavage of the substrate by a bacterial or viral endonuclease in the test sample; (c) determining whether a detectable fluorescence signal is emitted from the test reaction mixture; (d) contacting a control sample with the substrate, the control sample comprising a predetermined amount of the bacterial or viral endonuclease, thereby creating a control reaction mixture; (e) incubating the control reaction mixture for a time sufficient for cleavage of the substrate by a bacterial or viral endonuclease in the control sample; and (f) determining whether a detectable fluorescence signal is emitted from the control reaction mixture; wherein detection of a greater fluorescence signal in the test reaction mixture than in the control reaction mixture indicates that the test sample contains greater bacterial or viral endonuclease activity than in the control sample, and wherein detection of a lesser fluorescence signal in the test reaction mixture than in the control reaction mixture indicates that the test sample contains less bacterial or viral endonuclease activity than in the control sample.

In certain embodiments, the predetermined amount of bacterial or viral endonuclease is no bacterial or viral endonuclease, such that detection of a greater fluorescence signal in the test reaction mixture than in the control reaction mixture indicates that the test sample contains bacterial or viral endonuclease activity.

In certain embodiments, the method further comprises contacting the test sample with a reaction buffer before or during step (a).

In certain embodiments, the reaction buffer comprises: 50 mM Tris-HCl, pH 8.0, 100 mM NaCl, 12 mM $MgCl_2$, 1% Triton X-100, 1 mM DTT, and 1× Protease Inhibitor Cocktail.

In certain embodiments, the bacterial or viral endonuclease is *E. coli* Endonuclease I.

In certain embodiments, the microbe is a bacterium or a virus.

In certain embodiments, the bacterium is *Staphylococcus aureus, Staphylococcus epidermidis, Staphylococcus lugdunensis, Staphylococcus saprophyticus, Streptococcus pyogenes, Streptococcus agalactiae, Streptococcus pneumoniae, Streptococcus mutans, Listeria monocytogenes, Corynebacterium diphtheriae, Bordetella pertussis, Clostridium difficile, Clostridium perfringens, Clostridium botulinum, Enterobacter cloacae, Citrobacter freundii, Borrelia burgdorferi, Treponema pallidum, Bacillus anthracis, Bacillus cereus, Enterococcus faecalis, Enterococcus faecium, Pseudomonas aeruginosa, Acinetobacter baumannii, Yersinia pestis, Yersinia pseudotuberculosis, Yersinia enterocolitica, Klebsiella pneumoniae, Vibrio cholerae, Salmonella enterica, Salmonella typhi, Escherichia coli, Neisseria gonorrhoeae, Neisseria meningitidis, Mycobacterium tuberculosis, Haemophilus influenzae, Legionella pneumophila, Francisella tularensis, Bacteroides fragilis, Brucella abortus, Mycoplasma fermentans, Mycoplasma pneumonia, Mycoplasma genitalium*, and/or *Chlamydia trachomatis*.

In certain embodiments, the bacterium is *E. coli*.

In certain embodiments, the microbe is a virus.

In certain embodiments, the virus is a Cytomegalovirus, Human Herpes Virus 1, 2, 3, 4, 5, 6A, 6B, 7 and/or 8 virus.

Accordingly, in certain embodiments, the present invention provides probe for detecting a microbial endonuclease comprising an oligonucleotide of 2-30 nucleotides in length, a fluorophore operably linked to the oligonucleotide, and a quencher operably linked to the oligonucleotide, wherein the oligonucleotide comprises one or more modified pyrimidines, is capable of being cleaved by a microbial nuclease, and has a DNA TT di-nucleotide, DNA AT di-nucleotide, DNA AA di-nucleotide or DNA TA di-nucleotide positioned at nucleotides 1 and 2, 2 and 3 or 3 and 4. In certain embodiments, the present invention provides a probe for detecting a microbial endonuclease comprising an oligonucleotide of 2-30 nucleotides in length, a fluorophore operably linked to the oligonucleotide, and a quencher operably linked to the oligonucleotide, wherein the oligonucleotide comprises one or more modified pyrimidines, is resistant to cleavage by mammalian nucleases, and has a DNA TT di-nucleotide positioned at nucleotides 1 and 2 or at nucleotides 2 and 3. As defined herein, the term "resistant to cleavage by mammalian nucleases" means that the oligonucleotide is more readily cleaved by a microbial endonuclease than by a mammalian nuclease. In certain embodiments, the oligonucleotide is cleaved at least 1%, 10%, 100%, or greater than 100% more readily by a microbial endonuclease than by a mammalian nuclease. In certain embodiments, the oligonucleotide is 8-15 nucleotides in length and the DNA TT di-nucleotide is positioned at nucleotides 2 and 3. In certain embodiments, the oligonucleotide is 8-11 nucleotides in length and the DNA TT di-nucleotide is positioned at nucleotides 2 and 3. In certain embodiments, the oligonucleotide is 4-6 nucleotides in length and the DNA TT di-nucleotide is positioned at nucleotides 1 and 2. In certain embodiments, the oligonucleotide is 6 nucleotides in length and the DNA TT di-nucleotide is positioned at nucleotides 1 and 2. In certain embodiments, the probe has greater stability in serum than NMTT probe. In certain embodiments the DNA TT di-nucleotide consists of unmodified deoxythymidines. In certain embodiments, the nucleotides at positions other than the DNA TT di-nucleotide are individually selected from A, C, G or U. In certain embodiments, the nucleotides at positions other than the DNA TT di-nucleotide are modified.

In certain embodiments, the oligonucleotide comprises 0-50% purines or any value in between. In certain embodiments the oligonucleotide comprises 100% pyrimidines. In certain embodiments one or more of the pyrimidines are chemically modified. In certain embodiments, one or more of the pyrimidines are 2'-O-methyl modified. In certain embodiments, one or more of the pyrimidines are 2'-fluoro modified. In certain embodiments, one or more of the purines are chemically modified. In certain embodiments, one or more of the purines are 2'-O-methyl modified. In certain embodiments, one or more of the purines are 2'-fluoro modified. In certain embodiments, the oligonucleotide is RNA.

In certain embodiments, the fluorophore is selected from the group consisting of the fluorophores listed in Table 1, such as for example, a fluorophore that has an emission in the near infra-red range. In certain embodiments, the quencher is selected from the group consisting of the quenchers listed in Table 2. In certain embodiments, the oligonucleotide is single-stranded.

In certain embodiments, the oligonucleotide comprises both RNA and DNA.

In certain embodiments, the present invention provides an oligonucleotide substrate consisting of

```
                                              (SEQ ID NO: 7)
FAM-T T mU mU mU mU mU mU mU mU mU-ZEN-RQ;

(SEQ ID NO: 8)
FAM-mU mU T T mU mU mU mU mU mU mU-ZEN-RQ;

(SEQ ID NO: 9)
FAM-mU mU mU mU T T mU mU mU mU mU-ZEN-RQ;

(SEQ ID NO: 10)
FAM-mU mU mU mU mU mU mU T T mU mU-ZEN-RQ;

(SEQ ID NO: 11)
FAM-mU mU mU mU mU mU mU mU mU T T-ZEN-RQ;

(SEQ ID NO: 12)
FAM-mU mU mU T T mU mU mU-ZEN-RQ;

(SEQ ID NO: 13)
FAM-mU mU T T mU mU-ZEN-RQ;

(SEQ ID NO: 14)
FAM-UNA-U UNA-U UNA-U UNA-U T T UNA-U UNA-U
UNA-U UNA-U UNA-U-ZEN-RQ;

(SEQ ID NO: 15)
FAM-mC mC mC mC T T mC mC mC mC mC-ZEN-RQ;

(SEQ ID NO: 16)
FAM-mU T T mU mU mU mU mU mU mU mU-ZEN-RQ;

(SEQ ID NO: 17)
FAM-mU mU mU T T mU mU mU mU mU mU-ZEN-RQ;

(SEQ ID NO: 18)
FAM-mU mG T T mG mU mU mU mU mU mU-ZEN-RQ;

(SEQ ID NO: 19)
FAM-mU mA T T mA mU mU mU mU mU mU-ZEN-RQ;

(SEQ ID NO: 20)
FAM-T T mU mU mU mU-ZEN-RQ;

(SEQ ID NO: 21)
FAM-T T mU mU mU mU mU mU-ZEN-RQ;

(SEQ ID NO: 22)
FAM-mU T T mU mU mU-ZEN-RQ;

(SEQ ID NO: 23)
FAM-mU T T mU mU mU mU-ZEN-RQ;

(SEQ ID NO: 24)
FAM-T T T T T T T T T T T-ZEN-RQ;

(SEQ ID NO: 25)
FAM-T T T T T-ZEN-RQ;
or
                                              (SEQ ID NO: 26)
FAM-T T T T-ZEN-RQ.
```

The present invention in certain embodiments further provides a method of detecting a microbial infection of a sample comprising measuring fluorescence of a sample that has been contacted with a probe described above, wherein a fluorescence level that is greater than the fluorescence level of an uninfected control indicates that the sample has a microbial infection. In certain embodiments, the level is at least 1-100% greater than the control level.

In certain embodiments, the method is an in vitro assay. In certain embodiments, the fluorophore is FAM, TET, HEX, JOE, MAX, Cy3, or TAMRA and the quencher is IBFQ, BHQ1 or BHQ2. In certain embodiments, the fluorophore is ROX, Texas Red, Cy5, or Cy5.5 and the quencher is IBRQ or BHQ2.

The present invention in certain embodiments further provides a method of in vivo detection of a microbial infection in a mammal comprising measuring fluorescence in the mammal, wherein the mammal has been administered a probe as described above, wherein a fluorescence level that is greater than the fluorescence level of an uninfected control indicates that the sample has a microbial infection. In certain embodiments, the level is at least 1-100% greater than the control level. In certain embodiments, the fluorophore absorbs in the range of 650-900 nm. In certain embodiments, the fluorophore is Cy5, Cy5.5, Cy7, Licor IRD700, Cy7.5, Dy780, Dy781, DyLight 800, Licor IRDye 800 CW, Alexa 647, 660, 680, 750, or 790. In certain embodiments, the fluorophore is detectable at a depth of 7-14 cm in the mammal. In certain embodiments, the microbial infection is a *Mycoplasma* infection. In certain embodiments, the microbial infection is a *Staphylococcus aureus* or *Streptococcus pneumoniae* infection.

In certain embodiments, the present invention provides in vitro assays for evaluating the activity of microbial nucleases on various nucleic acid substrates. In certain embodiments the assay evaluates the activity of *Mycoplasma* nucleases. In certain embodiments the assay evaluates the activity of *Staphylococcus aureus* or *Streptococcus pneumoniae* nucleases.

In certain embodiments, the methods include detection of bacterial contamination in research laboratories, medical diagnostic applications and medical diagnostic imaging.

In certain embodiments, the present invention provides a method for detecting nuclease (e.g., endonuclease, such as certain ribonucleases or deoxyribonucleases) activity in a test sample, comprising: (a) selectively inactivating mammalian nucleases in a sample; (b) contacting the test sample with a substrate, thereby creating a test reaction mixture, wherein the substrate comprises a nucleic acid molecule comprising: (i) a cleavage domain comprising a single-stranded region of RNA, the single-stranded region comprising a 2'-fluoro modified pyrimidine or 2'-O-methyl modified pyrimidine that renders the oligonucleotide resistant to degradation by mammalian nucleases; (ii) a fluorescence reporter group on one side of the internucleotide linkages; and iii. a non-fluorescent fluorescence-quenching group on the other side of the internucleotide linkages; (c) incubating the test reaction mixture for a time sufficient for cleavage of the substrate by a nuclease (e.g., endonuclease, such as certain ribonucleases or deoxyribonucleases) in the sample; and (d) determining whether a detectable fluorescence signal is emitted from the test reaction mixture, wherein emission of a fluorescence signal from the reaction mixture indicates that the sample contains nuclease (e.g., endonuclease, such as certain ribonucleases or deoxyribonucleases) activity. As defined herein, the term "selectively inactivating mammalian nucleases" means that mammalian nucleases present in the sample are reduced at least 1%, 10%, 100%, as compared to a sample that has not been inactivated.

In certain embodiments, the present invention provides a method for detecting nuclease (e.g., endonuclease, such as certain ribonucleases or deoxyribonucleases) activity in a test sample, comprising: (a) selectively inactivating mammalian nucleases in a sample; (b) contacting the test sample with a substrate, thereby creating a test reaction mixture, wherein the substrate comprises a nucleic acid molecule comprising: (i) a cleavage domain comprising a single-stranded region, the single-stranded region of nucleic acid comprising a 2'-fluoro modified pyrimidine or 2'-O-methyl modified pyrimidine that renders the oligonucleotide resistant to degradation by mammalian nucleases; (ii) a fluorescence reporter group on one side of the internucleotide linkages; and iii. a non-fluorescent fluorescence-quenching group on the other side of the internucleotide linkages; (c) incubating the test reaction mixture for a time sufficient for cleavage of the substrate by a nuclease activity in the test sample; (d) determining whether a detectable fluorescence signal is emitted from the test reaction mixture; (e) contacting a control sample with the substrate, the control sample comprising a predetermined amount of nuclease, thereby creating a control reaction mixture; (f) incubating the control reaction mixture for a time sufficient for cleavage of the substrate by a nuclease in the control sample; and (g) determining whether a detectable fluorescence signal is emitted from the control reaction mixture; wherein detection of a greater fluorescence signal in the test reaction mixture than in the control reaction mixture indicates that the test sample contains greater nuclease activity than in the control sample, and wherein detection of a lesser fluorescence signal in the test reaction mixture than in the control reaction mixture indicates that the test sample contains less nuclease activity than in the control sample. In certain embodiments, the nucleic acid is RNA.

In certain embodiments, the present invention provides a method of detecting endonuclease (e.g., ribonuclease) activity in a test sample, comprising:

(a) contacting the test sample with a probe or substrate as described herein to form a digested probe, (b) collecting the digested probe, and (c) measuring the fluorescence emitted by the digested probe.

In certain embodiments, the test sample comprises a biological sample and calcium chloride. In certain embodiments, the biological sample is a blood sample. In certain embodiments, the blood sample is whole blood, serum or plasma. In certain embodiments, the blood sample is not subjected to a culturing step.

In certain embodiments, the calcium chloride is at a concentration of about 5 to 20 mM. In certain embodiments, the calcium chloride is at a concentration of about 10 mM.

In certain embodiments, the sample has been heated at 55-100° C. for 10 seconds to 20 hours to form a heat-treated test sample prior to testing. In certain embodiments, the sample has been heated at about 70 to 95° C. In certain embodiments, the sample has been heated for about 15-30 minutes. In certain embodiments, the sample has been heated at about 90° C. for about 20 minutes to form a heat-treated test sample prior to testing.

In certain embodiments, the sample has been clarified after the heating step. In certain embodiments, the clarification is by means of centrifugation at 1 k to 20 k×g for 10 seconds to 20 minutes after the heating step to form a heat-treated, clarified supernatant test sample. In certain embodiments, the clarification is by means of centrifugation at about 17 k×g for about 10 minutes after the heating step to form a heat-treated, clarified supernatant test sample. In certain embodiments, the clarification is by means of filtration after the heating step to form a heat-treated, clarified supernatant test sample.

In certain embodiments, an endonuclease (e.g, a ribonuclease) present in the heat-treated test sample has been concentrated prior to testing. In certain embodiments, the concentration is by means of an aptamer-mediated pulldown. In certain embodiments, the concentration is by means of immunoprecipitation. In certain embodiments, the immunoprecipitated endonuclease remains bound to an antibody used in the immunoprecipitation during contact with the probe. In certain embodiments, the immunoprecipitation is by means of anti-micrococcal nuclease antibody-coupled magnetic beads. In certain embodiments, the immunoprecipitation is specific for a particular microbe. In certain embodiments, the immunoprecipitation is by means of anti-micrococcal nuclease antibody-coupled magnetic beads. In certain embodiments, the magnetic beads are Protein G-coupled magnetic beads.

In certain embodiments, the fluorescence is measured at 485/530 nm excitation/emission.

In certain embodiments, the endonuclease is a *Staphylococcal aureus* endonuclease and the probe is NMTT.

In certain embodiments, the endonuclease is a *E. coli* endonuclease and the probe is CTACGTAG (SEQ ID NO:1) or CUACGUAG (SEQ ID NO:2).

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides "Operably-linked" refers to the association two chemical moieties so that the function of one is affected by the other, e.g., an arrangement of elements wherein the components so described are configured so as to perform their usual function.

BRIEF DESCRIPTION OF DRAWINGS

FIG. 4. Annealed configuration of self-complementary probes. Oligo 1 is depicted here (SEQ ID NO: 30). Note the complete self-complementarity that yields double-stranded nucleic acids. "FAM" indicates the position of the fluorescein amidite modification. "ZEN" and "RQ" indicate the positions of the ZEN and Iowa Black RQ fluorescence quenchers.

FIGS. 15A-15C. Rapid detection of *Mycoplasma*-associated nuclease activity with chemically modified RNAse substrates. The basis for nuclease detection with RNAse substrates is illustrated in panel A. RNA oligonucleotides (5'-UCUCGUACGUUC-3' (SEQ ID NO:6) purines in gray and pyrimidines in blue) with chemically modified nucleotides, labeled on the 5'-ends with FAM are not fluorescent due to the close proximity of a 3'-quencher to the FAM. Upon degradation of the oligo, the quencher diffuses away from the FAM and the FAM exhibits green fluorescence. *Mycoplasma*-associated nuclease activity is detected with various RNAse substrates (panel B). RNAse substrates with the chemically modified RNA compositions indicated were co-incubated with culture media conditioned by *Mycoplasma*-free or *Mycoplasma* contaminated HEK cells for 4 hours at 37° C. Fluorescence of these reactions was then measured with a fluorescence plate reader. Background fluorescence levels determined by the fluorescence level of each RNAse substrate incubated in serum-free unconditioned media have been subtracted from each experimental value. In panel C, the RNAse substrate with 2'-O-methyl-modified pyrimidines was incubated with the culture supernatant or a lysate prepared from material centrifuged from the supernatants of *Mycoplasma*-free or *Mycoplasma*-contaminated HEK cells. This assay was carried out as described for B, above, except that the incubation was for only 1 hour.

FIGS. 23A-F. Activation of the Cy5.5-TT probe by MN in vitro and in mice with MN-expressing S. aureus pyomyositis. For in vitro evaluation of the Cy5.5-TT nuclease-activated probe, serial dilutions of the probe were combined with DPBS or DPBS+1 U/µl MN in 100 µl volumes and incubated at 37° C. for 1 hour. Cy5.5 fluorescence was measured for each reaction in a 96-well plate in a Xenogen IVIS 200 imaging system. Controls include DPBS (left column) and the unquenched TT probe (second column) diluted in DPBS. To evaluate probe activation in mice with S. aureus-derived pyomyositis, uninfected mice (n=3 mice) (A), mice with lux+MN-expressing S. aureus (Newman strain) pyomyositis (n=4 mice) (C), and mice with lux+MN-negative S. aureus (Newman strain) pyomyositis (n=4 mice) (D) in the right thighs were imaged with Cy5.5-channel fluorescence (IVIS imaging system) prior to (Bkgd) and after tail vein administration of 3 nanomoles of Cy5.5-TT probe. Uninfected mice that received 3 nanomoles of unquenched TT probe (n=3 mice) (B) were imaged in the same manner, but with a shorter exposure time to avoid signal saturation. Luminescence images acquired prior to probe injections (see panels on left) indicate the location of the infections in C and D. Note probe activation adjacent to the infection site in C, and minimal probe activation adjacent to infection site in D. See lookup table signal display ranges (at right of luminescence and right-most fluorescence images) for the relationship between pseudocolors and signal strength. Fluorescence display levels are adjusted to show light levels that are above tissue autofluorescence, fluorescence produced by the unactivated TT probe or by bleed-through of the luminescence signal into the Cy5.5 channel. Time-points listed above fluorescence images indicate the time elapsed between probe administration and image acquisition. For imaging of probes in mice after sacrifice and dissection, mice with thigh-muscle lux+, MN-expressing S. aureus pyomyositis, injected with 3 nanomoles unquenched TT probe (n=4 mice) (E) or TT probe (n=4 mice) (F) were sacrificed 45 minutes after probe injection; organs and skin were removed and muscle tissue was imaged with luminescence and the Cy5.5 fluorescence channel. Note the lack of overlap between the probe fluorescence and bacteria-derived luminescence in E, indicating that the probe cannot access the infection site. The activated TT probe fluorescence is found adjacent to, but not co-localized with, the bacteria-derived luminescence (F). Lookup table signal display ranges of the pseudocolored luminescence and fluorescence image data are shown at right.

DETAILED DESCRIPTION OF THE INVENTION

Figure 1:
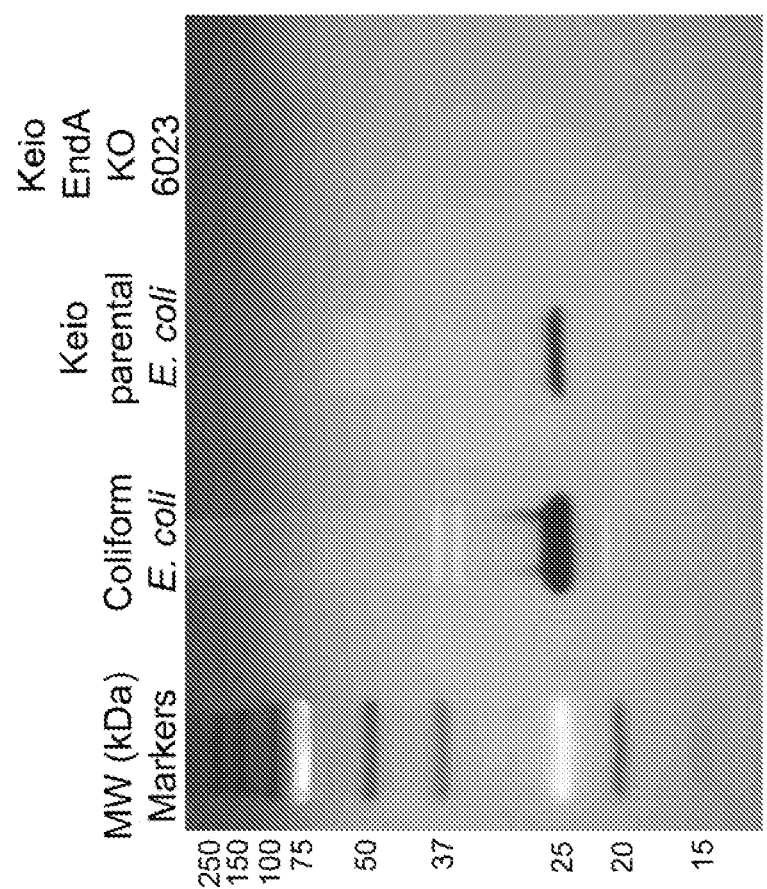
FIG. 1. DNA zymogram identifies Endonuclease 1 as a robust nuclease in a representative coliform *E. coli* strain. Lysates of the indicated *E. coli* strains were resolved with SDS-PAGE in which salmon sperm DNA was embedded in the gel matrix. The proteins were allowed to re-nature and the gel was then incubated at 37° C. to allow digestion. The gel was stained with SYBR Gold.

Close to 1 billion people currently depend on contaminated sources of water, a major underlying cause of diarrheal diseases which account for approximately 4% of disease burden globally (Connelly, J. T. & Baeumner, A. J. Biosensors for the detection of waterborne pathogens. *Anal Bioanal Chem* 402, 117-127 (2012)). Pathogenic microbial contaminants of drinking water include viruses, bacteria and parasites. The most common source of bacterial contamination of water supplies is animal and/or human feces. Current testing for fecal contamination depends on detection of "indicator" organisms, such as coliform *Escherichia coli* (*E. coli*), which are used because they are present in feces in great abundance and are thus easier to detect than many pathogens. Methods used for detecting coliform *E. coli* have a variety of limitations, including: 1) sensitivity for only a subset of *E. coli* strains, 2) time-intensive nature of the methods, 3) need for transport of water samples to appropriately equipped laboratories (Connelly, J. T. & Baeumner, A. J. Biosensors for the detection of waterborne pathogens. *Anal Bioanal Chem* 402, 117-127 (2012)). For instance, the Colilert® and Colisure® coliform *E. coli* detecting kits (of IDEXX Laboratories), which use traditional enzyme-detection methods for microbial detection, require 24-48 hours of culture and do not detect important pathogenic forms of *E. coli*, including the O157:H7 strain (Straub, T. M. & Chandler, D. P. Towards a unified system for detecting waterborne pathogens. *J Microbiol Methods* 53, 185-197 (2003)). PCR-based methods are capable of precise identification of bacterial species and strains present, but these methods are also time-consuming and require laboratories with appropriate technical infrastructure. Considering the limitations of existing technologies, a novel method that rapidly and specifically detects coliform *E. coli* in water samples in the field could be a disruptive technology in this market.

In certain embodiments, the present invention provides short oligonucleotide probes (Substrates) composed of chemically modified DNA or RNA flanked with at least one fluorophore on one end and at least one fluorescence quencher on the other end. Upon cleavage of the probes by nucleases (e.g., endonuclease), the fluorophore diffuses away from the quencher and exhibits fluorescence. These probes are not cleaved by mammalian nucleases, but are cleaved by nucleases produced by various bacteria, including pathogenic bacteria such as *Escherichia coli* (*E. coli*). The probes can thus be used to detect the presence of *E. coli* in biological samples such as blood serum, cell cultures, and food, and in vivo, and in environmental samples, such as water.

In certain embodiments, the present invention provides short oligonucleotide probes (Substrates) composed of chemically modified RNA flanked with a fluorophore on one end and a fluorescence quencher on the other end. Upon cleavage of the probes by nucleases (e.g., endonucleases, such as certain ribonucleases), the fluorophore diffuses away from the quencher and exhibits fluorescence. These probes are not cleaved by mammalian nucleases, but are cleaved by nucleases produced by various bacteria, including pathogenic bacteria such as *Staphylococcus aureus*, *Streptococcus pneumoniae* or *Mycoplasma*. The probes can thus be used to detect the presence of bacteria in biological samples such as blood serum, cell cultures, and food, and in vivo.

The present invention relates to methods for detecting nuclease (e.g., endonuclease) activity in a sample, comprising: 1) optionally, selectively inactivating mammalian nucleases in a sample and incubating a synthetic Substrate or mixture of Substrates in the sample, for a time sufficient for cleavage of the Substrates(s) by a nuclease enzyme, wherein the Substrate(s) comprises a single-stranded nucleic acid molecule containing at least one ribonucleotide or deoxyribonucleotide residue at an internal position that functions as a nuclease (e.g., endonuclease) cleavage site (and in certain embodiments a 2'-fluoro modified pyrimidine or 2'-O-methyl modified pyrimidine that renders the oligonucleotide resistant to degradation by mammalian nucleases), a fluorescence reporter group on one side of the cleavage sites, and a fluorescence-quenching group on the other side of the cleavage site, and 2) visual detection of a fluorescence signal, wherein detection of a fluorescence signal indicates that a nuclease (e.g., endonuclease) cleavage event has occurred, and, therefore, the sample contains nuclease (e.g., endonuclease) activity. The compositions of the invention are also compatible with other detection modalities (e.g., fluorometry).

The Substrate oligonucleotide of the invention comprises a fluorescent reporter group and a quencher group in such physical proximity that the fluorescence signal from the reporter group is suppressed by the quencher group. Cleavage of the Substrate with a nuclease (e.g., endonuclease) enzyme leads to strand cleavage and physical separation of the reporter group from the quencher group. Separation of reporter and quencher eliminates quenching, resulting in an increase in fluorescence emission from the reporter group. When the quencher is a so-called "dark quencher", the resulting fluorescence signal can be detected by direct visual inspection (provided the emitted light includes visible wavelengths). Cleavage of the Substrate compositions described in the present invention can also be detected by fluorometry.

In one embodiment, the synthetic Substrate is an oligonucleotide comprising ribonucleotide residues. The synthetic Substrate can also be a chimeric oligonucleotide comprising RNase-cleavable, e.g., RNA, residues, or modified RNase-resistant RNA residues. In certain embodiments, Substrate composition is such that cleavage is a ribonuclease-specific event and that cleavage by enzymes that are strictly deoxyribonucleases does not occur.

In one embodiment, the synthetic Substrate is a chimeric oligonucleotide comprising ribonucleotide residue(s) and modified ribonucleotide residue(s). In one embodiment, the synthetic Substrate is a chimeric oligonucleotide comprising ribonucleotide residues and 2'-O-methyl ribonucleotide residues. In one embodiment, the synthetic Substrate is a chimeric oligonucleotide comprising 2'-O-methyl ribonucleotide residues and one or more of each of the four ribonucleotide residues, adenosine, cytosine, guanosine, and uridine. Inclusion of the four distinct ribonucleotide bases in a single Substrate allows for detection of an increased spectrum of endonuclease enzyme activities by a single Substrate oligonucleotide.

In one embodiment, the synthetic Substrate is an oligonucleotide comprising deoxyribonucleotide residues. The synthetic Substrate can also be a chimeric oligonucleotide comprising DNase-cleavable, e.g., DNA, residues, or modified RNase-resistant RNA residues. Substrate composition is such that cleavage is a deoxyribonuclease-specific event and that cleavage by enzymes that are strictly ribonucleases does not occur.

In one embodiment, the synthetic Substrate is a chimeric oligonucleotide comprising deoxyribonucleotide residue(s) and modified ribonucleotide residue(s). In one embodiment, the synthetic Substrate is a chimeric oligonucleotide comprising deoxyribonucleotide residues and 2'-O-methyl ribonucleotide residues. In one embodiment, the synthetic Substrate is a chimeric oligonucleotide comprising 2'-O-methyl ribonucleotide residues and one or more of each of the four deoxyribonucleotide residues, deoxyadenosine, deoxycytosine, deoxyguanosine, and deoxythymidine. Inclusion of the four distinct deoxyribonucleotide bases in a single Substrate allows for detection of an increased spectrum of deoxyribonuclease enzyme activities by a single Substrate oligonucleotide.

To enable visual detection methods, the quenching group is itself not capable of fluorescence emission, being a "dark quencher". Use of a "dark quencher" eliminates the background fluorescence of the intact Substrate that would otherwise occur as a result of energy transfer from the reporter fluorophore. In one embodiment, the fluorescence quencher comprises dabcyl (4-(4'-dimethylaminophenylazo) benzoic acid). In one embodiment, the fluorescence quencher is comprised of QSY™-7 carboxylic acid, succinimidyl ester (N,N'-dimethyl-N,N'-diphenyl-4-((5-t-butoxycarbonylaminopentyl)aminocarbon yl) piperidinylsulfonerhodamine; a diarylrhodamine derivative from Molecular Probes, Eugene, Oreg.). Any suitable fluorophore may be used as reporter provided its spectral properties are favorable for use with the chosen quencher. A variety of fluorophores can be used as reporters, including but not limited to, fluorescein, tetrachlorofluorescein, hexachlorofluorescein, rhodamine, tetramethylrhodamine, Cy-dyes, Texas Red, Bodipy dyes, and Alexa dyes.

In certain embodiments, the method of the invention proceeds in multiple steps. In certain embodiments, mammalian nucleases are selectively inactivated in a sample. Next, the test sample is mixed with the Substrate reagent and incubated. Substrate can be mixed alone with the test sample or will be mixed with an appropriate buffer, e.g., one of a composition as described herein. Next, visual detection of fluorescence is performed. As fluorescence above background indicates fluorescence emission of the reaction product, i.e. the cleaved Substrate, detection of such fluorescence indicates that RNase activity is present in the test sample. The method provides that this step can be done with unassisted visual inspection. In particular, visual detection can be performed using a standard ultraviolet (UV) light source of the kind found in most molecular biology laboratories to provide fluorescence excitation. Substrates of the invention can also be utilized in assay formats in which detection of Substrate cleavage is done using a multi-well fluorescence plate reader or a tube fluorometer.

The present invention further features kits for detecting nuclease (e.g., endonuclease) activity comprising a Substrate nucleic acid(s) and instructions for use. Such kits may optionally contain one or more of: a positive control nuclease (e.g., endonuclease), RNase-free water, and a buffer. It is also provided that the kits may include RNase-free laboratory plasticware, for example, thin-walled, UV transparent microtubes for use with the visual detection method and/or multiwell plates for use with plate-fluorometer detection methods in a high-throughput format.

Accordingly, the present invention provides a method for detecting nuclease (e.g., endonuclease) activity in a test sample (optionally, in which mammalian nuclease will have been selectively inactivated in the sample), comprising: (a) contacting the test sample with a substrate, thereby creating a test reaction mixture, wherein the substrate comprises a nucleic acid molecule comprising (i) a cleavage domain comprising a single-stranded region, the single-stranded region comprising at least one internucleotide linkage (and in certain embodiments a 2'-fluoro modified pyrimidine or 2'-O-methyl modified pyrimidine that renders the oligonucleotide resistant to degradation by mammalian nucleases); (ii) a fluorescence reporter group on one side of the internucleotide linkage; and (iii) a non-fluorescent fluorescence-quenching group on the other side of the internucleotide linkage; (b) incubating the test reaction mixture for a time sufficient for cleavage of the substrate by a endonuclease in the sample; and (c) determining whether a detectable fluorescence signal is emitted from the test reaction mixture, wherein emission of a fluorescence signal from the reaction mixture indicates that the sample contains endonuclease activity.

While the methods of the invention can be practiced without the use of a control sample, in certain embodiments of the invention it is desirable to assay in parallel with the test sample a control sample comprising a known amount of RNase activity. Where the control sample is used as a negative control, the control sample, in some embodiments, contains no detectable RNase activity. Thus, the present invention further provides a method for detecting endonuclease activity in a test sample, comprising: (a) contacting the test sample with a substrate, thereby creating a test reaction mixture, wherein the substrate comprises a nucleic acid molecule comprising: (i) a cleavage domain comprising a single-stranded region, the single-stranded region comprising at least one internucleotide linkage (and in certain embodiments a 2'-fluoro modified pyrimidine or 2'-O-methyl modified pyrimidine that renders the oligonucleotide resistant to degradation by mammalian nucleases); (ii) a fluorescence reporter group on one side of the internucleotide linkage; and (iii) a non-fluorescent fluorescence-quenching group on the other side of the internucleotide linkage; (b) incubating the test reaction mixture for a time sufficient for cleavage of the substrate by a nuclease (e.g., endonuclease) activity in the test sample; (c) determining whether a detectable fluorescence signal is emitted from the test reaction mixture; (d) contacting a control sample with the substrate, the control sample comprising a predetermined amount of nuclease (e.g., endonuclease), thereby creating a control reaction mixture; (e) incubating the control reaction mixture for a time sufficient for cleavage of the substrate by a nuclease (e.g., endonuclease) in the control sample; (f) determining whether a detectable fluorescence signal is emitted from the control reaction mixture; wherein detection of a greater fluorescence signal in the test reaction mixture than in the control reaction mixture indicates that the test sample contains greater nuclease (e.g., endonuclease) activity than in the control sample, and wherein detection of a lesser fluorescence signal in the test reaction mixture than in the control reaction mixture indicates that the test sample contains less nuclease (e.g., endonuclease) activity than in the control sample. In one embodiment, the predetermined amount of nuclease (e.g., endonuclease) is no nuclease, such that detection of a greater fluorescence signal in the test reaction mixture than in the control reaction mixture indicates that the test sample contains nuclease (e.g., endonuclease) activity.

The methods of the invention can further entail contacting the test sample with a buffer before or during step (a).

The present invention further provides compositions and kits for practicing the present methods. Thus, in certain embodiments, the present invention provides a nucleic acid comprising: (a) a cleavage domain comprising a single-stranded region, the single-stranded region comprising at least one internucleotide linkage (and in certain embodiments a 2'-fluoro modified pyrimidine or 2'-O-methyl modified pyrimidine that renders the oligonucleotide resistant to degradation by mammalian nucleases); (b) a fluorescence reporter group on one side of the internucleotide linkage; and (c) a non-fluorescent fluorescence-quenching group on the other side of the internucleotide linkage. In other embodiments, the present invention provides a kit comprising: (a) in one container, a substrate, the substrate comprising a nucleic acid molecule comprising a single stranded region, the single-stranded region comprising: (i) a cleavage domain comprising a single-stranded region, the single-stranded region comprising at least one internucleotide linkage 3' to an adenosine residue, at least one internucleotide linkage 3' to a cytosine residue, at least one internucleotide linkage 3' to a guanosine residue, and at least one internucleotide linkage 3' to a uridine residue, and wherein the cleavage domain does not comprise a deoxyribonuclease-cleavable internucleotide linkage; (ii) a fluorescence reporter group on one side of the internucleotide linkages; and (iii) a non-fluorescent fluorescence-quenching group on the other side of the internucleotide linkages.

In one embodiment of the foregoing methods and compositions, the single stranded region of the cleavage domain comprises at least one internucleotide linkage 3' to an adenosine residue, at least one internucleotide linkage 3' to a cytosine residue, at least one internucleotide linkage 3' to a guanosine residue, and at least one internucleotide linkage 3' to a uridine residue. In one embodiment, the cleavage domain does not comprise a deoxyribonuclease-cleavable internucleotide linkage. In yet another referred embodiment, the single stranded region of the cleavage domain comprises at least on internucleotide linkage 3' to an adenosine residue, at least one internucleotide linkage 3' to a cytosine residue, at least one internucleotide linkage 3' to a guanosine residue, and at least one internucleotide linkage 3' to a uridine residue and the cleavage domain does not comprise a deoxyribonuclease-cleavable internucleotide linkage.

In one embodiment of the foregoing methods and compositions, the single stranded region of the cleavage domain comprises at least one internucleotide linkage 3' to a deoxyadenosine residue, at least one internucleotide linkage 3' to a deoxycytosine residue, at least one internucleotide linkage 3' to a deoxyguanosine residue, and at least one internucleotide linkage 3' to a deoxythymidine residue. In one embodiment, the cleavage domain does not comprise a ribonuclease-cleavable internucleotide linkage. In yet another referred embodiment, the single stranded region of the cleavage domain comprises at least one internucleotide linkage 3" to a deoxyadenosine residue, at least one internucleotide linkage 3' to a deoxycytosine residue, at least one internucleotide linkage 3' to a deoxyguanosine residue, and at least one internucleotide linkage 3' to a deoxythymidine residue and the cleavage domain does not comprise a ribonuclease-cleavable internucleotide linkage.

With respect to the fluorescence quenching group, any compound that is a dark quencher can be used in the methods and compositions of the invention. Numerous compounds are capable of fluorescence quenching, many of which are not themselves fluorescent (i.e., are dark quenchers.) In one embodiment, the fluorescence-quenching group is a nitrogen-substituted xanthene compound, a substituted 4-(phenyldiazenyl)phenylamine compound, or a substituted 4-(phenyldiazenyl)naphthylamine compound. In certain specific modes of the embodiment, the fluorescence-quenching group is 4-(4'-dimethylaminophenylazo)benzoic acid), N,N'-dimethyl-N,N'-diphenyl-4-((5-t-butoxycarbonylaminopentyl) aminocarbonyl) piperidinylsulfonerhodamine (sold as QSY-7™ by Molecular Probes, Eugene, Oreg.), 4',5'-dinitrofluorescein, pipecolic acid amide (sold as QSY-33™ by Molecular Probes, Eugene, Oreg.) 4-[4-nitrophenyldiazinyl]phenylamine, or 4-[4-nitrophenyldiazinyl]naphthylamine (sold by Epoch Biosciences, Bothell, Wash.). In other specific modes of the embodiment, the fluorescence-quenching group is Black-Hole Quenchers™ 1, 2, or 3 (Biosearch Technologies, Inc.).

In certain embodiments, the fluorescence reporter group is fluorescein, tetrachlorofluorescein, hexachlorofluorescein, rhodamine, tetramethylrhodamine, a Cy dye, Texas Red, a Bodipy dye, or an Alexa dye.

With respect to the foregoing methods and compositions, the fluorescence reporter group or the fluorescence quenching group can be, but is not necessarily, attached to the 5'-terminal nucleotide of the substrate.

The nucleic acids of the invention, including those for use as substrates in the methods of the invention, in certain embodiments are single-stranded RNA molecule. In other embodiments, the nucleic acids of the invention are chimeric oligonucleotides comprising a nuclease resistant modified ribonucleotide residue. Exemplary RNase resistant modified ribonucleotide residues include 2'-O-methyl ribonucleotides, 2'-methoxyethoxy ribonucleotides, 2'-O-allyl ribonucleotides, 2'-O-pentyl ribonucleotides, and 2'-O-butyl ribonucleotides. In one mode of the embodiment, the modified ribonucleotide residue is at the 5'-terminus or the 3'-terminus of the cleavage domain. In yet other embodiments, the nucleic acids of the invention are chimeric oligonucleotides comprising a deoxyribonuclease resistant modified deoxyribonucleotide residue. In specific modes of the embodiments, the deoxyribonuclease resistant modified deoxyribonucleotide residue is a phosphotriester deoxyribonucleotide, a methylphosphonate deoxyribonucleotide, a phosphoramidate deoxyribonucleotide, a phosphorothioate deoxyribonucleotide, a phosphorodithioate deoxyribonucleotide, or a boranophosphate deoxyribonucleotide. In yet other embodiments of the invention, the nucleic acids of the invention comprise a ribonuclease-cleavable modified ribonucleotide residue.

The nucleic acids of the invention, including those for use as substrates in the methods of the invention, are at least 3 nucleotides in length, such as 5-30 nucleotides in length. In certain specific embodiments, the nucleic acids of the invention are 5-20, 5-15, 5-10, 7-20, 7-15 or 7-10 nucleotides in length.

In certain embodiments, the fluorescence-quenching group of the nucleic acids of the invention is 5' to the cleavage domain and the fluorescence reporter group is 3' to the cleavage domain. In a specific embodiment, the fluorescence-quenching group is at the 5' terminus of the substrate. In another specific embodiment, the fluorescence reporter group is at the 3' terminus of the substrate.

In certain embodiments, the fluorescence reporter group of the nucleic acids of the invention is 5' to the cleavage domain and the fluorescence-quenching group is 3' to the cleavage domain. In a specific embodiment, the fluorescence reporter group is at the 5' terminus of the substrate. In another specific embodiment, the fluorescence-quenching group is at the 3' terminus of the substrate.

In one embodiment of the invention, a nucleic acid of the invention comprising the formula: 5'-$N_1$-n-$N_2$-3', wherein: (a) "$N_1$" represents zero to five 2'-modified ribonucleotide residues; (b) "$N_2$" represents one to five 2'-modified ribonucleotide residues; and (c) "n" represents one to ten, such as four to ten unmodified ribonucleotide residues. In a certain specific embodiment, "$N_1$" represents one to five 2'-modified ribonucleotide residues. In certain modes of the embodiment, the fluorescence-quenching group or the fluorescent reporter group is attached to the 5'-terminal 2'-modified ribonucleotide residue of $N_1$.

In the nucleic acids of the invention, including nucleic acids with the formula: 5'-$N_1$-n-$N_2$-3', the fluorescence-quenching group can be 5' to the cleavage domain and the fluorescence reporter group is 3' to the cleavage domain;

alternatively, the fluorescence reporter group is 5' to the cleavage domain and the fluorescence-quenching group is 3' to the cleavage domain.

With respect to the kits of the invention, in addition to comprising a nucleic acid of the invention, the kits can further comprise one or more of the following: an endonuclease (e.g, a ribonuclease); endonuclease-free water (e.g., ribonuclease-free water), a buffer, and endonuclease-free laboratory plasticware (e.g., ribonuclease-free laboratory plasticware).

"Probe" or "Substrate" Oligonucleotides

Compositions of the invention comprise synthetic oligonucleotide Substrates that are substrates for nuclease (e.g., endonuclease) enzymes. Substrate oligonucleotides of the invention comprise: 1) one or more nuclease-cleavable bases, e.g., RNA bases, some or all of which function as scissile linkages, 2) a fluorescence-reporter group and a fluorescence-quencher group (in a combination and proximity that permits visual FRET-based fluorescence quenching detection methods), and 3) may optionally contain RNase-resistant modified RNA bases, nuclease-resistant DNA bases, or unmodified DNA bases. Synthetic oligonucleotide RNA-DNA chimeras wherein the internal RNA bonds function as a scissile linkage are described in U.S. Pat. Nos. 6,773,885 and 7,803,536. The fluorescence-reporter group and the fluorescence-quencher group are separated by at least one RNAse-cleavable residue, e.g., RNA base. Such residues serve as a cleavage domain for endonucleases (e.g, ribonucleases).

In certain embodiments, the substrate oligonucleotide probes are single-stranded or double-stranded oligoribonucleotides. In certain embodiments, the oligonucleotide probes are composed of modified oligoribonucleotides. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2-azido-ribose, carbocyclic sugar analogues a-anomeric sugars; epimeric sugars such as arabinose, xyloses or lyxoses, pyranose sugars, furanose sugars, and sedoheptulose. In certain embodiments, the Substrate includes, but is not limited to, 2'-O-methyl RNA, 2'-methoxyethoxy RNA, 2'-O-allyl RNA, 2'-O-pentyl RNA, and 2'-O-butyl RNA. In certain embodiments, the substrate is an RNA-2'-O-methyl RNA oligonucleotide having the general structure 5' r-NnN-q 3', where 'N' represents from about one to five 2'-modified ribonucleotide residues, 'n' represents one to ten unmodified ribonucleotide residues, 'r' represents a fluorescence reporter group, and 'q' represents a fluorescence quencher group. The 5'- and 3'-position of reporter and quencher are interchangeable. In one embodiment, the fluorescence reporter group and the fluorescence quencher group are positioned at or near opposing ends of the molecule. It is not important which group is placed at or near the 5'-end versus the 3'-end. It is not required that the reporter and quencher groups be end modifications, however positioning these groups at termini simplifies manufacture of the Substrate. The fluorescence reporter group and the fluorescence quencher group may also be positioned internally so long as an RNA scissile linkage lies between reporter and quencher.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2-methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine.

The oligonucleotides of the invention are synthesized using conventional phosphodiester linked nucleotides and synthesized using standard solid or solution phase synthesis techniques which are known in the art. Linkages between nucleotides may use alternative linking molecules. For example, linking groups of the formula P(O)S, (thioate); P(S)S, (dithioate); P(O)NR'2; P(O)R; P(O)OR6; CO; or CONR'2 wherein R is H (or a salt) or alkyl (1-12C) and R6 is alkyl (1-9C) is joined to adjacent nucleotides through —O— or —S—.

In certain embodiments of the present invention, the oligonucleotides have additional modifications, such as 2'O-methyl modification of the pyrimidines. In other embodiments, all of the nucleotides in the oligonucleotides are 2'O-methyl modified. Alternatively, the pyrimidines, or all the nucleotides, may be modified with 2'-fluoros (both pyrimidines and purines).

The oligonucleotides are short, such as between 2-30 nucleotides in length (or any value in between). In certain embodiments, that oligonucleotide is between 8-15 nucleotides in length. In certain embodiments, that oligonucleotide is between 11-13 nucleotides in length. In general, shorter sequences will give better signal to noise ratios than longer probes and will therefore be more sensitive. However, in certain embodiments, shorter probes might not be the best substrate for the nuclease, so some degree of empiric optimization for length is needed. In certain embodiments, the oligonucleotide comprises 0-50% purines (or any value in between). In certain embodiments the oligonucleotide comprises 100% pyrimidines.

It should be noted that the specific sequence of the oligonucleotide is not critical. Certain combinations of purines and pyrimidines are susceptible to bacterial endonucleases, while resisting mammalian nucleases. Endonucleases are enzymes that cleave the phosphodiester bond within a polynucleotide chain, in contrast to exonucleases, which cleave phosphodiester bonds at the end of a polynucleotide chain. These bacterial nucleases are not sequence-specific like restriction enzymes, which typically require a recognition site and a cleavage pattern. Some endonucleases cleave single-stranded nucleic acid molecules, while others cleave double-stranded nucleic acid molecules. For example, the data below show a time-course of activity of the *Mycoplasma*-derived nuclease and demonstrate that the *Mycoplasma* nuclease can digest a variety of distinct sequences. The earliest time-point shows partial degradation of the 51 nt long sequence modified with either 2'-fluoro or 2'-O-methyl pyrimidines, with intermediate degradation products clearly visible. Each of the degradation products of intermediate size is in fact a distinct substrate and these are clearly being digested as seen in the later time points.

Fluorophores

In certain embodiments, the oligonucleotides of the present invention are operably linked to one or more fluorophores, which may also be called a "fluorescent tag." A fluorophore is a molecule that absorbs light (i.e. excites) at a characteristic wavelength and emits light (i.e. fluoresces) at a second lower-energy wavelength. Fluorescence reporter groups that can be incorporated into Substrate compositions include, but are not limited to, fluorescein, tetrachlorofluorescein, hexachlorofluorescein, tetramethylrhodamine, rhodamine, cyanine-derivative dyes, Texas Red, Bodipy, and Alexa dyes. Characteristic absorption and emission wavelengths for each of these are well known to those of skill in the art.

A fluorescence quencher is a molecule that absorbs or releases energy from an excited fluorophore (i.e., reporter), returning the fluorophore to a lower energy state without fluorescence emission at the wavelength characteristic of that fluorophore. For quenching to occur, reporter and quencher must be in physical proximity. When reporter and quencher are separated, energy absorbed by the reporter is no longer transferred to the quencher and is instead emitted as light at the wavelength characteristic of the reporter. Appearance of a fluorescent signal from the reporter group following removal of quenching is a detectable event and constitutes a "positive signal" in the assay of the present invention, and indicates the presence of RNase in a sample.

Fluorescence quencher groups include molecules that do not emit any fluorescence signal ("dark quenchers") as well as molecules that are themselves fluorophores ("fluorescent quenchers"). Substrate compositions that employ a "fluorescent quencher" will emit light both in the intact and cleaved states. In the intact state, energy captured by the reporter is transferred to the quencher via FRET and is emitted as light at a wavelength characteristic for the fluorescent quencher. In the cleaved state, energy captured by the reporter is emitted as light at a wavelength characteristic for the reporter. When compositions that employ fluorescent quenchers are used in a FRET assay, detection must be done using a fluorometer. In certain embodiments, Substrate compositions that employ a "dark quencher" will emit light only in the cleaved state, enabling signal detection to be performed visually (detection may also be done using a fluorometer). Visual detection is rapid, convenient, and does not require the availability of any specialized equipment. It is desirable for an RNase detection assay to have visual detection method as an available option. Substrate compositions employing a "dark quencher" enable a visual detection endonuclease assay while Substrate compositions employing a "fluorescent quencher" are incompatible with a visual detection assay.

In one embodiment of the invention, the Substrate is comprised of a fluorescence quencher group that does not itself emit a fluorescence signal, i.e. is a "dark quencher". "Dark quenchers" useful in compositions of the invention include, but are not limited to, dabcyl, QSY™-7, QSY-33 (4',5-dinitrofluorescein, pipecolic acid amide) and Black-Hole Quenchers™ 1, 2, and 3 (Biosearch Technologies, Novato, Calif.). Assay results (i.e., signal from cleaved Substrate) can thus be detected visually. Optionally, the fluorescence signal can be detected using a fluorometer or any other device capable of detecting fluorescent light emission in a quantitative or qualitative fashion.

In certain embodiments, the fluorophore is one or more of the fluorophores listed in Table 1.

TABLE 1

| Probe | Excitation (nm) | Emission (nm) |
|---|---|---|
| Hydroxycoumarin | 325 | 386 |
| Alexa fluor | 325 | 442 |
| Aminocoumarin | 350 | 445 |
| Methoxycoumarin | 360 | 410 |
| Cascade Blue | (375); 401 | 423 |
| Pacific Blue | 403 | 455 |
| Pacific Orange | 403 | 551 |
| Lucifer yellow | 425 | 528 |
| Alexa fluor 430 | 430 | 545 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| Red 613 | 480; 565 | 613 |
| PerCP | 490 | 675 |
| Cy2 | 490 | 510 |
| TruRed | 490, 675 | 695 |
| FluorX | 494 | 520 |
| Fluorescein | 495 | 519 |
| FAM | 495 | 515 |
| BODIPY-FL | 503 | 512 |
| TET | 526 | 540 |
| Alexa fluor 532 | 530 | 555 |
| HEX | 535 | 555 |
| TRITC | 547 | 572 |
| Cy3 | 550 | 570 |
| TMR | 555 | 575 |
| Alexa fluor 546 | 556 | 573 |
| Alexa fluor 555 | 556 | 573 |
| Tamara | 565 | 580 |
| X-Rhodamine | 570 | 576 |
| Lissamine Rhodamine B | 570 | 590 |
| ROX | 575 | 605 |
| Alexa fluor 568 | 578 | 603 |
| Cy3.5 581 | 581 | 596 |
| Texas Red | 589 | 615 |
| Alexa fluor 594 | 590 | 617 |
| Alexa fluor 633 | 621 | 639 |
| LC red 640 | 625 | 640 |
| Allophycocyanin (APC) | 650 | 660 |
| Alexa fluor 633 | 650 | 688 |
| APC-Cy7 conjugates | 650; 755 | 767 |
| Cy5 | 650 | 670 |
| Alexa fluor 660 | 663 | 690 |
| Cy5.5 | 675 | 694 |
| LC red 705 | 680 | 710 |
| Alexa fluor 680 | 679 | 702 |
| Cy7 | 743 | 770 |
| IRDye 800 CW | 774 | 789 |

In certain in vivo embodiments, the fluorophore emits in the near infrared range, such as in the 650-900 nm range. (Weissleder et al., "Shedding light onto live molecular targets, *Nature Medicine,* 9:123-128 (2003)).

Fluorescence Quencher Group

In certain embodiments, the oligonucleotides of the present invention are operably linked to one or more fluorescence quencher group or "quencher."

In certain embodiments, the quencher is one or more of the quenchers listed in Table 2.

TABLE 2

| Quencher | Absorption Maximum (nm) |
|---|---|
| DDQ-I | 430 |
| Dabcyl | 475 |
| Eclipse | 530 |
| Iowa Black FQ | 532 |

TABLE 2-continued

| Quencher | Absorption Maximum (nm) |
|---|---|
| BHQ-1 | 534 |
| QSY-7 | 571 |
| BHQ-2 | 580 |
| DDQ-II | 630 |
| Iowa Black RQ | 645 |
| QSY-21 | 660 |
| BHQ-3 | 670 |
| IRDye QC-1 | 737 |
| ZEN | 532 |

Additional quenchers are described in U.S. Pat. No. 7,439,341, which is incorporated by reference herein.

Linkers

In certain embodiments, the oligonucleotide is linked to the fluorophore and/or quencher by means of a linker.

In certain embodiments, an aliphatic or ethylene glycol linker (as are well known to those will skill in the art) is used. In certain embodiments, the linker is a phosphodiester linkage. In certain embodiments, the linker is a phosphorothioate linkage. In certain embodiments, other modified linkages between the modifier groups like dyes and quencher and the bases are used in order to make these linkages more stabile, thereby limiting degradation to the nucleases.

In certain embodiments, the linker is a binding pair. In certain embodiments, the "binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate, IgG-protein A, antigen-antibody, and the like. In certain embodiments, a first member of the binding pair comprises avidin or streptavidin and a second member of the binding pair comprises biotin.

In certain embodiments, the oligonucleotide is linked to the fluorophore and/or quencher by means of a covalent bond.

In certain embodiments, the oligonucleotide probe, i.e., an oligonucleotide that is operably linked to a fluorophore and quencher, is also operably linked to a solid substrate. For example, the oligonucleotide probe may be linked to a magnetic bead.

Chemistries that can be used to link the fluorophores and quencher to the oligonucleotide are known in the art, such as disulfide linkages, amino linkages, covalent linkages, etc. In certain embodiments, aliphatic or ethylene glycol linkers that are well known to those with skill in the art can be used. In certain embodiments, phosphodiester, phosphorothioate and/or other modified linkages between the modifier groups like dyes and quencher are used. These linkages provide stability to the probes, thereby limiting degradation to nucleobases. Additional linkages and modifications can be found on the world-wide-web at trilinkbiotech.com/products/oligo/oligo_modifications.asp.

Detection Compositions

In certain embodiments, the probes described above can be prepared as pharmaceutically-acceptable compositions. In certain embodiments, the probes are administered so as to result in the detection of a microbial infection. The amount administered will vary depending on various factors including, but not limited to, the composition chosen, the particular disease, the weight, the physical condition, and the age of the mammal. Such factors can be readily determined by the clinician employing animal models or other test systems, which are well known to the art.

Pharmaceutical formulations, dosages and routes of administration for nucleic acids are generally known in the art. The present invention envisions detecting a microbial infection in a mammal by the administration of a probe of the invention. Both local and systemic administration is contemplated.

One or more suitable unit dosage forms of the probe of the invention can be administered by a variety of routes including parenteral, including by intravenous and intramuscular routes, as well as by direct injection into the diseased tissue. The formulations may, where appropriate, be conveniently presented in discrete unit dosage forms and may be prepared by any of the methods well known to pharmacy. Such methods may include the step of bringing into association the probe with liquid carriers, solid matrices, semi-solid carriers, finely divided solid carriers or combinations thereof, and then, if necessary, introducing or shaping the product into the desired delivery system.

When the probes of the invention are prepared for administration, in certain embodiments they are combined with a pharmaceutically acceptable carrier, diluent or excipient to form a pharmaceutical formulation, or unit dosage form. The total active ingredient (i.e., probe) in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the probe of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of probe of the invention can also take the form of an aqueous or anhydrous solution or dispersion, or alternatively the form of an emulsion or suspension.

Thus, probe may be formulated for parenteral administration (e.g., by injection, for example, bolus injection or continuous infusion) and may be presented in unit dose form in ampules, pre-filled syringes, small volume infusion containers or in multi-dose containers with an added preservative. The probe may take such forms as suspensions, solutions, or emulsions in oily or aqueous vehicles, and may contain formulatory agents such as suspending, stabilizing and/or dispersing agents. Alternatively, the probe may be in powder form, obtained by aseptic isolation of sterile solid or by lyophilization from solution, for constitution with a suitable vehicle, e.g., sterile, pyrogen-free water, before use.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0, saline solutions, and water.

Substrate Synthesis

Synthesis of the nucleic acid Substrate of the invention can be performed using solid-phase phosphoramidite chemistry (U.S. Pat. No. 6,773,885) with automated synthesizers, although other methods of nucleic acid synthesis (e.g., the H-phosphonate method) may be used. Chemical synthesis of nucleic acids allows for the production of various forms of the nucleic acids with modified linkages, chimeric compositions, and nonstandard bases or modifying groups attached in chosen places throughout the nucleic acid's entire length.

Detectable Bacteria

The following bacteria can be detected using the methods of the present invention:

*Staphylococcus aureus*
*Staphylococcus epidermidis*
*Staphylococcus lugdunensis*
*Staphylococcus saprophyticus*
*Streptococcus pyogenes*
*Streptococcus agalactiae*
*Streptococcus pneumoniae*
*Streptococcus mutans*
*Listeria monocytogenes*
*Corynebacterium diphtheriae*
*Bordetella pertussis*
*Clostridium difficile*
*Clostridium perfringens*
*Clostridium botulinum*
*Enterobacter cloacae*
*Citrobacter freundii*
*Borrelia burgdorferi*
*Treponema pallidum*
*Bacillus anthracis*
*Bacillus cereus*
*Enterococcus faecalis*
*Enterococcus faecium*
*Pseudomonas aeruginosa*
*Acinetobacter baumannii*
*Yersinia pestis*
*Yersinia pseudotuberculosis*
*Yersinia enterocolitica*
*Klebsiella pneumoniae*
*Vibrio cholerae*
*Salmonella enterica*
*Salmonella typhi*
*Escherichia coli*
*Neisseria gonorrhoeae*
*Neisseria meningitidis*
*Mycobacterium tuberculosis*
*Haemophilus influenzae*
*Legionella pneumophila*
*Francisella tularensis*
*Bacteroides fragilis*
*Brucella abortus*
*Mycoplasma fermentans*
*Mycoplasma pneumoniae*
*Mycoplasma genitalium*
*Chlamydia trachomatis*

Detectable Viruses

In addition to the bacterial pathogens listed above, the present invention can also detect human Cytomegalovirus (CMV, also known as Human Herpes Virus 5). It also detects related viruses which include Human Herpes Viruses 1, 2, 3, 4, 5, 6A, 6B, 7 and 8.

Detection Methods

In certain embodiments, the present invention provides methods for detecting bacteria in a sample in vitro or in vivo. The method of the invention proceeds in the following steps: combine "test sample" with Substrate(s) to produce a mixture, the mixture being the Assay Mix, incubate, and detect fluorescence signal. "Test sample" refers to any material being assayed for endonuclease (e.g., ribonuclease) activity and in certain embodiments, will be a liquid. Solids can be indirectly tested for the presence of RNase contamination by washing or immersion in solvent, e.g., water, followed by assay of the solvent.

For example, one can contact a sample with an oligonucleotide probe as described herein, and detect the presence of bacterial endonucleases using a florometer. Alternatively, oligonucleotide probes or compositions can be administered in vivo to a patient (e.g. injected in situ into a mammal) and fluorescence in the organism can be measured. In certain embodiments, the in vivo fluorescence can be measured to a depth of about 7-14 cm. Thus, in certain embodiments, the probes of the present invention can be use in medical diagnostic applications and medical diagnostic imaging.

In certain embodiments, the probes of the present invention are also useful to detect bacterial contamination in settings such as research laboratories.

Assay Mix.

The Substrate is mixed and incubated with the test sample. This mixture constitutes the Assay Mix. Ideally, the Assay Mix is a small volume, from about 1 µl to about 10 mls, or, from about 10 to 100 µl. The precise volume of the Assay Mix will vary with the nature of the test sample and the detection method. Optionally, a buffer can be added to the Assay Mix. Nucleases, including some ribonucleases, require the presence of divalent cations for maximum activity and providing an optimized buffered solution can increase the reaction rate and thereby increase assay sensitivity. Buffers of different composition can be used, as described in U.S. Pat. No. 6,773,885. In certain embodiments, control reactions are included, but are not essential. A Negative Control Mix, for example, comprises a solution of Substrate in water or buffer without any test sample or added nuclease. In this control, the Substrate should remain intact (i.e., without fluorescence emission). If the Negative Control Mix results in positive signal, then the quality of all reagents is suspect and fresh reagents should be employed. Possible causes of a signal in a Negative Control include degradation of the Substrate or contamination of any component reagent with endonuclease (e.g., ribonuclease) activity. A Positive Control Mix, for example, comprises a solution of Substrate in water or buffer plus a known, active RNase enzyme. If the Positive Control Mix results in a negative signal, then the quality of all reagents is suspect and fresh reagents should be employed. Possible causes of a negative Positive Control Mix include defective Substrate or contamination of any component reagent with an endonuclease (e.g., a ribonuclease) inhibitor. Any RNase that cleaves the Substrate can be employed for use in the Positive Control Mix. In one embodiment, RNase A is used, as this enzyme is both inexpensive and readily available. Alternatively, RNase 1 can be used. RNase 1 is heat labile and is more readily decontaminated from laboratory surfaces.

Incubation.

The Assay Mix (e.g., the test sample plus Substrate) is incubated. Incubation time and condition can vary from a few minutes to 24 hours or longer depending upon the sensitivity required. Incubation times of one hour or less are desirable. Endonucleases (e.g., ribonucleases) are catalytic. Increasing incubation time should therefore increase sensitivity of the Assay, provided that background cleavage of the Substrate (hydrolysis) remains low. As is evident, assay background is stable over time and Assay sensitivity increases with time of incubation. Incubation temperature can generally vary from room temperature to 37.degree. C. but may be adjusted to the temperature optimum of a specific endonuclease (e.g., ribonuclease) suspected as being present as a contaminant.

Signal Detection.

Fluorescence emission can be detected using a number of techniques (U.S. Pat. No. 6,773,885). In one method of detection, visual inspection is utilized. Visual detection is rapid, simple, and can be done without need of any specialized equipment. Alternatively, detection can be done using fluorometry or any other method that allows for qualitative or quantitative assessment of fluorescent emission.

Visual Detection Method.

Following incubation, the Assay Mix is exposed to UV light to provide excitation of the fluorescence reporter group. An Assay Mix in which the Substrate remains intact will not emit fluorescent signal and will visually appear clear or dark. Absence of fluorescence signal constitutes a negative assay result. An Assay Mix in which the Substrate has been cleaved will emit fluorescent signal and will visually appear bright. Presence of fluorescence signal constitutes a positive assay result, and indicates the presence of RNase activity in the sample. The visual detection method is primarily intended for use as a qualitative endonuclease (e.g., ribonuclease) assay, with results being simply either "positive" or "negative". However, the assay is crudely quantitative in that a bright fluorescent signal indicates higher levels of RNase contamination than a weak fluorescent signal.

The Assay Mix will ideally constitute a relatively small volume, for example 10 to 100 μl, although greater or lesser volumes can be employed. Small volumes allow for maintaining high concentrations of Substrate yet conserves use of Substrate. The visual detection Assay in one embodiment uses 50 pmoles of Substrate at a concentration of 0.5 μM in a 100 μl final volume Assay Mix. Lower concentration of Substrate (e.g., below 0.1 uM) will decrease assay sensitivity. Higher concentrations of Substrate (e.g., above 1 μM) will increase background and will unnecessarily consume Substrate.

Steps (mixing, incubating, detecting), can be performed in one tube. In one embodiment, the tube is a small, thin-walled, UV transparent microfuge tube, although tubes of other configuration may be used. A "short wave" UV light source emitting at or around 254 nm is used in one embodiment for fluorescence excitation. A "long wave" UV light source emitting at or around 300 nm can also be employed. A high intensity, short wave UV light source will provide for best sensitivity. UV light sources of this kind are commonly found in most molecular biology laboratories. Visual detection can be performed at the laboratory bench or in the field, however sensitivity will be improved if done in the dark.

Fluorometric Detection Method.

Following incubation fluorescence emission can be detected using a fluorometer. Fluorometric detection equipment includes, but is not limited to, single sample cuvette devices and multiwell plate readers. As before, mixing, incubation, and detection can be performed in the same vessel. Use of a multiwell plate format allows for small sample volumes, such as 200 μl or less, and high-throughput robotic processing of many samples at once. This format is used in certain industrial QC settings. The method also provides for the Assay to be performed in RNase free cuvettes. As before, mixing, incubation, and detection can be performed in the same vessel. Use of fluorometric detection allows for highly sensitive and quantitative detection.

Kits

The present invention further includes kits for detecting endonuclease (e.g., ribonuclease) activity in a sample, comprising Substrate nucleic acid(s) and instructions for use. Such kits may optionally contain one or more of: a positive control endonuclease (e.g., ribonuclease), RNase-free water, a buffer, and other reagents. The kits may include RNase-free laboratory plasticware, such as thin-walled, UV transparent microtubes and/or multiwell plates for use with the visual detection method and multiwell plates for use with plate-fluorometer detection methods.

One kit of the invention includes a universal Substrate, the Substrate being sensitive to a broad spectrum of endonuclease (e.g., ribonuclease) activity. The kit is intended to detect endonuclease (e.g., ribonuclease) activity from a variety of sources. The assay is compatible with visual detection. In certain embodiments, the Substrate will be provided in dry form in individual thin-walled, UV transparent microtubes, or in multiwell (e.g., 96 well) formats suitable for high throughput procedures. Lyophilized Substrate has improved long-term stability compared to liquid solution in water or buffer. If provided in liquid solution, stability is improved with storage at least below −20° C., such as at −80° C. Storage in individual aliquots limits potential for contamination with environmental endonuclease (e.g., ribonucleases). Alternatively, the Substrate can be provided in bulk, either lyophilized or in liquid solution. Alternatively, substrate can be provided in bulk and can be dispersed at the discretion of the user.

An additional kit of the invention includes a set of enzyme-specific or enzyme-selective Substrates that together detect most RNase activities and individually can be used to distinguish between different endonuclease (e.g., ribonuclease) enzymes. Such a kit can be used to assess the nature and source of RNase contamination or can measure activity of specific enzyme of interest.

In Vitro Assays for Evaluating Nuclease Activity

In certain embodiments, the present invention provides in vitro assays for evaluating the activity of microbial nucleases on various nucleic acid substrates. In certain embodiments the assay evaluates the activity of *Mycoplasma* nucleases. In certain embodiments the assay evaluates the activity of bacterial (e.g., *Staphylococcus aureus* or *Streptococcus pneumonia*) or viral nucleases. For example, a biological sample (e.g., tissue, cells, biological fluids) or material derived from such a sample is combined with an oligonucleotide-based probe and incubated for a period to time. The fluorescence level of this reaction is then measured (e.g., with a fluorometer), and compared with the fluorescence levels of similar reactions that serve as positive and negative controls.

Selective Inactivation of Serum Nucleases in Serum and Plasma Samples Containing Micrococcal Nuclease.

To selectively inactivate mammalian (mouse or human) serum nucleases, while preserving the activity of micrococcal nuclease, we have developed a simple heat-based protocol that denatures and inactivates the mammalian nucleases. Micrococcal nuclease is known to re-fold into its natural conformation after heat-denaturation in buffers containing sufficient concentrations of calcium and proteins. The survival of serum nucleases subjected to these same conditions has not, to the best of our knowledge, been studied. After dialyzing mouse or human serum (or human plasma) that was spiked with varying concentrations of micrococcal nuclease against a buffer of 50 mM Tris-HCl, pH 9.0, 10 mM CaCl2, the samples were incubated at 90° C. for 20 minutes. The samples were then allowed to cool to room temperature, centrifuged in a microcentrifuge to pellet the proteins that had aggregated and the supernatants were transferred to fresh tubes. 9 microliters of each supernatant was then combined with 50 picomoles of the Poly TT Probe in a 10 microliter reaction and incubated at 37° C. for 1 hour. Each reaction was then diluted in a "stop" buffer (290 uL of 10 mM EDTA+10 mM EGTA in PBS) and divided into 3 portions for triplicate plate-reader fluorescence measurements. The nuclease activity of serum samples in which micrococcal nuclease was not added was close to background levels (i.e., levels observed when probe is incubated with buffer only). The samples in which even very small amounts of micrococcal nuclease were added exhibited strong nuclease activity against this probe after this protocol was carried out. This method may be useful in detecting the presence of low concentrations of micrococcal nuclease in clinical specimens such as blood serum.

*Staphylococcus aureus* Detection Method

In certain embodiments, the present invention provides a method of detecting *Staphylococcus aureus* in a test sample, comprising:
  (a) contacting the test sample with a probe of any one of claims 1-xxx to form a digested probe,
  (b) collecting the digested probe, and
  (c) measuring the fluorescence emitted by the digested probe.

In certain embodiments, the test sample is a biological sample. In certain embodiments, the biological sample is a blood sample. In certain embodiments, the blood sample is whole blood, serum or plasma.

In certain embodiments, the sample further comprises calcium chloride. In certain embodiments, the calcium chloride is at a concentration of about 5 to 20 mM. In certain embodiments, the calcium chloride is at a concentration of about 10 mM.

In certain embodiments, the sample has been heated at 55-100° C. for 10 seconds to 20 hours to form a heat-treated test sample prior to testing. In certain embodiments, the sample has been heated at about 70 to 95° C. In certain embodiments, the sample has been heated for about 15-30 minutes. In certain embodiments, the sample has been heated at about 90° C. for about 20 minutes to form a heat-treated test sample prior to testing.

In certain embodiments, the sample has been clarified after the heating step. In certain embodiments, the clarification is by means of centrifugation at 1 k to 20 k×g for 10 seconds to 20 minutes after the heating step to form a heat-treated, clarified supernatant test sample. In certain embodiments, the clarification is by means of centrifugation at about 17 k×g for about 10 minutes after the heating step to form a heat-treated, clarified supernatant test sample. In certain embodiments, the clarification is by means of filtration after the heating step to form a heat-treated, clarified supernatant test sample.

In certain embodiments, the heat-treated test sample has been concentrated prior to testing. In certain embodiments, the concentration is by means of immunoprecipitation. In certain embodiments, the immunoprecipitation is by means of anti-micrococcal nuclease antibody-coupled magnetic beads. In certain embodiments, the magnetic beads are Protein G-coupled magnetic beads.

In certain embodiments, the probe is the probe is FAM/ TTTTTTTTTTT/ZEN/IAbRQSp/(SEQ ID NO. 5), wherein 6-FAM is a fluorescein amidite fluorophore, ZEN is a ZEN dark quencher, and IAbRQSp is a Iowa Black dark quencher, and the fluorescence is measured at 485/530 nm excitation/ emission.

In certain embodiments, the present invention provides a *Staphylococcus aureus* detection method. In certain embodiments, the method involves the following steps:
  1. Add $CaCl_2$ to plasma for a final concentration of ~10 mM.
  2. Heat plasma to 90° C. for 20 minutes.
  3. Centrifuge heat precipitated plasma at 17,000×g for 10 min.
  4. Resuspend anti-micrococcal nuclease antibody-coupled magnetic beads with heat-treated plasma supernatant.
  5. Wash antibody-nuclease-bead complex.
  6. Incubate PolyTT probe in optimal buffer with nuclease-antibody-bead complex.
  7. Collect digested probe in buffer from nuclease-antibody-bead complex.
  8. Measure fluorescence.

Example 1

Because of the difficulty in detecting trace quantities of *E. coli* rapidly with field-compatible methods, the present invention was developed. The invention is a pair of self-hybridizing, quenched fluorescent oligonucleotide probes that are digested (i.e., cleaved) and thereby activated by Endonuclease I, a deoxyribonuclease (DNase) expressed in *Escherichia coli* (*E. coli*). The probes enable the detection of as few as 219 *E. coli* bacterial cells after brief (as little as 1 hour) incubations.

Probes

The invention consists of a pair of quenched fluorescent, chemically modified oligonucleotide probes. These synthetic molecules have a fluorophore on one end and a pair of quenching moieties on the other end. The quenchers greatly diminish the fluorescence of the fluorophore, due to their physical properties and their close proximity. Upon degradation of the oligonucleotide, the quenchers diffuse away from the fluorophore and the fluorophore then exhibits much greater fluorescence.

In one embodiment, the probes were as follows:

```
                                         (SEQ ID NO: 27)
Oligo 1 (8-mer DNA): /56-FAM/CTACGTAG/ZEN//

3IAbRQSp/
``` where 56-FAM is a FAM fluorophore (fluorescein amidite), the bold letters indicate deoxy nucleotides (DNA), ZEN is the ZEN fluorescence quencher and 3IAbRQSp is the Iowa Black fluorescence quencher. The probe is listed from the 5'- to the 3'-ends.

```
                                          (SEQ ID NO: 4)
Self-Hyb Fl: /56-FAM/fCfUfAfCfGfUfAfG/ZEN//

3IAbRQSp/
``` where 56-FAM is a FAM fluorophore (fluorescein amidite), nucleotides are fA (2'-fluoro modified A), fC (2'-fluoro modified C), fG (2'-fluoro modified G) and fU (2'-fluoro modified U), ZEN is the ZEN fluorescence quencher and 3IAbRQSp is the Iowa Black fluorescence quencher. The probe is listed from the 5'- to the 3'-ends.

The probes are also self-complementary, meaning that each will bind an identical copy of itself, oriented in the opposite direction, forming a double-stranded nucleic acid substrate for nucleases. In this double-stranded form, the probes serve as robust substrates for Endonuclease I, a nuclease expressed in *E. coli*. that prefers double-stranded DNA substrates. When the probes are incubated in lysates of *E. coli* cells, the Endonuclease I which is present in the lysates degrades them, resulting in an increase in fluorescence. The following optimal buffer was developed for these reactions: 50 mM Tris-HCl, pH 8.0, 100 mM NaCl, 12 mM MgCl$_2$, 1% Triton X-100, 1 mM DTT, 1× Protease Inhibitor Cocktail (cOmplete ULTRA Tablets, Mini, EDTA-free, EASYpack from Roche, cat #05 892 791 001; 1× is 1 tablet per 10 ml as specified in product literature).

For detection of *E. coli* in the field, the probes would need to be coupled with a field-compatible bacterial concentration device and with a field-compatible fluorescence measuring device.

Results

The inventors previously developed quenched fluorescent, nuclease-activated oligonucleotide probes that detect the presence of *Staphylococcus aureus* by detecting the activity of one of its nucleases. These probes have a fluorophore on their 5'-ends that exhibits very little fluorescence because tow fluorescence quenchers, which are coupled to the 3'-end, are in close proximity. Upon digestion of the oligonucleotide portion, the quenchers diffuse away from the fluorophore, resulting in its unquenching and thus activation of the probe. With the present invention, the inventors explored whether *Escherichia coli* might also be detected in a similar manner. Endonuclease 1 of *E. coli* is commonly deleted in strains used for molecular biology procedures in order to increase the yield of plasmid DNA production (Taylor, R. G., Walker, D. C. & Mcinnes, R. R. *Escherichia-Coli* Host Strains Significantly Affect the Quality of Small-Scale Plasmid DNA Preparations Used for Sequencing. *Nucleic Acids Res* 21, 1677-1678 (1993)). This protein, therefore, was focused on as a candidate enzyme of *E. coli* that might be used for its detection.

Figure 2:
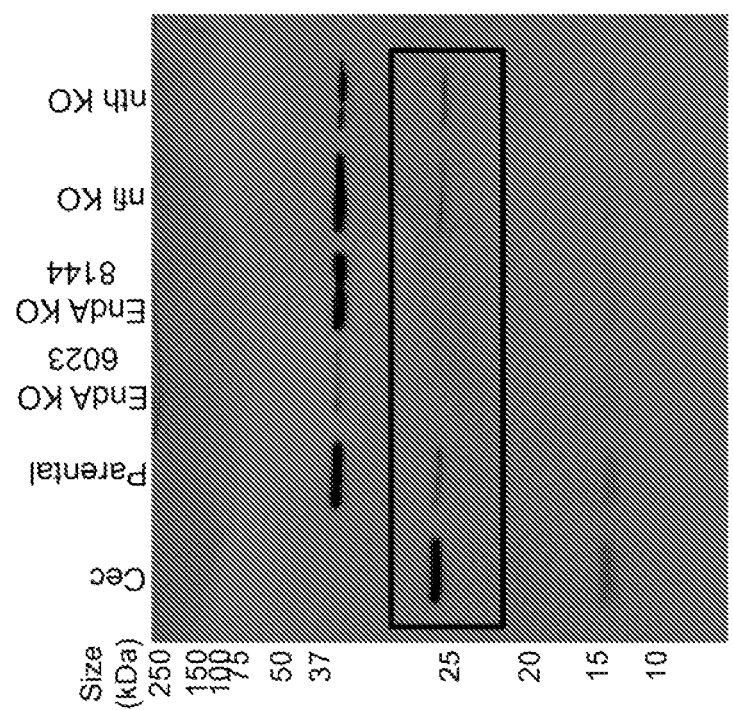
FIG. 2. Western blot confirms that Endonuclease 1 protein is absent in EndA KO *E. coli* strains. Lysates of the indicated *E. coli* strains were resolved with SDS-PAGE, transferred to a membrane and probed with a rabbit anti-Endonuclease 1 antibody. The box indicates a band of the approximate molecular weight of Endonuclease 1 that is visible in Cec, Parental, nfi KO and nth KO strains, but not in the EndA KO strains.

A DNA zymogram was performed (FIG. 1) with *E. coli* lysates to measure *E. coli* nuclease activities. In addition to the FDA strain Seattle 1946 (a representative coliform *E. coli* strain), the inventors also included an Endonuclease 1 knockout strain (Keio EndA KO) of the Keio collection and its parental strain (K12) as a control in this experiment (Baba, T., et al. Construction of *Escherichia coli* K-12 in-frame, single-gene knockout mutants: the Keio collection. *Mol Syst Biol* 2, 2006 0008 (2006)). In the zymogram assay, dark bands indicate digestion of the DNA that is embedded in the gel and thus nuclease activity of the resolved proteins. A roughly 25 kDa band is clearly evident in the coliform *E. coli* lysate and a band of the same size is also present in the Keio parental *E. coli* strain, while no band of the corresponding size is visible in the EndA strain that lacks Endonuclease 1. Western blot analysis of Endonuclease 1 in lysates of this and another Keio collection Endonuclease 1 knockout *E. coli* strain (FIG. 2) revealed absence of bands of the approximate molecular weight of Endonuclease 1, thus confirming the Endonuclease 1-null status of these strains. Together, these data support the notion that Endonuclease 1 is a viable candidate for detecting coliform *E. coli*.

Figure 3:
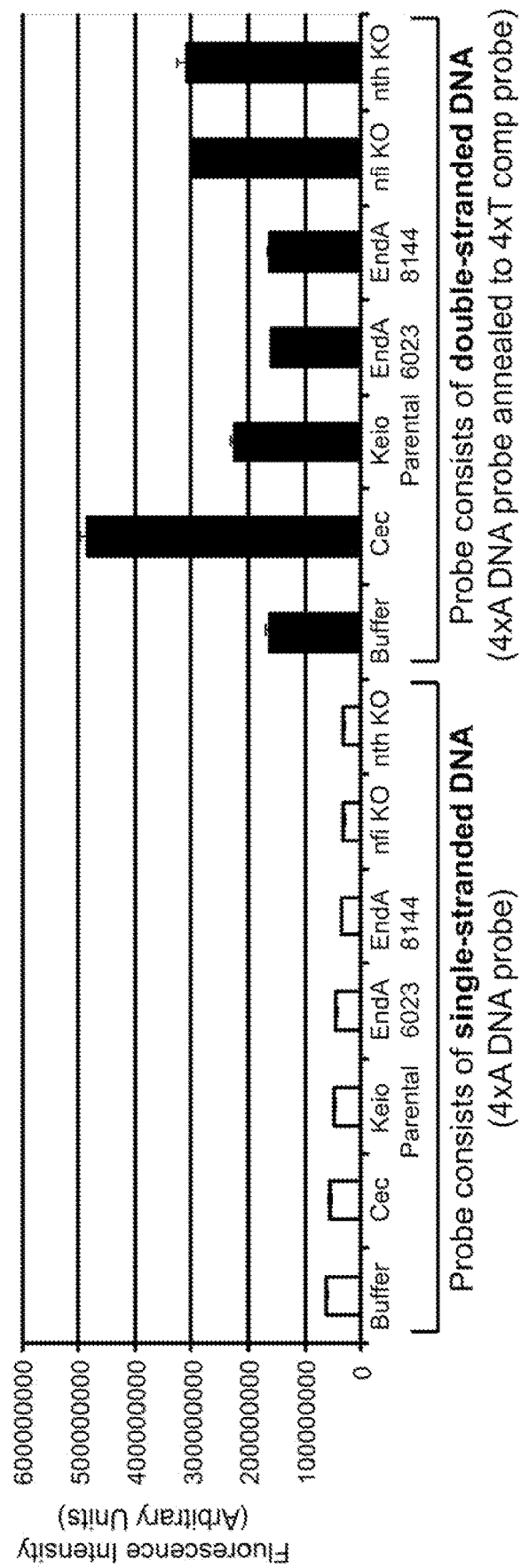
FIG. 3. Preference of *E. coli* nuclease(s) for double-stranded oligonucleotides. The 4×A DNA probe (open bars) or the 4×A DNA probe annealed to a non-fluorescent complementary oligonucleotide (black bars) were incubated with buffer only or with lysates of the indicated strains of *E. coli* for 1 hour at 37° C.
Figures 5A, 5B:
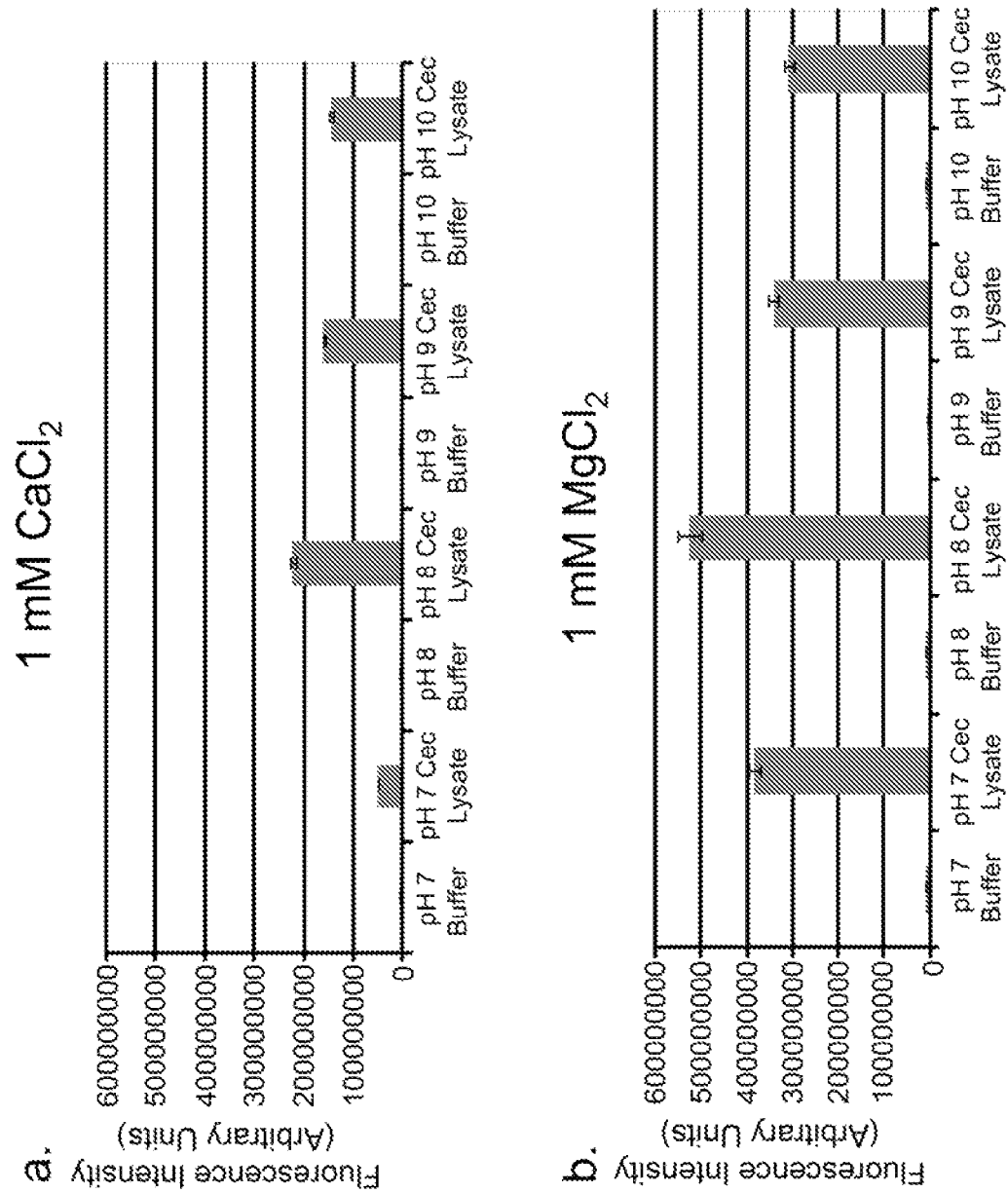
FIGS. 5A and 5B. Optimal pH and divalent cation for Endonuclease I activity. Self-Hybridizing DNA Probe (Oligo 1) was incubated in buffer only or Coliform *E. coli* lysates (Cec) for 30 minutes at 37° C. The buffer consisted of 50 mM Tris with varying pH, 1% Triton X-100, 1 mM DTT, 1× protease inhibitors, 50 mM NaCl and 1 mM of either $CaCl_2$ or $MgCl_2$ as indicated.
Figure 6:
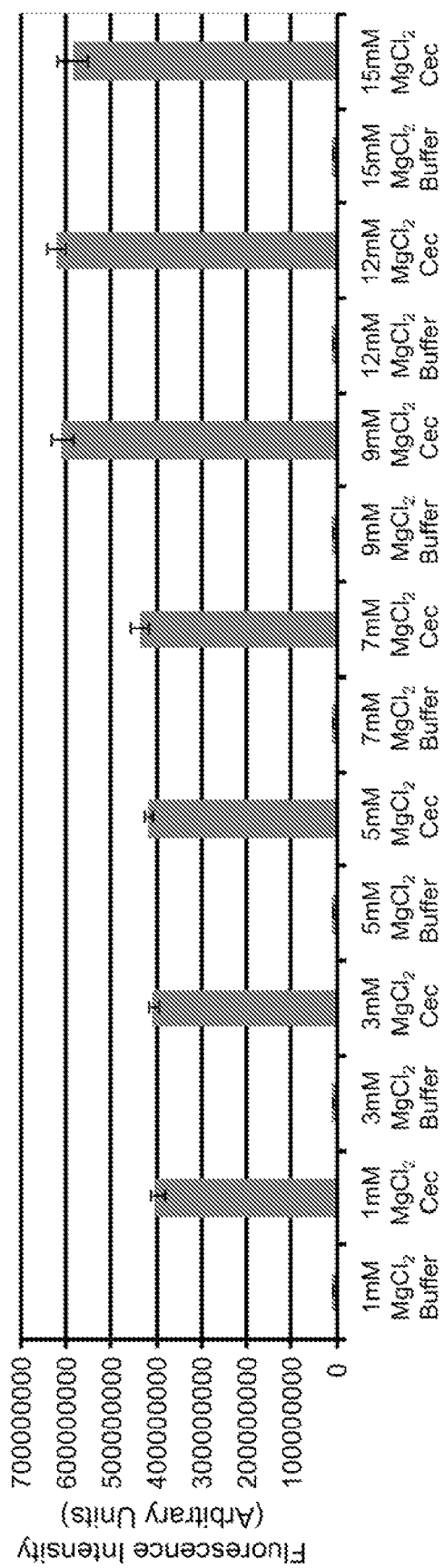
FIG. 6. Optimal MgCl$_2$ concentration for Endonuclease I activity. Self-Hybridizing DNA Probe (Oligo 1) was incubated in buffer only or Coliform *E. coli* lysates (Cec) for 30 minutes at 37° C. The buffers consisted of 50 mM Tris pH 8, 1% Triton X-100, 1 mM DTT, lx protease inhibitors, 50 mM NaCl and the indicated concentrations of MgCl$_2$.

Next, Endonuclease 1 activity was measured with a quenched fluorescent probe rather than a gel-based assay due to the simplicity and field-compatibility of this simpler approach (Kelemen, B. R., et al. Hypersensitive substrate for ribonucleases. *Nucleic Acids Res* 27, 3696-3701 (1999)). A single-stranded DNA probe was not activated (i.e., signal did not exceed that of the buffer only control) in lysates of the coliform *E. coli* strain, the Keio collection parental strain or any of the Keio collection mutants tested (FIG. 3). When the same probe was tested after being made into a double-stranded form by annealing an unlabeled complementary DNA oligonucleotide (see Table 3 for probe details), the probe was activated (i.e., signal exceeded that in the buffer only control) in several of the lysates tested. In particular, the lysates of the coliform *E. coli*, the Keio parental strain and the nfi and nth Keio collection mutants (these have different nucleases deleted) all produced probe activation that exceeded that seen in the buffer only control (Asahara, H., Wistort, P. M., Bank, J. F., Bakerian, R. H. & Cunningham, R. P. Purification and characterization of *Escherichia coli* endonuclease III from the cloned nth gene. Biochemistry 28, 4444-4449 (1989); Guo, G., Ding, Y. & Weiss, B. nfi, the gene for endonuclease V in *Escherichia coli* K-12. *J Bacteriol* 179, 310-316 (1997)).

TABLE 3

Names, sequences and modifications of oligonucleotide probes used

| Oligo Name | Oligo Sequence | SEQ ID NO |
|---|---|---|
| 4xA DNA | FAM-mUmCmUmCAAAAmGmUmAmC-ZEN-RQ | 28 |
| 4xT Comp | mGmUmAmCTTTTmGmAmGmA | 29 |
| Self-Hybridizing Probes | | |
| Oligo 1 | FAM-CTACGTAG-ZEN-RQ | SEQ ID NO: 30 |
| Self-Hyb LNA | FAM- +C + T + A + C + G + T + A + G-ZEN-RQ | SEQ ID NO: 31 |
| Self-Hyb OMe | FAM-mCmUmAmCmGmUmAmG-ZEN-RQ | SEQ ID NO: 32 |
| Self-Hyb Fl | FAM-fCfUfAfCfGfUfAfG-ZEN-RQ | SEQ ID NO: 33 |

FAM FAM fluorophore (fluorescein amidite)
ZEN "ZEN" fluorescence quencher
RQ "Iowa Black" fluorescence quencher
mA 2'-O-methyl modified A
mC 2'-O-methyl modified C
mG 2'-O-methyl modified G
mU 2'-O-methyl modified U
fA 2'-fluoro modified A
fC 2'-fluoro modified C
fG 2'-fluoro modified G
fU 2'-fluoro modified U
+A Locked nucleic acid modified A
+C Locked nucleic acid modified C
+G Locked nucleic acid modified G
+U Locked nucleic acid modified U
Nucleotides written in bold are deoxy nucleotides (DNA).
All sequences are written from 5' to 3' orientation.

It was noted that the signal of the double-stranded fluorescent probe incubated in buffer was substantially greater than the same probe in its single-stranded form incubated in buffer. This is likely due to the rigid helical structure of the double-stranded form which forces the fluorophore apart from the quenchers. In contrast, the flexibility of the single-stranded form likely allows for hydrophobic interactions between the fluorophore and quenchers that will promote substantially greater quenching. Neither of the lysates of 2 distinct Endonuclease 1 knockout strains from the Keio collection (6023 and 8144) activated the double-stranded probe above the level seen in the buffer only control. The activity seen in the other lysates can therefore be attributed to Endonuclease 1. That Endonuclease 1 has a preference for double-stranded DNA is consistent with previous published studies (Lehman, I. R., Roussos, G. G. & Pratt, E. A. The deoxyribonucleases of *Escherichia coli*. II. Purification and properties of a ribonucleic acid-inhibitable endonuclease. *J Biol Chem* 237, 819-828 (1962)).

Next, the inventors developed a quenched fluorescent oligonucleotide probe that is highly sensitive to Endonuclease 1, and also exhibits a low basal level of fluorescence (i.e., strong quenching). A self-annealing probe configuration (see FIG. 4 for cartoon representation) yields a double-stranded substrate for enzyme digestion and also fixes the quenchers of one probe in close proximity to the fluorophore of its binding partner for strong quenching. A DNA version of this probe (Oligo 1) was efficiently digested in lysates of the coliform *E. coli* strain (FIGS. 5-9).

Figure 7:
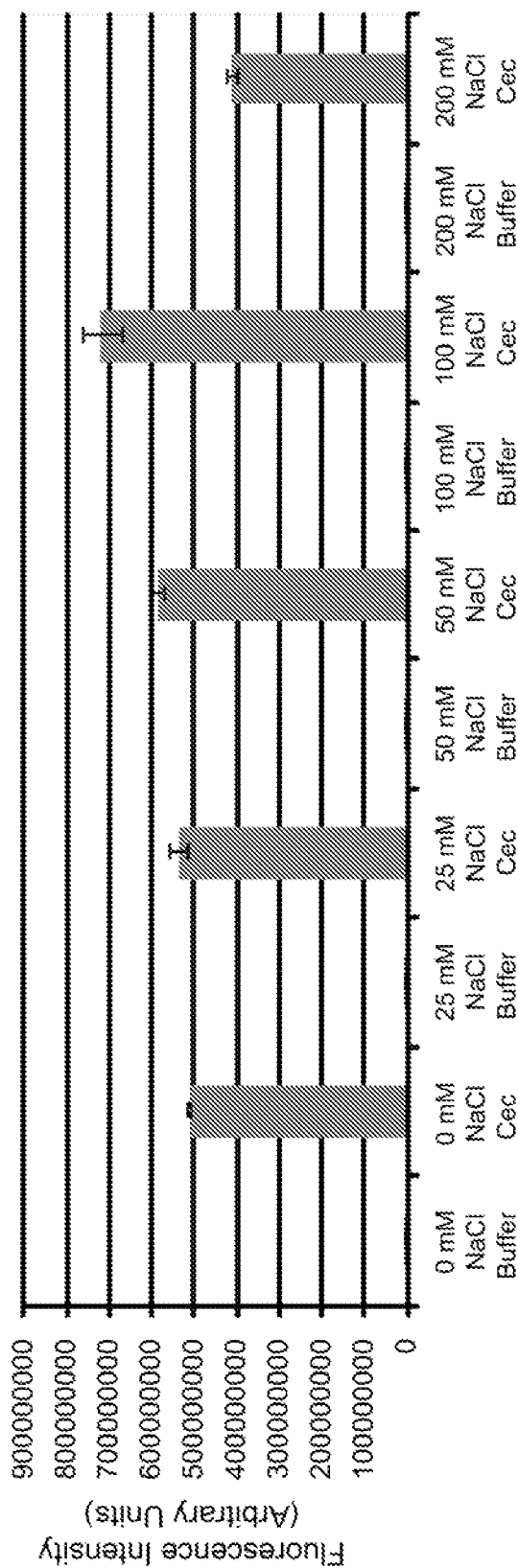
FIG. 7. Optimal NaCl concentration for Endonuclease I activity. Self-Hybridizing DNA Probe (Oligo 1) was incubated in buffer only or Coliform *E. coli* lysates (Cec) for 30 minutes at 37° C. The buffers consisted of 50 mM Tris pH 8, 1% Triton X-100, 1 mM DTT, lx protease inhibitors, 12 mM MgCl$_2$ and the indicated concentrations of NaCl. The optimized buffer used in subsequent experiments consists of: 50 mM Tris, pH 8, 1% Triton X-100, 1 mM DTT, 1× protease inhibitors, 12 mM MgCl$_2$, 100 mM NaCl.

To identify the optimal buffer conditions for digestion of Oligo 1 in coliform *E. coli* lysates, the inventors compared the activation of this probe in buffers containing different divalent cations (FIG. 5), various pHs (FIG. 5), various divalent cation concentrations (FIG. 6) and various sodium chloride concentrations (FIG. 7). These results yielded an optimized Endonuclease 1 reaction buffer consisting of 50 mM Tris-HCl, pH 8, 1% Triton X-100, 1 mM DTT, 1× protease inhibitors, 12 mM $MgCl_2$, 100 mM NaCl (see Methods for details regarding the protease inhibitors). Subsequent experiments were carried out with this optimized buffer.

Figure 8:
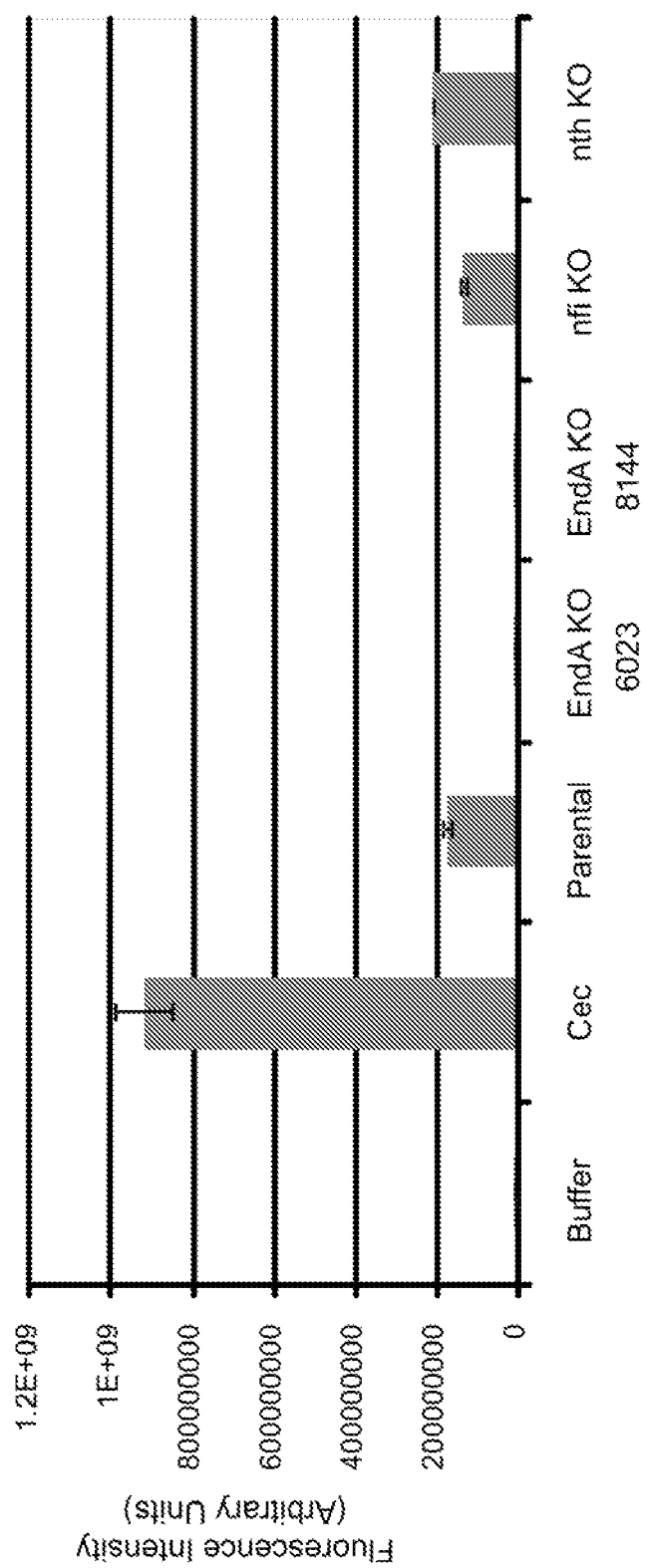
FIG. 8. Endonuclease I is the nuclease within *E. coli* lysates responsible for Oligo 1 activation. Oligo 1 was incubated with buffer only (optimized digestion buffer described above) or with lysates of the indicated strains of *E. coli* for 30 minutes at 37° C. Note that 2 distinct strains of *E. coli* (Keio collection strains 6023 and 8144) in which Endonuclease I is deleted were tested.

To determine whether the digestion of Oligo 1 in the optimized buffer was indeed due to Endonuclease 1 activity, we measured Oligo 1 activation in lysates of coliform *E. coli* and the Keio collection parental, and Endonuclease 1, nfi and nth knockout strains (FIG. 8). Activation of the probe in all the lysates except those of the Endonuclease 1 knockout strains confirms that Endonuclease 1 is the nuclease responsible for Oligo 1 digestion in the lysates in which it is present.

Figure 9:
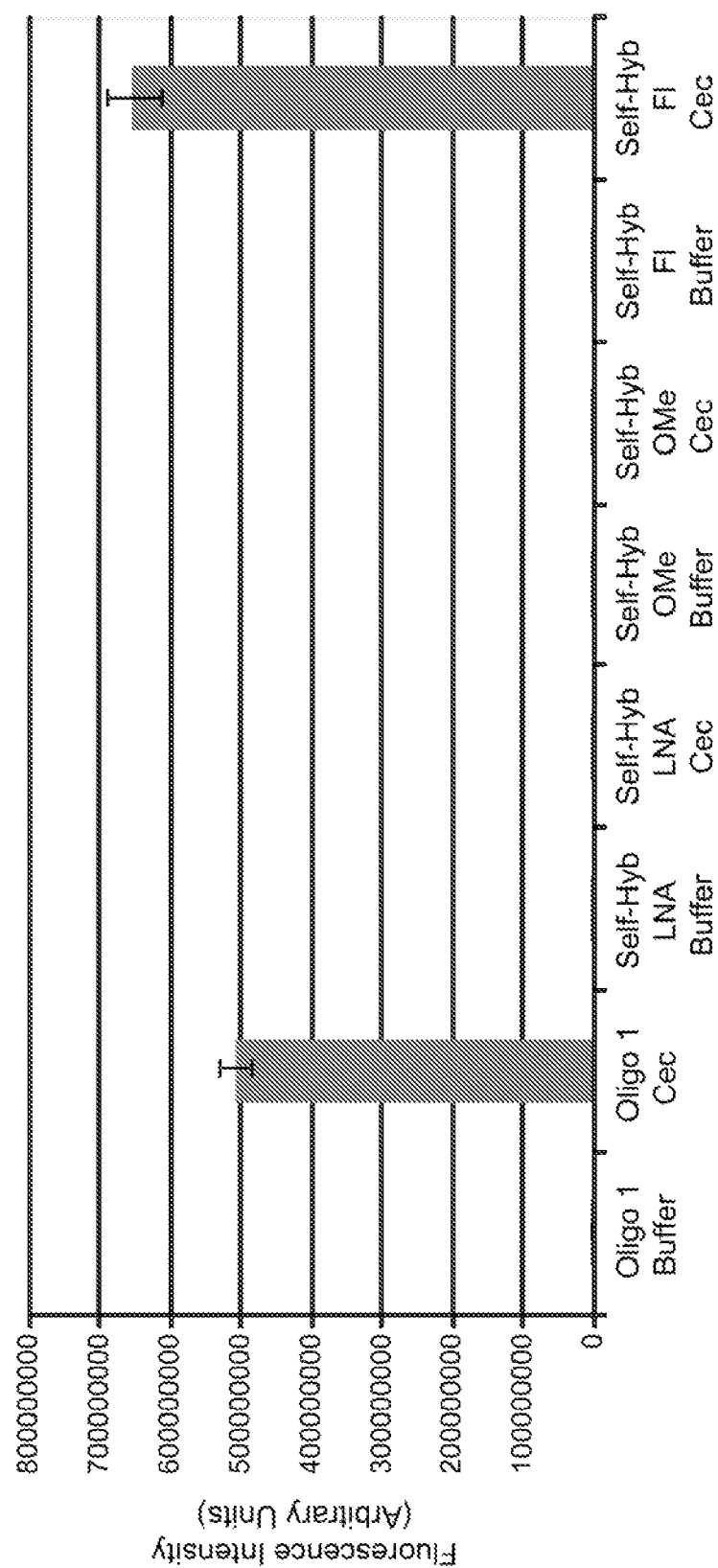
FIG. 9. Self-hybridizing probes composed of DNA (Oligo 1) and 2'-fluoro modified RNA (Self-Hyb Fl) are activated by nuclease(s) in coliform *E. coli* (Cec) lysate. Each of the indicated probes was incubated with buffer only (optimized digestion buffer described above) or with coliform *E. coli* lysate for 30 minutes at 37° C.
Figure 10:
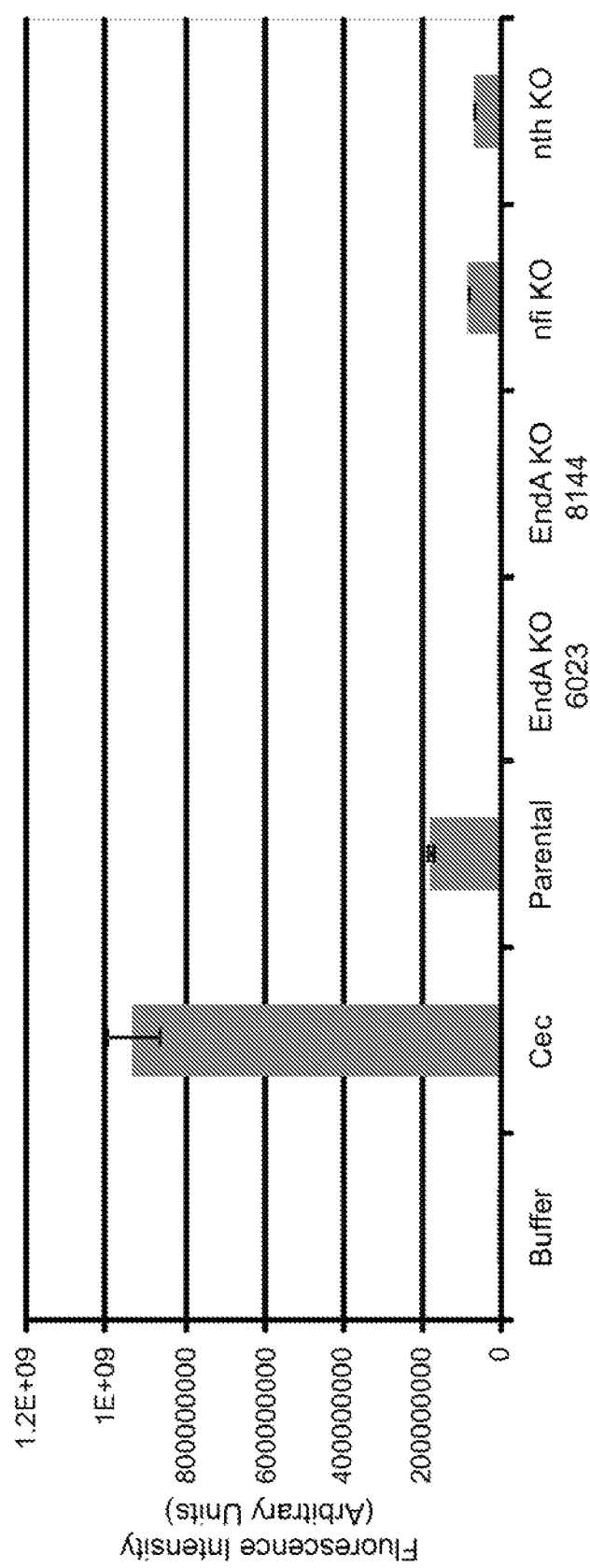
FIG. 10. Endonuclease I is the nuclease within *E. coli* lysates responsible for Self-Hyb Fl probe activation. The Self-Hyb Fl probe was incubated with buffer only (optimized digestion buffer described above) or with lysates of the indicated strains of *E. coli* for 30 minutes at 37° C. Note that 2 distinct strains of *E. coli* (Keio collection strains 6023 and 8144) in which Endonuclease I is deleted were tested.

Next, the activation of Oligo 1 was compared to that of three additional probes that are identical, except that the nucleotides are modified differently (see Table 3 for a complete description of the probes). The modifications were chosen based on those that are known to provide resistance to many nucleases, such as mammalian serum nucleases (Behlke, M. A. Chemical modification of siRNAs for in vivo use. Oligonucleotides 18, 305-319 (2008)). One of these additional probes, "Self-Hyb Fl", in which 2'-fluoro modified RNA nucleotides were substituted for the DNA nucleotides of Oligo 1, was robustly activated in the coliform *E. coli* lysate (FIG. 9). To determine whether activation of the Self-Hyb Fl probe is also due to Endonuclease 1, we again used the Keio collection parental and nuclease knockout strains in a probe activation experiment (FIG. 10). As with Oligo 1 probe activation, the Self-Hyb Fl probe is selectively activated in the lysates in which Endonuclease 1 is present, thus indicating that Endonuclease 1 is also the nuclease responsible for its activation.

Figure 11:
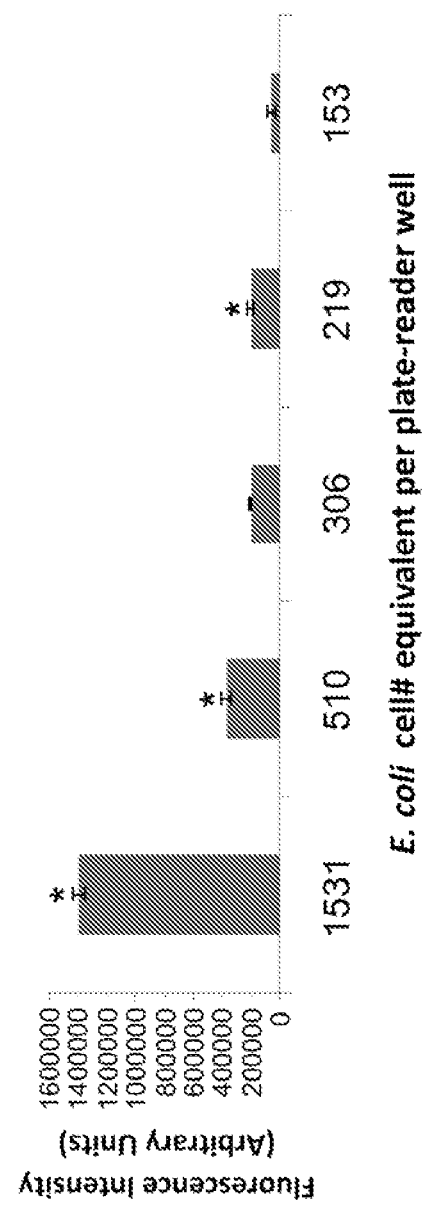
FIG. 11. Coliform *E. coli* detection sensitivity with nuclease-activated probe. Coliform *E. coli* lysate was diluted and incubated with "Self-Hyb Fl" double-stranded chemically modified RNA probe for 1 hour at 37° C. Each 10 µl reaction was then divided in 3 and fluorescence was measured with a plate reader. Numbers on X-axis indicate estimate of bacterial cell number per well of the corresponding data point. The fluorescence level of the probe incubated in buffer (i.e., no nucleases) was subtracted from each value. *The difference between these values and the "buffer only" control is statistically significant.

Finally, to determine the minimal number of *E. coli* bacterial cells that can be detected with this approach in its present form, the activation of the Self-Hyb Fl probe was measured in various dilutions of a lysate of coliform *E. coli* cells (FIG. 11). Using the optical density of the culture (measured prior to lysis) to estimate the concentration of bacteria, it was found that the equivalent of as few as 219 bacterial cells per well of the plate-reader can be detected above the background level measured with buffer only.

In summary, nuclease-activated oligonucleotide probes were developed that can rapidly detect the presence of *E. coli* with high sensitivity.

Methods

Culture Growth and Processing

Overnight cultures of indicated *E. coli* strains were grown at 37° C. in a shaking incubator. Coliform *E. coli* was grown in Tryptic soy broth without antibiotics, the Keio collection mutants were grown in LB supplemented with kanamycin. The Keio parental K12 strain was grown in LB without antibiotics. Bacteria from 1 milliliter of each culture was pelleted by centrifugation, washed in 1 ml of 10 mM Tris-HCl pH 7.4 and lysed with 30 mM Tris-HCl pH8.0, 1 mM EDTA, 20% sucrose, 10 µg/ml Lysozyme. The soluble portion of each lysate (this will be referred to as the "lysate" from this point forward) was isolated by collecting supernatant following centrifugation at full speed in a microcentrifuge. Lysates were then dialyzed into various buffers, whose composition yielded the final reaction conditions indicated in figures upon dilution of 1 µl of the dialyzed product with 8 µl dialysis buffer and 1 microliter of probe diluted in water. Dialyzed lysates were either used immediately, or aliquoted and stored at −20° C.

Fluorescence Plate-Reader Assays

1 µl of a stock solution of 500 µM of the indicated probe was first diluted with 9 µls of high performance liquid chromatography (HPLC) grade water. One microliter dialyzed lysate (1 µg/µl) and 8 µl dialysis buffer were added to 1 µl of the diluted probe. The reaction was incubated at 37° C. for the time indicated. After incubation, 290 µl of stop solution (10 mM EDTA+10 mM EGTA in DPBS without divalent cations) was then added to each reaction and fluorescence of reactions was measured in triplicate (95 µls/well) in a fluorescence plate-reader (Analyst HT).

Bacterial Numbers Calculations

For the experiment shown, the OD600 of an overnight culture of the coliform bacterial strain, diluted 1:10 was found to be 0.574. Using $8\times10^8$ cells/(ml*OD600) as a conversion factor, this amounts to $10*0.574*8\times10^8=4.6\times10^9$ cells/ml. 1 ml of this culture was pelleted by centrifugation and the pellet was lysed in 1 ml buffer. The lysate was dialyzed and then diluted 1:1,000, 1:3,000, 1:5,000, 1:7,000 and 1:10,000 in dialysis buffer. One microliter of each dilution was used per 10 µl reaction, each of which was divided into 3 wells of a 96 well plate for fluorescence measurements. The number of bacterial cells per well of the plate was calculated as in the following example (for the 1:1,000 dilution): 1 µl*$4.6\times10^9$ cells/ml*(1 ml/1,000 µl)*(1/1,000)*(1/3)=1,531 cells/well.

Zymograms

30 µg of each *E. coli* lysate were run on 12% acrylamide SDS-PAGE gels polymerized with 1 nmol salmon sperm DNA (Invitrogen) per 8 ml gel mixture. Nucleases were activated by a series of washes. The first wash contains 12 mM $MgCl_2$ and 2.5% Triton X-100. The second wash contains 12 mM $MgCl_2$, 2.5% TX-100, 100 mM NaCl, 1 mM DTT and 50 mM Tris-HCl pH 8.0. The third wash has 12 mM $MgCl_2$, 100 mM NaCl, 1 mM DTT and 50 mM Tris-HCl pH 8.0. The gels were then incubated in the third wash for 2 hrs at 37° C. Gels were stained with SYBR Gold for 30 minutes and visualised with a UV-light transilluminator.

Bacterial Strains

Coliform ((Migula) Castellani and Chalmers, FDA strain Seattle 1946, ATCC #25922), wildtype (parental) *E. coli* (K-12 Catalog # NC0451794) and EndA (catalog #s NC0493574 and OEC4987200828144), nfi (catalog # OEC4987-200829641) and nth (catalog # OEC4987-213606177) KO strains (Thermo-Fisher).

Western Blotting

Western blotting was used to assess expression of Endonuclease 1 in the *E. coli* lysates. Lysates were resolved on 12% acrylamide SDS-PAGE gels and transferred to a PVDF membrane. The membrane was blocked 2 hours in 5% milk diluted in TBS+0.2% NP-40. The membrane was then incubated overnight at 4° C. with a rabbit anti-Endonuclease 1 antibody (diluted 1:5000 in milk), washed 3 times in TBS+0.2% NP-40, then incubated with goat anti-rabbit HRP secondary antibody (1:5000 in TBS-T) 1 hour at room temperature. After washing 3× in TBS+0.2% NP-40, the membrane was developed with ECL.

Example 2

Urinary tract infections (UTIs) are thought to be the most common type of bacterial infection and they are also the most common type of hospital-acquired infection (Foxman, B. Epidemiology of urinary tract infections: incidence, morbidity, and economic costs. *Am J Med* 113 Suppl 1A, 5S-13S (2002); Wilson, M. L. & Gaido, L. Laboratory diagnosis of urinary tract infections in adult patients. *Clin Infect Dis* 38, 1150-1158 (2004)). The predominant pathogen responsible for these infections is *E. coli* (Foxman, B. The epidemiology of urinary tract infection. *Nat Rev Urol* 7, 653-660 (2010); Kaper, J. B., Nataro, J. P. & Mobley, H. L. Pathogenic *Escherichia coli*. *Nat Rev Microbiol* 2, 123-140 (2004)). If left untreated, UTIs of the lower urinary tract can progress to very serious and life-threatening conditions, including infections of the kidneys (pyelonephritis) and blood (bacteremia) (Kaper, J. B., Nataro, J. P. & Mobley, H. L. Pathogenic *Escherichia coli*. *Nat Rev Microbiol* 2, 123-140 (2004).).

Upon initial clinical evaluation of suspected UTIs, rapid diagnosis and identification of the causative bacterial species would enable the early administration of an appropriate therapeutic reagent and thereby reduce the number of such serious infections. For instance, rapid identification of *E. coli* in clinical urine samples would enable physicians to quickly select antibiotics based on established antibiotic resistance profiles of *E. coli* strains found to cause UTIs in the region. However, current clinical diagnostic methods do not provide rapid identification of bacterial pathogens responsible for UTIs. Microbiological diagnostic methods require culture and take at least 24 hours to reliably identify the responsible bacterial pathogen (Wilson, M. L. & Gaido, L. Laboratory diagnosis of urinary tract infections in adult patients. *Clin Infect Dis* 38, 1150-1158 (2004)). Urinalysis methods (e.g., measures of nitrite or leukocyte esterase) lack the desired sensitivity and specificity for reliable diagnosis of UTIs and do not identify the causative bacterial species (Wilson, M. L. & Gaido, L. Laboratory diagnosis of urinary tract infections in adult patients. *Clin Infect Dis* 38, 1150-1158 (2004)).

Detection of *E. coli* with the nuclease-activated probes of the present invention is sufficiently rapid (<3 hours) and sensitive to address this unmet need for a novel clinical diagnostic assay for *E. coli* UTIs. The diversity of nucleases found in nature also suggests that an assay specific for *E. coli* (versus the nucleases present in other pathogens that cause UTIs) allows for tailoring the makeup of the probe and the digestion conditions to specifically allow Endonuclease I of *E. coli* to yield probe digestion.

Example 3

Food poisoning can be caused by eating food contaminated with bacteria, such as with *Salmonella* or *E. coli*. Food, such as beef, poultry, milk or eggs, may be contaminated during food processing or food handling. The present method can easily detect contaminating bacteria on site, such as at a processing plant.

Example 4

The present invention provides, in certain embodiments, a means of rapidly diagnosing *Staphylococcus aureus* bacteremia, a common medical condition with a very high mortality rate. (van Hal, S. J. et al. Predictors of mortality in *Staphylococcus aureus* Bacteremia. Clinical microbiology reviews 25, 362-386, doi:10.1128/cmr.05022-11 (20012); Klevens, R. M. et al. Invasive methicillin-resistant *Staphylococcus aureus* infections in the United States. Jama 298, 1763-1771, doi:10.1001/jama.298.15.1763 (2007)). Bacteremia is a condition in which viable bacteria are found in the blood circulation. Current diagnostic methods for *S. aureus* bacteremia require time-consuming culturing methods that take 24-48 hours. Rapid diagnosis of this condition would facilitate the administration of effective antibiotic therapy at earlier times and is expected to substantially reduce the mortality rate. The utility of a quenched fluorescent, nuclease-activated oligonucleotide probe-based approach for detecting bacterial pathogens via their nuclease activities (Example 1 above; Hernandez, F. J. et al. Noninvasive imaging of *Staphylococcus aureus* infections with a nuclease-activated probe. Nature medicine 20, 301-306, doi: 10.1038/nm.3460 (2014). These probes are short oligonucleotides with dark quenchers coupled to their 3'-ends which suppress the fluorescence of a fluorophore on the 5'-end when the probes are intact due to the close proximity of quenchers to the fluorophore. Upon cleavage of the probe by a nuclease, the quenchers diffuse away from the fluorophores resulting in probe activation through unquenching of the fluorophore. These probes can be engineered through nucleotide modifications to be selectively digestible (and thus activatable) by target nucleases of bacterial pathogens.

To explore whether probes engineered to specifically detect *S. aureus* via the activity of its secreted nuclease (known as micrococcal nuclease) might enable the diagnosis of *S. aureus* bacteremia, the probes were incubated with plasma of patients with confirmed *S. aureus* bacteremia and measured fluorescence. It was not possible to detect the nuclease activity in these specimens. This is perhaps not surprising considering that bacteremia typically occurs with a very small number of bacteria per unit volume of blood (i.e., <10 bacterial cells per 5 ml of blood).

The sensitivity of this assay was determined by measuring the activity of various concentrations of purified micrococcal nuclease, diluted in buffer. The assay sensitivity was also evaluated in the context of human serum by preparing dilutions of purified micrococcal nuclease in human serum and carrying out the assay with this material. Interestingly, it was found that the assay was substantially less sensitive in human serum than in buffer. This suggested that there are components of human serum that inhibit the activity of the nuclease. Indeed, antibodies that inhibit the catalytic activity of micrococcal nuclease were recently found to be common components of human serum. (Schilcher, K. et al. Increased neutrophil extracellular trap-mediated *Staphylococcus aureus* clearance through inhibition of nuclease activity by clindamycin and immunoglobulin. The Journal of infectious diseases 210, 473-482, doi:10.1093/infdis/jiu091 (2014)).

Micrococcal nuclease has been known for decades to be resistant to inactivation by heat denaturation when calcium and other proteins are present. (Cuatrecasas, P., Fuchs, S. &

Figure 12:
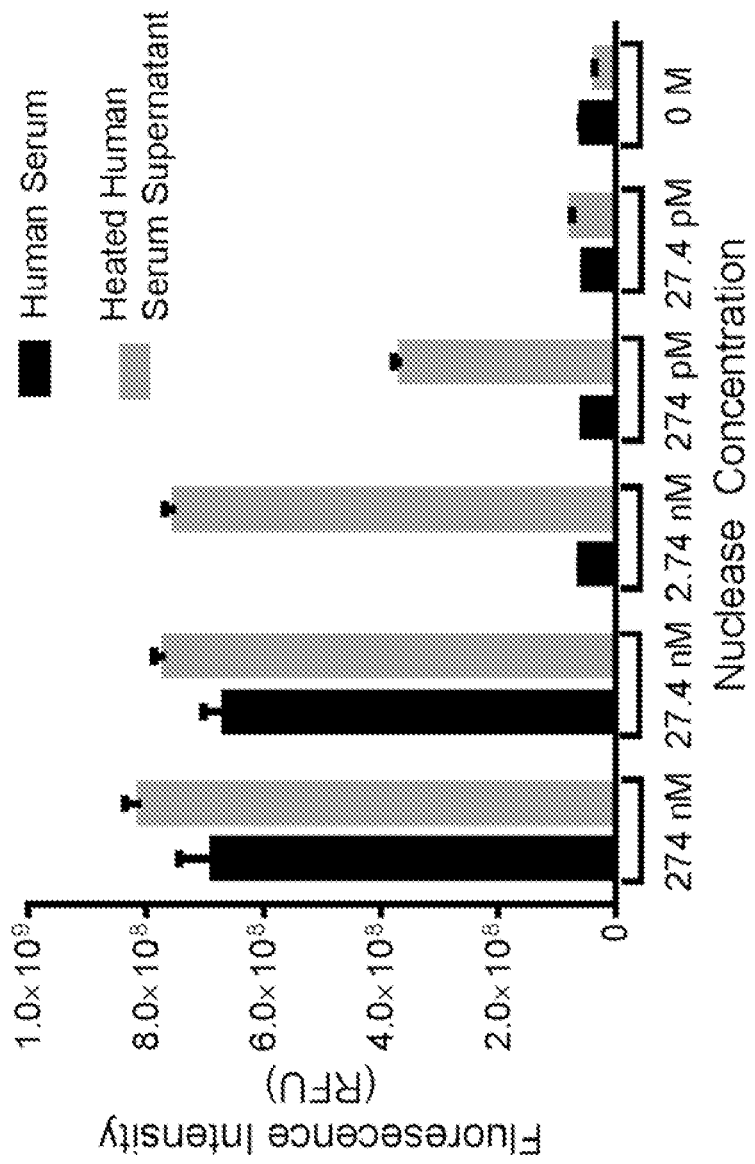
FIG. 12. Micrococcal nuclease activity is unmasked by heating human serum that contains the nuclease. Micrococcal nuclease was added to human serum to yield the concentrations indicated above. The samples were then either unheated, or heated and centrifuged. Unheated samples and supernatants of heated samples were then incubated with the Poly TT probe and fluorescence was measured. Note that at concentrations of 2.74 nM or less, the activity of the nuclease is substantially less in the unheated serum.

Anfinsen, C. B. Catalytic properties and specificity of the extracellular nuclease of *Staphylococcus aureus*. J Biol Chem 242, 1541-1547 (1967)). The inventors postulated that heat treating human serum that contains micrococcal nuclease might result in inactivation of antibodies or other components that inhibit micrococcal nuclease while leaving micrococcal nuclease functional. To evaluate this idea, micrococcal nuclease was serially diluted into human serum that was previously dialyzed into a buffer containing 10 mM $CaCl_2$. Samples of each dilution were then either heat treated or untreated. Supernatants of centrifuged, heat treated serum were then compared side-by-side with untreated serum in a nuclease activity assay with a quenched fluorescent oligonucleotide probe. As shown in FIG. 12, this heat protocol unmasked micrococcal nuclease activity in the serum, with the effects being most evident at the lower concentrations of the nuclease.

The expectation that very low concentrations of the nuclease are present in the blood of patients with *S. aureus* bacteremia provided a rationale for the pursuit of further increases in assay sensitivity. One approach is to purify and concentrate the nuclease from serum specimens prior to incubation with the nuclease probes. Affinity-based approaches were evaluated for nuclease concentration because these can be rapid and also provide an additional degree of specificity for micrococcal nuclease over non-target nucleases. A custom monoclonal antibody for micrococcal nuclease was produced (Pierce Biotechnologies). The supernatants of several hybridoma clones were screened to identify those that produced antibodies that could effectively immunoprecipitate micrococcal nuclease without inhibiting its activity. Next, a purified rat monoclonal antibody with these desired properties was obtained. After using this antibody with magnetic protein G-coupled beads to immunoprecipitate micrococcal nuclease from dilute solutions, the nuclease-bound beads were incubated directly (i.e., in suspension) with nuclease probes and robust probe activation was observed. This indicated not only that the nuclease was effectively immunoprecipitated, but that it retained its activity while bound to the antibody. The fact that the nuclease is functional when bound to the antibody allowed the elimination of a nuclease elution step prior to probe digestion, thus providing for a more rapid assay.

Figure 13:
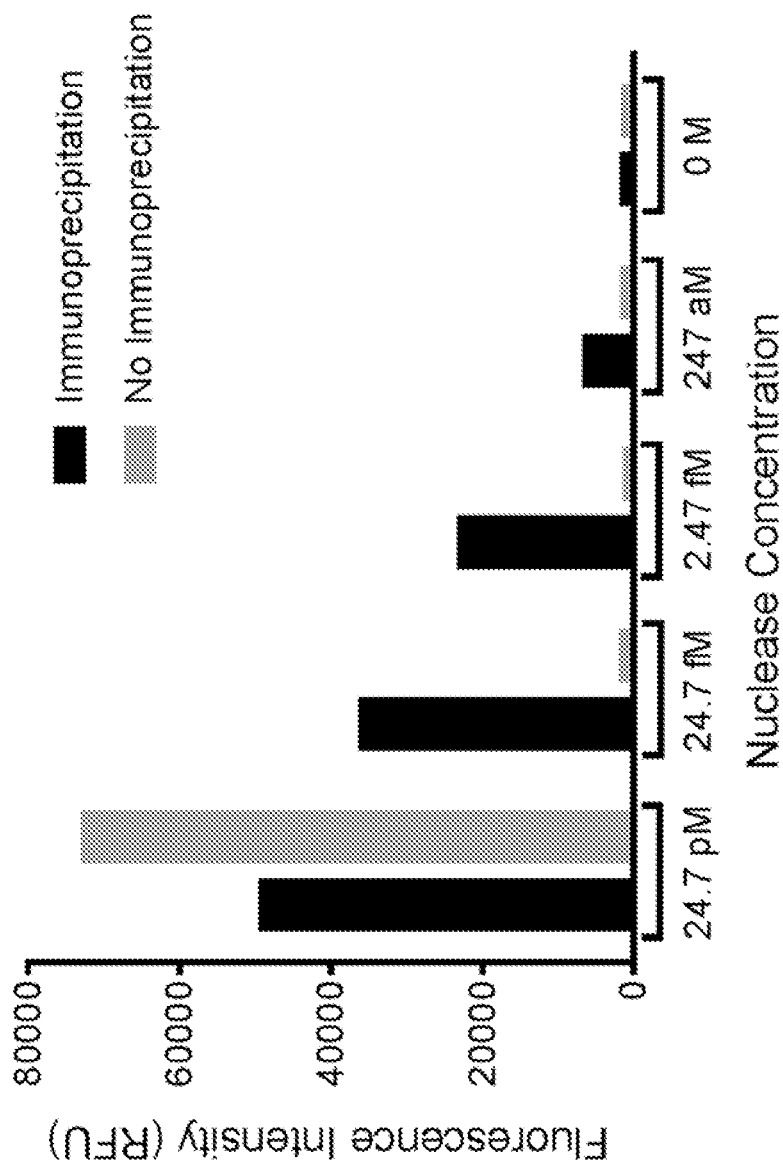
FIG. 13. Increased sensitivity of nuclease activity assay via immunoprecipitation of micrococcal nuclease. Micrococcal nuclease was added to heparinized human plasma (pooled from healthy donors) to yield the concentrations indicated above. The plasma samples were heated, centrifuged and supernatants were divided into two groups. In one set of samples, the supernatants were incubated directly with the PolyTT probe prior to plate-reader fluorescence measurements. In the other set of samples, micrococcal nuclease was immunoprecipitated onto antibody-protein G-coupled magnetic beads; the beads were then incubated with the PolyTT probe in suspension prior to plate-reader fluorescence measurement of the liquid supernatant of this suspension. Note that concentrations of micrococcal nuclease as low as 247 attomolar (aM) could be distinguished from the background levels seen with no nuclease added (0 M) in the immunoprecipitated samples.

The sensitivity of an assay for micrococcal nuclease was then evaluated in which human plasma containing various amounts of the nuclease was first heat treated and then subjected to immunoprecipitation, followed by probe incubation. The dialysis step used in the initial evaluation of the heating protocol was circumvented by spiking calcium chloride directly into the plasma prior to heating. With a one hour precipitation step and a one hour probe incubation step, this assay took a total of less than three hours. Immunoprecipitation of the nuclease after heating provided a robust improvement in assay sensitivity over heating alone, as shown in FIG. 13. In particular, samples that were only heat-treated yielded background fluorescence levels (i.e., levels of the no nuclease control samples) with micrococcal nuclease concentrations of 24.7 femtomolar or less while heat-treated and immunoprecipitated samples yielded levels above background levels with nuclease concentrations as low as 247 attomolar.

Next, it was sought to demonstrate the efficacy of the assay as a diagnostic for *S. aureus* bacteremia. Heparinized plasma specimens were obtained from two groups of individuals. The first group had *S. aureus* bacteremia, as confirmed by conventional blood culturing methods carried out at the University of Iowa Hospital. Table 4 lists the time elapsed between the initiation of these blood cultures and detection of bacterial growth in them; this time-to-positive value is considered a rough indication of the bacterial load in the blood, with shorter times indicative of larger bacterial loads.

TABLE 4

| Specimen ID | Time to Positive |
| --- | --- |
| K | Aerobic - 15 hr, 37 min |
|   | Anaerobic - 15 hr, 37 min |
| G | Aerobic - 17 hr, 53 min |
| J | Anaerobic - 19 hr, 15 min |
| M | Aerobic - 20 hr, 11 min |
| P | Aerobic - 20 hr, 15 min |
| V | Aerobic - 1 day, 5 hr, 28 min |
| B | Aerobic - 1 day, 5 hr, 53 min |
| D | Aerobic - 1 day, 9 hr, 26 min |
| U | Aerobic - 2 days, 10 hr, 25 min |
| A | Presumed Negative; Not Tested |
| F | Presumed Negative; Not Tested |
| H | Presumed Negative; Not Tested |
| I | Presumed Negative; Not Tested |
| L | Presumed Negative; Not Tested |
| N | Presumed Negative; Not Tested |
| R | Presumed Negative; Not Tested |
| S | Presumed Negative; Not Tested |
| T | Presumed Negative; Not Tested |

Figure 14:
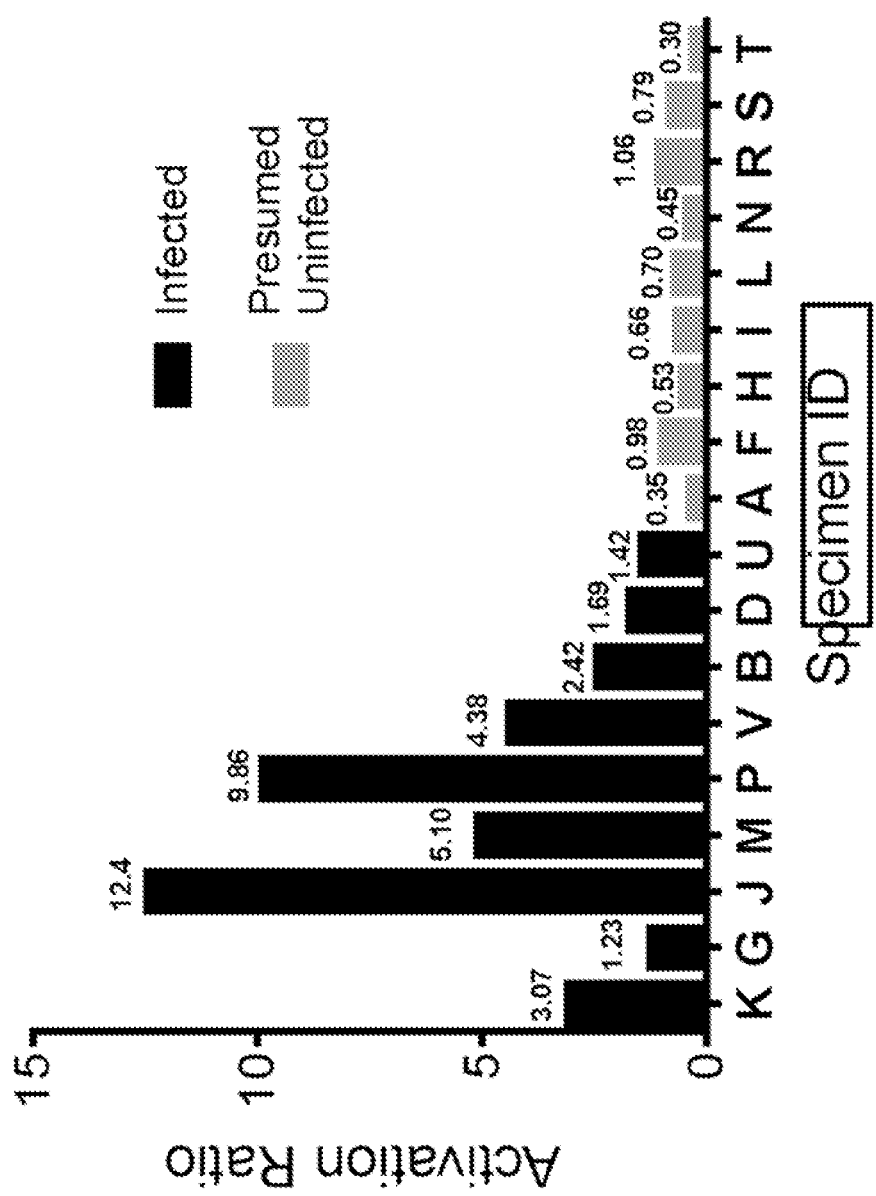
FIG. 14. Detection of micrococcal nuclease in plasma of patients with *S. aureus* bacteremia. Nuclease activity assays were carried out with plasma specimens from *S. aureus* bacteremic (Infected) and individuals showing no signs of active infections (Presumed Uninfected). Micrococcal nuclease was immunoprecipitated from supernatants of heated and centrifuged plasma specimens. The immunoprecipitated material was incubated with the PolyTT quenched fluorescent oligonucleotide probe and fluorescence was measured with a plate-reader. All fluorescence values were divided by that of a control sample in which buffer was substituted for plasma to yield the Activation Ratios. Data shown are compiled from several independent experiments.

Information on the specimens used in FIG. 14. "Time-to-Positive" indicates the time elapsed for the blood cultures of the same patients to indicate bacterial growth.
Note:
both aerobic and anaerobic cultures are prepared. In cases where only one of these became positive, only the positive value is included.
"Presumed Negative" indicates that these specimens were drawn from individuals that were not exhibiting signs of active infections; no blood cultures were prepared from these individuals.

It is important to note that the blood used to prepare the plasma for the assays was drawn on the same day as the blood drawn for the diagnostic blood cultures. The second group of individuals was selected as control subjects based on the fact that they were not exhibiting any signs of active infections. Because diagnostic culturing assays were not carried out for these individuals, the plasma from them was classified as "presumed uninfected."

A total of nine *S. aureus* positive (infected) and nine negative (presumed uninfected) human plasma specimens were tested in five distinct experiments. The data from these experiments is compiled in FIG. 14. Note that the fluorescence values of the plasma samples were normalized by dividing by the values of "no plasma" control samples which were included in each experiment to yield "activation ratios." These ratios demonstrate a clear difference between the infected and presumed uninfected specimens as all of the infected ratios are higher than all of the presumed uninfected ratios. Collectively, the infected plasma specimens have an average ratio that is seven-fold greater than that of the presumed uninfected specimens. In summary, a rapid (<3 hours) nuclease activated probe-based assay has been developed that can detect the presence of *S. aureus* in clinical human plasma specimens of bacteremic patients, and therefore forms the basis of a valuable clinical diagnostic assay for *S. aureus* bacteremia.

Methods

PolyTT Quenched Fluorescent Probe

PolyTT is an 11-mer DNA probe with a sequence of /6-FAM/TTTTTTTTTTT/ZEN/IAbRQSp/(SEQ ID NO: 5), where 6-FAM is a fluorophore (fluorescein amidite), the T's indicate deoxythymidine (DNA) nucleotides, ZEN is the ZEN dark quencher, and IAbRQSp is the Iowa Black dark quencher. The probe sequence is listed from the 5'- to the 3'-end. Its molecular weight is 4942.6 Da. The polyTT probe was synthesized and HPLC purified by Integrated DNA Technologies (IDT) of Coralville, Iowa Upon receipt of the lyophilized probe from IDT, the probe was either stored directly at −80° C. or dissolved in TE (Ambion catalogue #: AM9849-10 mM Tris-HCl pH 8.0 and 1 mM EDTA) to a final concentration of 500 μM, aliquoted into 1 μl volumes, and then stored at −80° C. This probe serves as a substrate for micrococcal nuclease of S. aureus.

Evaluation of Heat Protocol in Human Serum

To evaluate the thermostability of micrococcal nuclease, non-target nucleases and inhibitory antibodies in serum, human serum pooled from healthy donors was used (Bioreclamation IVT catalogue #: HMSRM, pooled human serum, no filtration). Serum specimens were dialyzed prior to experiments as follows. 110 μl serum was dialyzed against 1.4 ml of 50 mM Tris-HCl pH 9.0, 10 mM $CaCl_2$ (prepared from Sigma catalogue #: T2819—1 M Trizma hydrochloride solution, pH 9.0 and Sigma catalogue #: 21115—1 M $CaCl_2$ solution) on a rocker at 4° C. for 2 hours with a microdialysis tube (Pierce Biotechnology, Inc. catalogue #: 88262, 96-well Microdialysis Plate 3.5K MWCO). The dialysis buffer was exchanged for fresh buffer and the serum was then dialyzed for a second 2 hour period. This dialysis protocol was replaced with alternative methods in some experiments as described in Preparation of Plasma Samples from S. aureus Bacteremic Patients and Control Subjects. Because the serum used here was not infected, it did not initially contain any micrococcal nuclease. Defined amounts of a pure preparation of micrococcal nuclease were added to the dialyzed serum to evaluate the thermostability of the enzyme. Prior to addition to serum, the pure nuclease was pre-diluted into 50 mM Tris-HCl pH 9.0, 10 mM $CaCl_2$ from a 10 unit/pi stock solution (purified micrococcal nuclease was obtained from Worthington catalogue #: LS004798—Nuclease, Micrococcal 45 ku; stock buffer consisted of 50% glycerol, 50% DPBS, prepared from Gibco catalogue #: 14190-144—Dulbecco's phosphate-buffered saline, no calcium, no magnesium). 11.1 μl of each micrococcal nuclease dilution was added to 100 μl of dialyzed serum in a 1.5 ml low protein binding microfuge tube (Eppendorf catalogue #: 022431081—Protein LoBind Tube 1.5 ml). A "no nuclease" control sample was prepared with 11.1 μl of 50 mM Tris-HCl pH 9.0, 10 mM $CaCl_2$ buffer and 100 μl of dialyzed serum. Samples were divided in half, with one half to undergo the heating protocol and the other half to be reserved as unheated controls. The unheated control samples were placed at 4° C. during the heating protocol. The other samples were then placed in a 90° C. heat block for 20 minutes. The heated serum samples, which became cloudy upon heating due to protein precipitation, were then centrifuged at 17,000×g for 10 minutes. 1 μl of polyTT probe (synthesized and purified by IDT, see PolyTT Quenched Fluorescent Probe for description) diluted to a concentration of 50 μM in 50 mM Tris-HCl pH 9.0, 10 mM $CaCl_2$, was then added to 9 μl of each heat-processed human serum supernatant and unheated control human serum sample. The tubes were incubated in the dark at 37° C. for 1 hour. To stop the digestion by micrococcal nuclease, which requires calcium for activity, 290 μl of 10 mM EDTA and 10 mM EGTA in DPBS (prepared from Ambion catalogue #: AM9260G—0.5 M EDTA pH 8.0, Bio-World Catalogue #: 40520008-1—0.5 M EGTA pH 8.0, and Gibco catalogue #: 14190-144—Dulbecco's phosphate-buffered saline, no calcium, no magnesium) was added to each tube. The stopped reactions were mixed by pipetting up and down, and then 90 μl was transferred to each of 3 wells of a 96-well plate (Thermo Scientific catalogue #: 237105—Nunc F96 MicroWell Black Polystyrene Plate) for triplicate readings. Fluorescence was measured in a fluorescence plate-reader (Analyst HT or Biotek Synergy Mx) at 485/530 nm excitation/emission.

Preparation of Plasma Samples from S. aureus Bacteremic Patients and Control Subjects Heparinized plasma specimens obtained from patients with confirmed S. aureus bacteremia or from individuals exhibiting no signs of active infections, were provided by the University of Iowa Tissue Procurement Core Facility. These specimens were aliquoted into 110 μl volumes and stored at −80° C. For the assays, six aliquots of each specimen were thawed at 25° C. and combined into a single 660 μl sample in a 1.5 ml low protein binding microfuge tube. To enable micrococcal nuclease thermostability, 6.7 μl of 1 M $CaCl_2$ solution (Sigma catalogue #: 21115—1 M $CaCl_2$ solution) was added to the plasma, yielding a final concentration of approximately 10 mM $CaCl_2$. Samples were then placed in a 90° C. heat block for 20 minutes. The plasma samples, which became cloudy upon heating due to protein precipitation, were then centrifuged at 17,000×g for 10 minutes. Supernatants were transferred to fresh tubes and used for the subsequent immunoprecipitation/nuclease assay.

For comparison of assay sensitivity with and without the immunoprecipitation step, 100 μl of various dilutions of micrococcal nuclease diluted in 50 mM Tris-HCl pH 9.0, 10 mM $CaCl_2$ and 11 μl of 1 M $CaCl_2$ were added to 1 ml of pooled human plasma (Bioreclamation IVT catalogue #: HMPLLIHP, pooled human plasma, lithium heparin anticoagulant, no filtration). The samples were heated and centrifuged as described above and 500 ul of each supernatant was used for subsequent immunoprecipitations or supernatants were used directly in nuclease assays.

Immunoprecipitation of Micrococcal Nuclease from Plasma

Protein G-coupled magnetic beads (Life Technologies catalogue #: 10004D—Dynabeads Protein G for Immunoprecipitation) were resuspended in the manufacturer's vial by rotating the vial at room temperature for 5 minutes. For each plasma sample, 40 μl of the beads suspension was added to an empty 1.5 ml low protein binding microfuge tube. An additional tube was prepared in the same way in parallel for use as a "no plasma" control. The tubes were placed on a magnet for ~1 minute to separate the beads from the manufacturer's storage solution, and the solution was removed with a pipette. The beads were resuspended in 1 ml of 0.02% Tween-20 in DPBS (wash buffer). This was prepared from Amresco catalogue #: 0777—Tween-20 Reagent Grade and Gibco catalogue #: 14190-144—Dulbecco's phosphate-buffered saline, no calcium, no magnesium. The tubes were then placed on the magnet to separate the beads from the wash buffer, and the buffer was removed with a pipette. This washing step (re-suspending beads in wash buffer and removing wash buffer) was repeated once for a total of two washes. 50 μl of anti-micrococcal nuclease monoclonal antibody (Pierce Biotechnology, Inc. custom produced antibody, stored in 50% glycerol at 0.75 mg/ml) was diluted with 450 μl wash buffer and used to resuspend the beads in each beads-containing tube. The tubes were incubated with beads and antibody on a rotator at room temperature for 1 hour and then placed on the magnet to separate the beads from the antibody solution. The solution was removed with a pipette. The beads were then washed with wash buffer twice as described above. Next, each heat-processed human plasma supernatant (prepared as described in Preparation of *Plasma Samples from S. aureus Bacteremic Patients and Control Subjects*) was added to an antibody/beads-containing tube. The entire supernatant from each of these samples was used; the volume varied from approximately 300 to 350 μl. 350 μl of 50 mM Tris-HCl pH 9.0, 10 mM CaCl$_2$ was added to the beads-containing tube reserved for the "no plasma" control. For the side-by-side comparison of the assay sensitivity with and without immunoprecipitation, 500 ul of each supernatant was used. The tubes were incubated on a rotator at room temperature for 1 hour. Next, the tubes were placed on a magnet to separate the beads from the heat-processed plasma supernatants or buffer solution, and the solutions were removed with a pipette. The beads were then washed with 1 ml wash buffer (as described above) a total of 3 times, using a fresh low protein bind tube for each wash. The beads were then washed twice with 1 ml 50 mM Tris-HCl pH 9.0, 10 mM CaCl$_2$, using a fresh low protein bind tube each time.

Fluorescence Plate-Reader Assay for Immunoprecipitated Micrococcal Nuclease

Probe incubation reactions and plate-reader measurements of immunoprecipitated nuclease samples were carried out as follows. Each bead sample (prepared as described in Immunoprecipitation of Micrococcal Nuclease from Plasma) was resuspended in 60 μl 50 mM Tris-HCl pH 9.0, 10 mM CaCl$_2$. 1 μl of polyTT probe (synthesized and purified by IDT, see PolyTT Quenched Fluorescent Probe for description) diluted to a concentration of 50 μM in 50 mM Tris-HCl pH 9.0, 10 mM CaCl$_2$, was then added to each beads suspension. The tubes were incubated with probe on a rotator at room temperature in the dark for 1 hour. The tubes were then placed on a magnet, separating beads from probe solution, and 50 μl of each probe-containing supernatant was transferred to a well of a 96-well plate (Thermo Scientific catalogue #: 237105—Nunc F96 Micro Well Black Polystyrene Plate). Fluorescence was measured in a fluorescence plate-reader (Analyst HT or Biotek Synergy Mx) at 485/530 nm excitation/emission.

Example 5

Degradation of Nuclease-Stabilized RNA Oligonucleotides in *Mycoplasma*-Contaminated Cell Culture Media Artificial RNA reagents such as siRNAs and aptamers often must be chemically modified for optimal effectiveness in environments that include ribonucleases. Mycoplasmas are common bacterial contaminants of mammalian cell cultures that are known to produce ribonucleases. Here, the inventors describe the rapid degradation of nuclease-stabilized RNA oligonucleotides in an HEK cell culture contaminated with *Mycoplasma fermentans*, a common species of *Mycoplasma*. RNA with 2'-fluoro- or 2'-O-methyl-modified pyrimidines was readily degraded in conditioned media from this culture, but was stable in conditioned media from uncontaminated HEK cells. RNA completely modified with 2'-O-methyls was not degraded in the *Mycoplasma* contaminated media. RNA zymogram analysis of conditioned culture media and material centrifuged from the media revealed several distinct protein bands (ranging from 30 to 68 kDa) capable of degrading RNA with 2'-fluoro- or 2'-O-methyl-modified pyrimidines. Finally, the *Mycoplasma*-associated nuclease was detected in material centrifuged from the contaminated culture supernatants in as little as 15 minutes with an RNA oligo containing 2'-O-methyl-modified pyrimidines and labeled with a 5'-FAM and 3'-quencher. These results suggest that *Mycoplasma* contamination may be a critical confounding variable for cell culture experiments involving RNA-based reagents, with particular relevance for applications involving naked RNA (e.g., aptamer-siRNA chimeras).

Synthetic RNA that is exposed to cells or tissues must be protected from ribonuclease degradation in order to carry out its intended function in most cases. Common approaches for avoiding nuclease degradation include nanoparticle encapsulation which insulates the RNA from exposure to ribonucleases and chemical modification to render it resistant to degradation. Modification of RNA by substituting O-methyl or fluoro groups for the hydroxyl at the 2'-position of the ribose can greatly enhance its stability in the presence of extracellular mammalian ribonucleases.

These modifications are widely employed in the development of siRNAs and RNA aptamers for both research and therapeutic applications. siRNAs can be modified with 2'-O-methyl substitutions in both sense and antisense strands without loss of silencing potency, but only a subset of nucleotides are typically modified with 2'-O-methyls as over-modification of the siRNA can reduce or eliminate its silencing ability. siRNAs with 2'-fluoro modified pyrimidines have also been reported to retain silencing activity in vitro as well as in vivo.

RNA with 2'-fluoro modified pyrimidines is the most commonly used chemistry for development of RNA aptamers with potential therapeutic applications. Such RNA is stable in animal serum and can also be efficiently transcribed in vitro with a mutant viral RNA polymerase, thus facilitating its use in the aptamer discovery process known as SELEX (Systematic Evolution of Ligands by EXpontential enrichment). The stability of this RNA in other contexts such as conditioned cell culture media has not been well-studied.

Mycoplasmas are a genus of small bacteria that are common contaminants of cell cultures. They lack a cell wall, are not susceptible to the antibiotics usually employed in cell culture and often go undetected in cell culture due to their small size. Some *Mycoplasma* species, notably *Mycoplasma pneumoniae*, are human pathogens. Various *Mycoplasma* species are known to produce ribonucleases and deoxyribonucleases; however, the ability of these nucleases to degrade chemically modified RNA formulations has not been explored prior to the present work.

The inventors evaluated the stability of RNA with 2'-fluoro modified pyrimidines in cell culture media conditioned by human embryonic kidney 293 (HEK) cells and found the RNA to be substantially degraded after fairly brief incubations. It was subsequently determined that the HEK cells were contaminated with *Mycoplasma*, and it was investigated whether this contamination was responsible for the observed nuclease activity.

Materials and Methods

Cell Culture and Conditioned Media. HEK cells were inadvertently contaminated with *Mycoplasma* at some point during routine culture maintenance. The contamination was later detected and confirmed by PCR to be *Mycoplasma fermentans*. This *Mycoplasma* contaminated cell line was used as a positive control for *Mycoplasma* testing methods. Uncontaminated HEK cells were obtained from ATCC (ATCC-CRL-1573™). Contaminated and uncontaminated HEK cells were grown in DMEM (GIBCO) containing 10% heat-inactivated bovine serum, 50 U/ml penicillin, and 50 μg/ml streptomycin at 37° C., 5% CO$_2$ in a moist atmosphere. For preparation of conditioned media, contaminated or uncontaminated HEK cells were grown to ~80% confluency on 100 mm or 150 mm culture dishes. The culture media was then replaced with fresh media. After 48 hours of incubation, the media was centrifuged for 6 minutes at 1,250 rpm in a table-top centrifuge to remove cellular debris. Finally, the supernatant was transferred into a fresh tube and used as "conditioned media." Unconditioned media had the same composition (see above), but was not incubated with cells. Particulate matter was centrifuged from such conditioned media for the experiments described in FIG. 15C. 6 milliliters of conditioned media was centrifuged at 13,300 rpm in a microcentrifuge. The pellet was washed with PBS and then dissolved in 20 µl 1% Triton X-100 in PBS. Eppendorf tubes with these reactions were imaged with a digital camera and UV-light trans-illumination.

*Mycoplasma* Culture.

*Mycoplasma* broth consisted of 10% yeast extract solution (Gibco), 20% heat-inactivated fetal bovine serum, 70% heart infusion broth (BD Biosciences), 50 U/ml penicillin, and 50 µg/ml streptomycin. A freeze-dried culture of *Mycoplasma fermentans* (ATCC #15474) was rehydrated in 10 ml of *Mycoplasma* broth. Several 10-fold serial dilutions of this culture were then prepared and the bacteria were grown in 50 ml conical tubes at 37° C. for several days. For the experiment shown in FIG. 16, 1 ml of *Mycoplasma fermentans* culture grown for 5 days was pelleted at 13, 3000 rpms for 5 minutes. Supernatant was discarded and the lysate was prepared by dissolving the pellet in 20 µl 1% Triton X-100 in PBS. The lysate was incubated with RNAse substrates for 1 hour at 37° C.

Chemically Modified RNA.

The following 51 nucleotide long RNA sequence was used for the gel-based degradation assays and the RNA zymograms: 5'-GGGAGGACGAUGCGGGACUAGC-GAUCUGUUACGCACAGACGACUCGCCCGA-3' (SEQ ID NO: 34). Several versions of this RNA, with modifications as described in figure legends and the results section were used. FAM (fluorescein amidite)-labeled versions were used in the gel-based degradation assays, whereas non-fluorescent versions were used for the zymograms. These RNAs were obtained from Trilink Biotechnologies (San Diego, Calif.).

Gel-Based Degradation Assay.

For each degradation assay sample, 6 µl of oligo (2 µM) was combined with 6 µl of unconditioned and conditioned media and incubated for 0.5, 1, 2, or 4 hours at 37° C. After incubation, samples were combined with 12 µl of loading buffer (formamide with 0.5×TBE), incubated for 6 minutes at 65° C., transferred to ice for 5 minutes, briefly centrifuged and kept on ice until loading. Samples were run on a 7.7 M Urea/10% acrylamide gel at 100 volts for 80 minutes. Gel images were acquired with a Gel Doc™ XR+ System (Bio-Rad) with ultraviolet light transillumination and a standard fluorescence filter for imaging ethidium bromide.

RNAse Substrate Plate-Reader Assays.

The RNAse substrates were synthesized by Integrated DNA Technologies (IDT; Coralville, Iowa). These probes consist of a 12 nucleotide long RNA oligo, 5'-UCUCGUACGUUC-3' (SEQ ID NO: 6), with the chemical modifications indicated in figure legends, flanked by a FAM (5'-modification) and a pair of fluorescence quenchers, "ZEN" and "Iowa Black" (3'-modifications). For the RNA degradation assays, 1 µl of each RNAse substrate (50 picomoles) was combined with 9 µl of sample (e.g., conditioned media) and incubated at 37° C. for time points indicated in the figures. After the incubation period, 290 µl of PBS supplemented with 10 mM EDTA and 10 mM EGTA was added to each sample and 95 µl of each sample was loaded in triplicate into a 96-well plate (96F non-treated black microwell plate (NUNC)). Fluorescence intensity was measured with a fluorescence microplate reader (Analyst HT; Biosystems). For the Triton X-100 lysate samples, the undiluted 10 µl reactions were imaged in eppendorf tubes with a Gel Doc™ XR+ System (Bio-Rad) with ultraviolet light transillumination and a standard fluorescence filter for imaging ethidium bromide.

PCR.

All cell cultures were tested for *Mycoplasma* infection by PCR. Four primer sets, previously described (Choppa, P. C., Vojdani, A., Tagle, C., Andrin, R., and Magtoto, L. (1998). Multiplex PCR for the detection of *Mycoplasma fermentans*, *M. hominis* and *M. penetrans* in cell cultures and blood samples of patients with chronic fatigue syndrome. Mol Cell Probes 12, 301-308), were used to identify a conserved region among all members of the genus *Mycoplasma* and three specific species: *Mycoplasma fermentans*, *Mycoplasma hominis* and *Mycoplasma penetrans*. *Mycoplasma*, centrifuged from conditioned cell culture media, provided the template DNA for the *Mycoplasma* specific PCRs. The *Mycoplasma* was isolated from the culture media as follows: conditioned media was centrifuged for 6 minutes at 1,250 rpm to pellet cellular debris. 2 ml of the supernatant from this spin were then centrifuged for 5 minutes at 17,000×g to pellet any *Mycoplasma* present in the media. The pellet was re-suspended in 50 µl of water; this served as the PCR template. The PCR reaction mixtures were prepared in a total volume of 100 µl containing 10 µl of PCR template, 2 µl dNTP's (10 µM), 1 µl of each primer (100 µM), 50 µl of Choice Taq Mastermix (Denville Scientific) and 36 µl of water. 30 cycles of PCR were carried out. The temperature steps were as follows: 94° C. for 5 minutes, 30× (denaturation at 94° C. for 30 seconds; annealing at 55° C. for 30 seconds; elongation at 72° C. for 30 seconds) a final extension step of 72° C. for 10 minutes was carried out at the completion of the cycling. The PCR products were analyzed on a 2% (w/v) agarose gel stained with 0.5 µg/ml ethidium bromide. The DNA bands were visualized with a Gel Doc™ XR+ System (Bio-Rad) with ultraviolet light transillumination and a standard fluorescence filter for imaging ethidium bromide.

DAPI Staining.

*Mycoplasma* was visualized in cultured cells via DAPI (4',6-diamidino-2-phenylindole, dihydrochloride, Invitrogen) staining. Briefly, HEK cells were grown on glass bottomed culture dishes from MatTek (Ashland, Mass.). Cells were then fixed by incubation for 20 minutes at −20° C. in 100% methanol and stained with DAPI following the protocol provided in the DAPI product insert. The cells were then rinsed several times in PBS and fluorescence was visualized with an Olympus IX71 fluorescence microscope equipped with a 40× oil-immersion objective, fluorescence filters appropriate for DAPI and a cooled CCD digital camera.

DNA Zymograms.

*Mycoplasma*-free and *Mycoplasma*-positive cell cultures were serum-starved for 48 hours on 150 mm culture dishes in 20 ml of DMEM. Media was collected, spun at 1,250 rpms for 6 minutes to eliminate cell debris, then spun at 17,000×g for 5 minutes to pellet *Mycoplasma* from the conditioned media. These pellets were solubilized in 50 µl SDS sample loading buffer. The supernatants from the second centrifugation were concentrated with a YM-10 Amicon centrifugal filter device (MW cutoff of 10 kDa) to a final volume of approximately 100 µl. One or 3 µl of the concentrated media or pellet, respectively, were loaded per lane of an 8% acrylamide SDS gel containing 200 µg/ml salmon sperm DNA (Invitrogen). After the gel was run, nucleases were activated by a series of 10 minute washes: 2 washes in 2 mM CaCl$_2$, 2 mM MgCl$_2$, 2.5% Triton X-100 in water; 2 washes in 2 mM CaCl$_2$, 2 mM MgCl$_2$, 2.5% Triton X-100 in 50 mM Tris-HCl (pH 7.4); 2 washes in 2 mM CaCl$_2$, 2 mM MgCl$_2$ in 50 mM Tris-HCl (pH 7.4). The gels were then incubated in 2 mM CaCl$_2$, 2 mM MgCl$_2$ in 50 mM Tris-HCl (pH 7.4) for either 2 hours or overnight at 37° C. The gels were stained with 0.5 µg/ml ethidium bromide and visualized with a Gel Doc™ XR+ System (Bio-Rad) with ultraviolet light transillumination and a standard fluorescence filter for imaging ethidium bromide.

Chemically Modified RNA Zymograms.

Samples were prepared as for the DNA zymograms (described above). Proteins were separated on 8% acrylamide SDS gels polymerized with either 550 nM of an RNA oligo with 2'-fluoro-modified pyrimidines or 250 nM of an RNA oligo with 2'-O-methyl-modified pyrimidines. See "Chemically Modified RNA" above for the sequence of these oligos. Gels were washed as above, but stained with a 1:10,000 dilution of Sybr Gold nucleic acid gel stain (Invitrogen) and visualized with a Gel Doc™ XR+ System (Bio-Rad) with ultraviolet light transillumination and a standard fluorescence filter for imaging ethidium bromide.

Results

To evaluate the stability of RNA with 2'-fluoro modified pyrimidines in conditioned culture media, a 51 nucleotide RNA with 2'-fluoro modified pyrimidines (underlined) and a 3'-FAM (5'-GGGAGGA<u>C</u>GA<u>U</u>G<u>C</u>GGGA<u>CU</u>AG<u>C</u>GA<u>UCUGUUAC</u>G<u>C</u>A<u>C</u>AGA<u>C</u>GA<u>CUC</u>G<u>CCC</u>GA-3'-FAM (SEQ ID NO:35)) was incubated in serum-containing media, conditioned with an HEK cell culture recently obtained from ATCC, or with an older HEK cell culture. As previously reported, this RNA was found to be resistant to nuclease degradation in the presence of animal serum. While the modified RNA was also stable in conditioned media from the HEK cells obtained from ATCC, the conditioned media from the older HEK cells almost completely degraded it after a 4-hour incubation at 37° C. The RNA was then resolved on a urea/acrylamide denaturing gel and imaged with a digital camera and UV-light trans-illumination; the oligo was labeled on its 3'-end with FAM. PCR primer sets specific for genomic components of *Mycoplasma fermentans*, *Mycoplasma hominis*, *Mycoplasma penetrans*, or for a region of the *Mycoplasma* genome that is conserved within the genus, were used to amplify DNA present in conditioned culture media. Expected PCR product sizes are as follows: *Mycoplasma* genus PCR: 280 bp; *Mycoplasma fermentans*: 206 bp; *Mycoplasma hominis*: 170 bp; *Mycoplasma penetrans*: 470 bp. The PCR assay for the presence of *Mycoplasma* detected a DNA sequence conserved within the genome of the *Mycoplasma* genus in the culture supernatant of the older HEK cell culture supernatant, but not in the media from the more recently obtained culture. A DNA sequence specific to the *Mycoplasma fermentans* species was also detected in media from the older HEK cell culture, as indicated with a PCR product of expected size. Sequencing of this PCR product confirmed that the amplified sequence is derived from the *Mycoplasma fermentans* genome. In contrast, neither *Mycoplasma hominis* nor *Mycoplasma penetrans* was detected.

As an additional means of detecting *Mycoplasma*, DAPI staining of HEK cells from these two cultures was carried out. Small, punctate, extra-nuclear DAPI-labeling, indicative of *Mycoplasma* contamination, was seen throughout the older HEK culture, but only nuclear labeling was seen in the culture obtained from ATCC. Together, these data demonstrate the presence of a ribonuclease that readily degrades RNA with 2'-fluoro modified pyrimidines in a *Mycoplasma*-contaminated but not in a *Mycoplasma*-free HEK cell culture.

Next, the activity of this ribonuclease after heat pre-treatment was studied, in the presence of EDTA (a chelator of divalent cations) and in the presence of a broad-spectrum ribonuclease inhibitor. The same RNA oligo initially examined was used for this experiment (51-mer with 2'-fluoro-modified pyrimidines and a 3'-FAM) with conditioned media from the *Mycoplasma*-contaminated HEK cells. Results of this experiment indicate that the ribonuclease activity is sensitive to heat treatment and is thus likely protein in nature. Like many ribonucleases, its activity is dependent on divalent cations as chelation of divalent cations with EDTA inhibited degradation of the modified RNA. To determine the dependence of the nuclease activity on divalent cations, conditioned media was incubated with RNA in the presence of 10 mM EDTA. A broad-spectrum RNAse inhibitor, Superase.in, was co-incubated (at 1 unit/µl) with the RNA in conditioned media to determine the sensitivity of the nuclease activity to this reagent. The RNA was resolved on a urea/acrylamide denaturing gel and imaged with a digital camera and UV-light trans-illumination; the oligo is labeled on its 3'-end with FAM. The broad-spectrum RNAse inhibitor, Superase.in, did not have an apparent impact on the activity.

While the 2'-fluoro nucleotide modification is widely used for the development of RNA aptamer-based therapeutic approaches, other modifications are more commonly used to protect synthetic RNAs in other applications such as RNAi. The 2'-O-methyl modification is widely employed and we thus examined the susceptibility of RNA with 2'-O-methyl-modified nucleotides to degradation by the *Mycoplasma*-associated ribonuclease activity. For this experiment, 3 RNA oligos were used. Each was 51 nucleotides in length, of identical sequence and with a 3'-FAM. The first oligo had 2'-fluoro-modified pyrimidines (purines were unmodified) (described above), the second had 2'-O-methyl-modified pyrimidines (purines were unmodified) and every nucleotide of the third oligo was modified with 2'-O-methyls. Co-incubation of these oligos with media conditioned by the *Mycoplasma*-contaminated HEK cells for 30 minutes, 1 hour, 2 hours or 4 hours again demonstrated the near-complete degradation of the oligo with 2'-fluoro-modified pyrimidines. The oligo with 2'-O-methyl-modified pyrimidines was more resistant to degradation, but was almost completely degraded after 4 hours. Finally, there was no detectable degradation of the oligo that was completely modified with 2'-O-methyls at any of the time-points.

Additional cell lines, contaminated with distinct *Mycoplasma* species (i.e., non-*Mycoplasma fermentans* species) were also tested for nuclease activity against RNA oligos with 2'-O-methyl- and 2'-fluoro-modified pyrimidines. Some of these cell lines possessed strong nuclease activity in their supernatants while others did not.

To further characterize the *Mycoplasma*-associated ribonuclease, zymograms were carried out with unmodified DNA or RNA with 2'-fluoro- or 2'-O-methyl-modified pyrimidines. For these experiments, serum-free conditioned cell culture media was used that was concentrated with filter centrifugation as well as detergent-lysed particulate matter centrifuged from the conditioned media. Concentrated media or material pelleted by centrifugation from media conditioned by *Mycoplasma*-free or *Mycoplasma* contaminated HEK cells was resolved on 8% acrylamide SDS gels embedded with DNA, RNA with 2% fluoro-modified pyrimidines or RNA with 2'-O-methyl-modified pyrimidines. After running, the gels were washed with SDS-free buffer containing divalent cations and incubated at 37° C. for 2 hours to allow nuclease digestion. The gels were stained with ethidium bromide (DNA zymogram) or SYBR Gold nucleic acid gel stain and imaged with a digital camera and UV-light trans-illumination, revealing protein bands with nuclease activity. The particulate matter presumably contains *Mycoplasma* in the contaminated culture sample and was also found to possess ribonuclease activity.

Multiple protein bands present in the *Mycoplasma*-contaminated, but not the *Mycoplasma*-free concentrated culture supernatants could be seen in all 3 zymograms. A cluster of bands that migrated between the 37 and 50 kDa molecular weight markers was prominent in these samples. A smaller protein, of approximately 30 kDa digested the modified RNAs; no digestion was seen in this region of the DNA zymogram. A larger protein, of approximately 68 kDa, produced a band in the DNA zymogram, but not in the modified RNA zymograms. However, longer digestion periods (e.g., overnight) did yield a band of approximately this size in the modified RNA zymograms. The prominent cluster of bands between 37 kDa and 50 kDa present in all of the zymograms suggests the presence of multiple nucleases with broad substrate specificities.

The detergent-lysed particulate matter produced a very different pattern of bands on the zymograms. As with the concentrated supernatant, dark bands indicating digestion were only seen in the sample prepared from the *Mycoplasma*-contaminated culture. However, the patterns of bands clearly indicate that there are multiple nucleases present in the particulate matter of the culture media with distinct substrate specificities. The prominent cluster of bands between the 37 kDa and 50 kDa molecular weight markers that was present in the concentrated culture supernatant was not seen in the particulate matter samples.

Because the *Mycoplasma*-associated nuclease can be distinguished from endogenous mammalian nucleases by its distinct substrate specificity, we reasoned that the presence of mycoplasmas, in various contexts, might be inferred by the susceptibility of chemically modified ribonuclease substrates to degradation. While gel-based assays provide a simple and straightforward means of detecting nuclease activity, a more rapid and sensitive assay for ribonucleases that degrade unmodified RNA has been described. The basis for this assay is a short oligonucleotide RNAse substrate, end-labeled with a fluorophore on one end that is rendered non-fluorescent by its close proximity to a quencher on the other end (FIG. 15A) (Kelemen, B. R., et al. (1999). Hypersensitive substrate for ribonucleases. *Nucleic Acids Res* 27, 3696-3701). Upon cleavage of the substrate, the quencher diffuses away from the fluorophore, which then exhibits fluorescence.

Figure 15B:
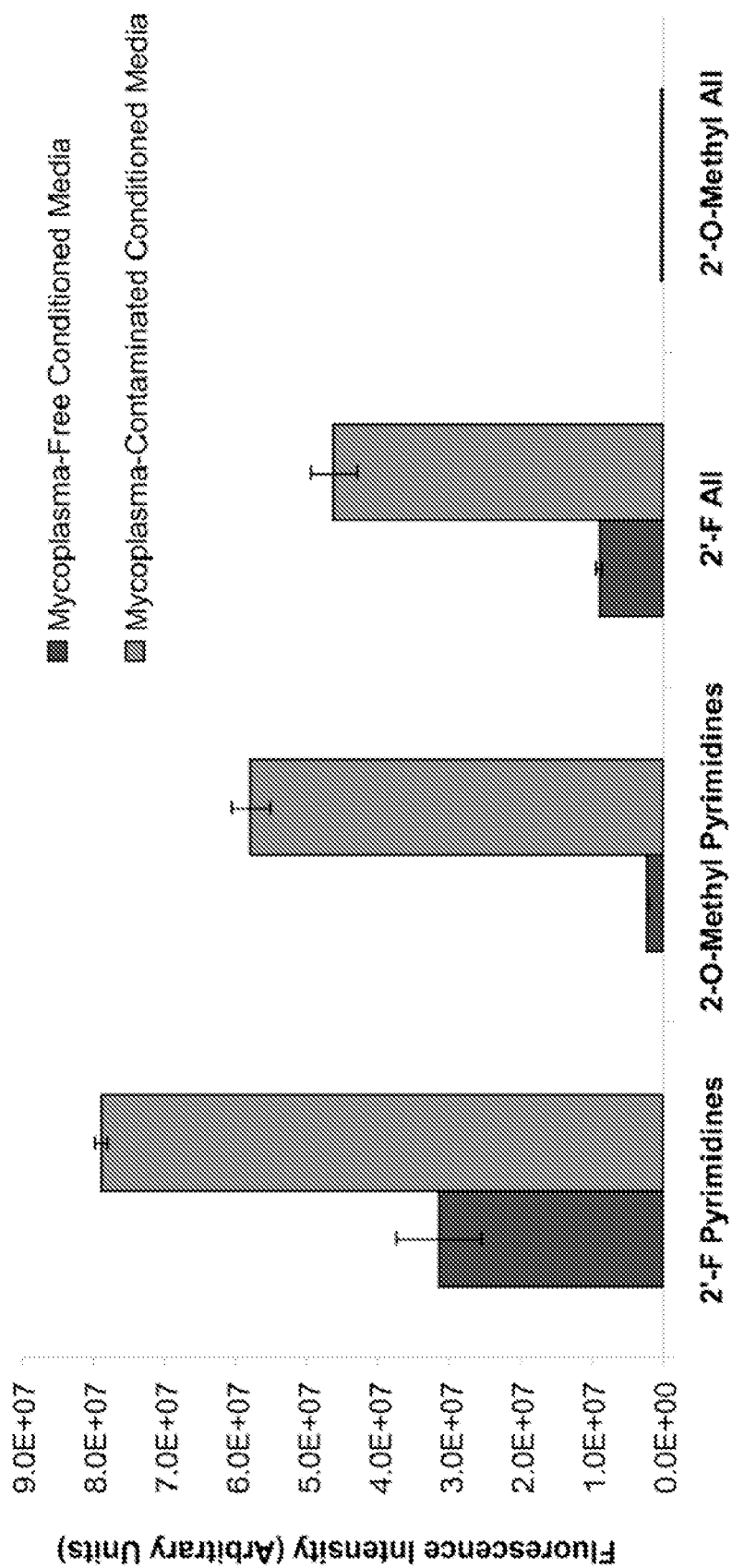

This approach was adapted to detect the *Mycoplasma*-associated nuclease by generating chemically modified RNAse substrates with fluorophore and quencher conjugates. Four different RNA chemistries were tested: 2'-fluoro-modified pyrimidines, 2'-O-methyl-modified pyrimidines, complete 2'-fluoro modifications, and complete 2'-O-methyl modifications. Initially, each of these RNAse substrates was incubated for 4 hours with culture media conditioned by either *Mycoplasma*-free or *Mycoplasma*-contaminated HEK cells (FIG. 15B). While the complete 2'-O-methyl-modified substrate was not digested in either media, the other 3 RNAse substrates exhibited substantially greater fluorescence after incubation in the *Mycoplasma*-contaminated media. Of these, the substrate with 2'-O-methyl-modified pyrimidines exhibited the greatest relative fluorescence increase between uncontaminated and contaminated media. This substrate was thus characterized further.

Centrifugation of particulate matter from the *Mycoplasma*-contaminated culture supernatants provided a simple and rapid means of obtaining concentrated nuclease activity. The possibility that this approach might increase the sensitivity of *Mycoplasma* detection with RNAse substrates was explored. The RNAse substrate with 2'-O-methyl-modified pyrimidines was incubated with a detergent lysate of centrifuged particulate matter from *Mycoplasma*-free or *Mycoplasma*-contaminated HEK cells for 1 hour (FIG. 15C). Conditioned media from these cultures was compared in parallel. While both the lysate and conditioned media exhibited strong nuclease activity, the lysate produced a greater signal in this assay. A clear signal could be seen over the background in this assay, even with an abbreviated (15 minutes) incubation (fluorescence was measured on an ultraviolet light box in this case).

Figure 16:
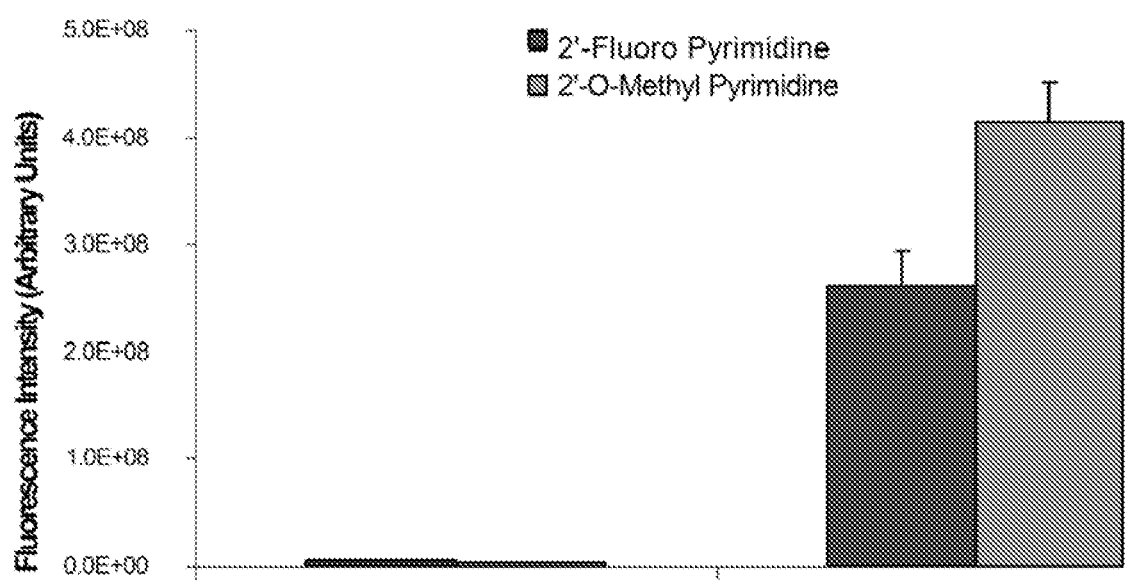
FIG. 16. 2'-Fluoro pyrimidine and 2'-O-methyl pyrimidine substrates with Triton X-100 lysate of *M. fermentans* bacteria.

The contaminated HEK cell culture is a complex preparation as it contains cells derived from two distinct organisms. While the uncontaminated HEK cells lack nuclease activity capable of efficiently degrading RNA with 2'-fluoro-modified or 2'-O-methyl-modified pyrimidines, we also sought to measure such activity in a pure culture of *Mycoplasma fermentans*. Consistent with the current observations of the contaminated HEK cell culture, lysates prepared from *Mycoplasma fermentans* bacteria exhibited robust nuclease activity against RNA substrates with 2'-fluoro-modified and 2'-O-methyl modified pyrimidines (FIG. 16). Nuclease activity against RNA substrates with 2'-fluoro-modified and 2'-O-methyl-modified pyrimidines was also found in the bacterial culture supernatant (not shown).

Discussion

It was found that conditioned media from HEK cells contaminated with *Mycoplasma fermentans* possesses ribonuclease activity that readily degrades RNA with 2'-fluoro-modified pyrimidines and 2'-O-methyl-modified pyrimidines. Comparable ribonuclease activity was seen in a pure culture of *Mycoplasma fermentans*, but not in an uncontaminated, HEK cell culture. These observations are consistent with the conclusion that the activity in the contaminated HEK cell culture is derived from the *Mycoplasma* bacteria. Zymograms with chemically modified RNA revealed the presence of multiple protein bands (from ~30 kDa to ~68 kDa) in the conditioned, *Mycoplasma*-contaminated culture media that possess this ribonuclease activity. Some of these proteins were found in particulate matter in the media, presumably containing free-floating *Mycoplasma*. RNAse substrates synthesized with chemically modified RNA detected the presence of this ribonuclease activity after a 15 minute incubation.

This work was undertaken to better understand the stability of chemically modified RNA oligonucleotides in cell culture settings. The results identify a critical variable for the use of RNA-based reagents in cell culture experiments. While the potential for *Mycoplasma*-based artifacts in cell culture experiments is widely known, many researchers do not regularly test their cell lines for mycoplasmas. Lack of regular testing is perhaps the primary reason that mycoplasmas continue to be problematic for cell culture studies. It is estimated that 15-35% of cell lines used are contaminated with mycoplasmas, with *Mycoplasma Fermentans* among the most prevalent species identified in cell lines.

The manner in which *Mycoplasma* contamination affects experimental outcome varies depending on the nature of the experiment. The present results suggest that experiments involving the application of naked RNA directly to cells are particularly vulnerable to *Mycoplasma*-dependent RNA degradation and experimental failure. These experiments include the study or application of siRNAs, RNA aptamers and ribozymes. For instance, the delivery of siRNAs by directly coupling them to targeting reagents such as antibodies, aptamers, peptides and other synthetic ligands all entail the application of naked RNA to cells. The evaluation of RNA aptamers targeting cell surface receptors or extracellular targets such as growth factors in cell culture, likewise, involves the application of naked RNA to cells.

The characterization of the *Mycoplasma*-associated ribonuclease activity with nucleic acid zymograms revealed the presence of multiple proteins with deoxyribonuclease and ribonuclease activity in the contaminated cell culture media. The presence of multiple bands in similar patterns in all 3 of the zymograms between the 37 kDa and 50 kDa molecular weight markers suggests that several nucleases capable of digesting DNA, or RNA with 2'-fluoro- or 2'-O-methyl-modified pyrimidines are produced by the *Mycoplasma*. Other bands found in the *Mycoplasma*-contaminated samples exhibited substrate specific degradation among the 3 nucleic acid chemistries tested. Altogether, the results from the zymograms suggest there are multiple *Mycoplasma*-derived ribonucleases present in the contaminated culture media that can readily degrade RNA with either 2'-fluoro- or 2'-O-methyl-modified pyrimidines. The identity of these proteins has not been determined. Because zymograms depend on protein refolding following SDS-denaturation, it is possible that some ribonucleases present in the culture media did not yield a signal on the zymograms.

The fraction of *Mycoplasma* species that produce ribonucleases capable of degrading chemically modified RNAs is uncertain. The fact that RNA oligos with 2'-fluoro- or 2'-O-methyl-modified pyrimidines were degraded in cultures contaminated with distinct, yet unidentified species of *Mycoplasma* indicates that the activity is not limited to the *Mycoplasma fermentans* species. Considering the diverse nature of mycoplasmas, it is perhaps not surprising that *Mycoplasma*-contaminated cell cultures that lacked such robust nuclease activity were found.

Because many mycoplasmas are human pathogens, the detection of *Mycoplasma*-derived nucleases has clinical diagnostic applications. DNAse activity has in fact been used to differentiate among various bacterial pathogens, including the identification of coagulase-positive staphylococci, such as *Staphylococcus aureus* in bovine milk samples. Such assays depend on the isolation of the bacteria from biological fluids and tissues that also contain DNAses, which would otherwise generate background; isolation and culture of the bacteria can consume valuable time. The use of chemically modified nucleic acids provides an alternative that could be used in more clinically relevant settings without generating background. Indeed, a chemically modified RNAse substrate that rapidly and robustly detected *Mycoplasma*-derived ribonuclease activity in serum-containing conditioned media was developed; digestion of this RNAse substrate in the same media conditioned by an uncontaminated culture was minimal. Chemically modified nucleic acids can thus facilitate the rapid determination of the presence of bacterial contamination.

Example 6

In Vivo Detection

The cleavage of oligonucleotides can be visualized in various ways, but as discussed above, the inventors favor flanking the sequences with a fluorophore and a quencher for rapid detection of the cleavage activity with a fluorometer. Advancing one step further, the inventors envision injecting the fluorescent probe into patients and using fluorescent detection to localize sights of infection (in addition to specific pathogen data) clearly within the patient. Preliminary data of this type has been established in mouse models. Briefly, mice were injected with micrococcal nuclease (purified *Staph. aureus* nuclease) in leg and injected with probe in tail vein. This procedure resulted in fluorescence being seen at site of nuclease and subsequently in liver.

Example 7

In Vitro Detection

Nuclease Probe Plate-Reader Assay: The nuclease probes were synthesized by Integrated DNA Technologies (IDT; Coralville, Iowa). These probes consist of a 12 nucleotide long RNA oligo, 5'-UCUCGUACGUUC-3' (SEQ ID NO:6), with the chemical modifications, flanked by a FAM (5'-modification) and a pair of fluorescence quenchers, "ZEN" and "Iowa Black" (3'-modifications. Three samples were assayed for degradation. PBS, 1 µl of each probe (50 picomoles) was combined with 9 µl of PBS. RNase A, 1 µl of each probe was combined with 8 µl of PBS and 1 µl RNase A (~50 U/µl). Micrococcal Nuclease (MN), 1 µl of each probe was combined with 8 µl of PBS and 1 µl of MN (10 U/µl). All the samples were incubated at 37° C. for 4 hours. After the incubation period, 290 µl of PBS supplemented with 10 mM EDTA and 10 mM EGTA was added to each sample and 95 µl of each sample was loaded in triplicate into a 96-well plate (96F non-treated black microwell plate (NUNC)). Fluorescence levels are shown in FIG. 16 (these are the PMT (photomultiplier tube) values). Fluorescence was measured with a fluorometer.

A nuclease from a third pathogenic bacterium, *Streptococcus pneumoniae*, has also been evaluated. A nuclease is expressed on the membrane of the *Streptococcus pneumoniae* bacterium, making it easier to detect than nucleases that are secreted because it cannot diffuse away from the cell. The investigators found that this nuclease, which is known as EndA is capable of digesting a probe that has 2'-fluoro modified pyrimidines, but not a probe with 2'-O-methyl modified pyrimidines.

Degradation Activity of Micrococcal Nuclease and EndA Nuclease.

Figure 17:
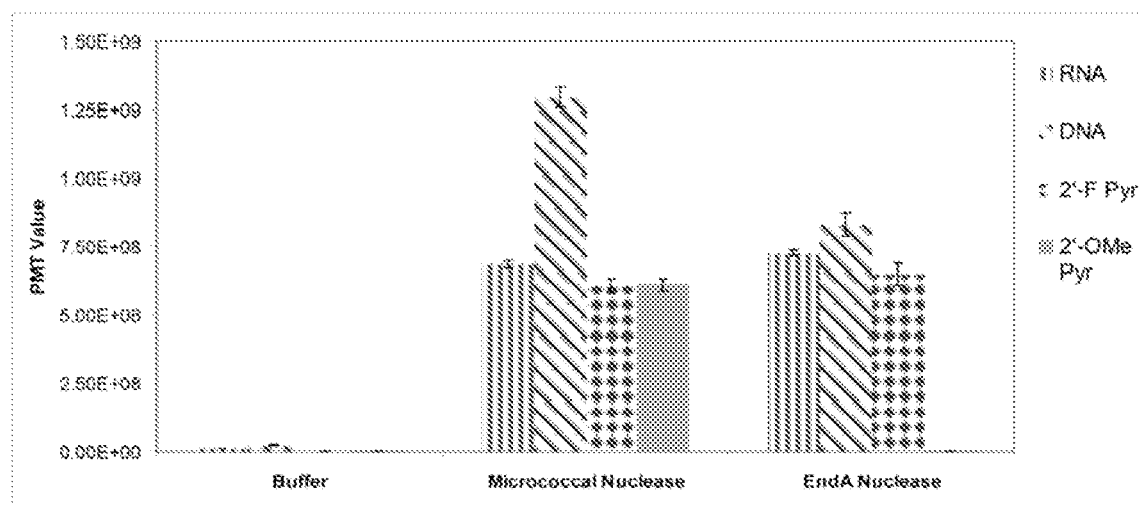
FIG. 17. Degradation activity of Micrococcal Nuclease and EndA Nuclease. Unmodified (RNA and DNA) and modified (2'-Fluoro pyrimidines and 2'-O-Methyl pyrimidines) nucleic acid substrates were used to assay the nuclease activity profile of Micrococcal Nuclease (MN) and EndA (H160G) Nuclease. The probes consist of a 12 nucleotide long oligonucleotide, 5'-UCUCGUACGUUC-3' (SEQ ID NO:6), with the chemical modifications indicated in the figure, flanked by a FAM (5'-modification) and a pair of fluorescence quenchers, "ZEN" and "Iowa Black" (3'-modifications). This approach allows the evaluation of nuclease activity which is indicated by increases in fluorescence upon substrate digestion. 50 pmoles of substrate were incubated with MN (1 U/µL) and EndA H160G Nuclease (2 µM) in 10 µl total volume. Imadazole was included in the EndA H160G reactions to recapitulate the enzymatic properties of the wildtype enzyme. This mutant version of the enzyme was used because the wt enzyme was toxic to *E. coli* and could not be produced recombinantly in large amounts. 50 pmoles of each substrate and buffer were used as controls. All reactions were incubated for 30 minutes at 37° C. After incubation, 290 µl of buffer supplemented with 10 mM EDTA and 10 mM EGTA were added to each sample and 95 µl of each sample were loaded in triplicate into a 96-well plate (96F non-treated black microwell plate (NUNC)). Fluorescence intensity was measured with a fluorescence microplate reader (Analyst HT; Biosystems).

Unmodified (RNA and DNA) and modified (2'-Fluoro pyrimidines and 2'-O-Methyl pyrimidines) nucleic acid substrates were used to assay the nuclease activity profile of Micrococcal Nuclease (MN) and EndA (H160G) Nuclease. The substrates were flanked by a fluorescent dye (FAM) at the 5'-end and a quencher at the 3'-end. This approach allows the evaluation of nuclease activity which is indicated by increases in fluorescence upon substrate digestion. 50 pmoles of substrate were incubated with MN (1 U/µL) and EndA H160G Nuclease (2 µM) in 10 µl total volume. Imadazole was included in the EndA H160G reactions to recapitulate the enzymatic properties of the wildtype enzyme. This mutant version of the enzyme was used because the wt enzyme was toxic to *E. coli* and could not be produced recombinantly in large amounts. 50 pmoles of each substrate and buffer were used as controls. All reactions were incubated for 30 minutes at 37° C. After incubation, 290 µl of buffer supplemented with 10 mM EDTA and 10 mM EGTA were added to each sample and 95 µl of each sample were loaded in triplicate into a 96-well plate (96F non-treated black microwell plate (NUNC)). Fluorescence intensity was measured with a fluorescence microplate reader (Analyst HT; Biosystems) (FIG. 17).

Example 8

Nuclease-Activated Probes for Imaging
*Staphylococcus aureus* Infections

*S. aureus* infections are a major clinical problem that results in a variety of life-threatening and debilitating medical conditions including septic joints, osteomyelitis and endocarditis. Development of antibiotic resistant strains of *S. aureus* has compounded the difficulty of treating infections and highlights the need for novel antibiotics and better diagnostic approaches for their evaluation. Most *S. aureus* infections with clinical significance are localized to internal tissues or organs that are difficult to access. Definitive diagnosis of *S. aureus* infection thus necessitates testing biopsies of suspected tissues for presence of the bacteria. Because only limited tissues can be surveyed, biopsies offer only a limited assessment of the possibility an individual is suffering from an *S. aureus* infection. In some cases, such as endocarditis, biopsies are impractical and diagnoses are made with circumstantial evidence such as heart murmur and the detection of bacteria in the circulation.

To address the present shortcomings in the diagnostic technology for localized *S. aureus* (and other bacterial) infections, molecular imaging approaches have been developed to non-invasively detect bacteria in animals. These approaches depend on the selective affinity of the imaging reagents for components of bacteria. For example, one approach uses molecular probes that function by binding components of bacteria with greater affinity than mammalian cells and tissues. In general, because such probes are always "on" they have suboptimal target-to-background ratios, which limit their sensitivity. These probes are limited by the fact that they produce signal prior to encountering their target (i.e., they are not activatable probes) and most of them are non-specific with respect to bacterial species.

An alternative molecular imaging approach, involving quenched fluorescent probes that are activated by tumor-specific proteases, has provided a valuable imaging platform for cancer imaging. Because such activatable probes do not produce signal (fluorescence) until the probe encounters its target, the result is a very high target-to-background ratio and a much more sensitive means of target detection. While this approach has proven valuable for imaging cancer, to-date it has not been applied to imaging bacteria, possibly due to a scarcity of appropriate bacteria-derived proteases. The inventors exploited the interface between chemically modified nucleic acids and bacterial nucleases to develop activatable imaging probes for bacterial infections. This research is innovative because the exploitation of nucleases for imaging is a novel direction, both for the imaging of bacterial infections in particular and for whole-animal imaging in general.

The present invention provides a robust activated imaging probe-based approach for the non-invasive detection and localization of *S. aureus* infections in animals. This contribution is significant because activated imaging probes have critical advantages (e.g., high target-to-background ratios) over existing technology for this problem, and may prove to be generally useful for both research and clinical diagnostic applications involving *S. aureus*. The present approach facilitates the evaluation in experimental animals of novel antibiotics for naturally occurring strains of these bacteria.

This near-infrared fluorescence-based imaging approach also is useful for the diagnosis and treatment evaluation of *S. aureus* infections in humans. Indeed, near-infrared fluorescent dyes are currently used as clinical imaging tools for retinal angiography, cardiac function, hepatic output, sentinel lymph node dissection and colon polyp identification. The clinical applicability of near-infrared imaging, which has limited imaging depth in tissues (estimated at 7-14 cm), is expanding due to the development of medical imaging devices such as endoscopes with fluorescence imaging capabilities. Interestingly, many additional problematic pathogens are also known to express secreted or cell-surface nucleases (e.g., *Streptococcus pneumoniae*), which are used for their detection.

A. Generation of Nuclease-Activated Probes that Specifically Detect Micrococcal Nuclease (MN) of *S. aureus*

The need for clinical diagnostic imaging of bacterial infections is greatest for localized infections, which are often difficult to diagnose. In contrast, systemic infections can usually be detected with simple blood tests. *S. aureus* is the most common bacterial cause of a variety of focal infections in humans, including infectious joints, osteomyelitis and endocarditis. For example, *S. aureus* is the causative bacterial pathogen in approximately half of the cases of infectious joints which are a serious medical condition, associated with substantial morbidity and mortality. Additional types of bacteria that are commonly found to cause septic joints include non-*aureus* Staphylococci and Streptococci (group A-G and *pneumoniae*). A variety of additional bacterial species, including Gram negative bacteria such as *E. coli* can also, in rare cases, cause septic joints.

Micrococcal nuclease is a robust extracellular nuclease produced by *S. aureus*. It readily digests DNA and RNA via endonuclease and exonuclease activities, and its activity has been used to detect the presence of *S. aureus* in various contexts for decades. MN has been found to play a role in *S. aureus* immune evasion and is a virulence factor of *S. aureus*. Interestingly, a portion of MN is apparently expressed on the surface of *S. aureus* cells.

Most *Streptococcus* species that cause infectious joints also produce extracellular nucleases. Group A Streptococci are known to produce at least four such nucleases, SdaA, SdaB, SdaC and SdaD. Of these, SdaA and SdaC are known to be DNAses, while SdaB and SdaD are able to digest DNA and RNA (Wannamaker et al., 1967). SdaB and SdaD are thus expected to digest a more diverse set of chemically modified nucleic acids. Extracellular nucleases of Group B Streptococci have also been studied and at least three of these enzymes degrade DNA and RNA (Ferrieri et al., 1980). DNAse activity has also been observed in culture supernatants from Group C and G Streptococci, but the enzymes responsible for this activity are not well-characterized. A cell-surface nuclease of *Streptococcus pneumoniae*, known as EndA, has also been well-studied (Moon, A. F., Midon, M., Meiss, G., Pingoud, A., London, R. E., and Pedersen, L. C. (2011). Structural insights into catalytic and substrate binding mechanisms of the strategic EndA nuclease from *Streptococcus pneumoniae*. Nucleic Acids Res 39, 2943-2953).

An ideal molecular imaging probe for *S. aureus* would produces a signal only upon encountering the targeted, unmodified bacteria or material derived from it. Such probes enable the in vivo dynamic imaging of naturally occurring *S. aureus* strains with superior target-to-background ratios over existing technologies and facilitate the clinical diagnosis and treatment evaluation of *S. aureus* infections in humans. The lack of versatile, specific and robust bacterial imaging methods is a critical barrier for the study of *S. aureus* in animals and the evaluation of *S. aureus* infections in humans.

Oligonucleotide-based nuclease substrates with fluorophore-quencher pairs (fluorophore is unquenched upon nuclease digestion) are tailored via chemical modification to specifically detect nucleases of *S. aureus* and thus serve as specific and sensitive probes for the detection of the bacteria themselves. The data provided below demonstrate the sensitive detection of an *S. aureus*-derived nuclease in vitro and in mice with chemically modified oligonucleotide-based nuclease substrates. Importantly, these substrates are resistant to mammalian nucleases; they thus exhibit a very low background in animals in the absence of foreign nucleases.

The data provide examples of chemically modified oligonucleotide probes that can differentiate between MN and mammalian serum nucleases. Thus, oligonucleotides with the appropriate chemical modifications are readily digested by MN, but resistant to both mammalian and various bacterial nucleases. Several distinct bacterial and mammalian nucleases have been tested in these in vitro experiments. These nuclease-activated probes with quencher/fluorophore pairs (fluorophores will be near-infrared) that are susceptible to digestion by MN may enable the non-invasive detection and localization of focal *S. aureus* infections in mice.

For therapeutic applications involving synthetic RNA, chemical modifications have been developed to increase the resistance of RNA to degradation by mammalian nucleases. Modification of pyrimidines by substitution of the 2'-OH of the ribose sugar for different groups such as fluoro (2'-F) or O-methyl (2'-OMe) have been found to substantially increase resistance of RNA to nuclease degradation (Green, L. S., et al. (1995). Nuclease-resistant nucleic acid ligands to vascular permeability factor/vascular endothelial growth factor. Chem Biol 2, 683-695; Pieken, W. A., et al. (1991). Kinetic characterization of ribonuclease-resistant 2'-modified hammerhead ribozymes. Science 253, 314-317). For example, RNA with 2'-F modified pyrimidines is stable is animal serum for many hours. These modifications have become commonplace in the development of RNA-based therapeutics (Behlke, M. A. (2008). Chemical modification of siRNAs for in vivo use. Oligonucleotides 18, 305-319; Thiel, K. W., and Giangrande, P. H. (2009). Therapeutic applications of DNA and RNA aptamers. Oligonucleotides 19, 209-222). Considering the stability of these modified RNAs in mammalian fluids, it was reasoned that they might be useful reagents for bacteria detection if bacteria-derived nucleases can digest them. Thus, the ability of various bacterial nucleases (derived from *S. aureus*, *Streptococcus pneumoniae* and *Mycoplasma*) to digest such modified RNA was measured.

Figure 18:
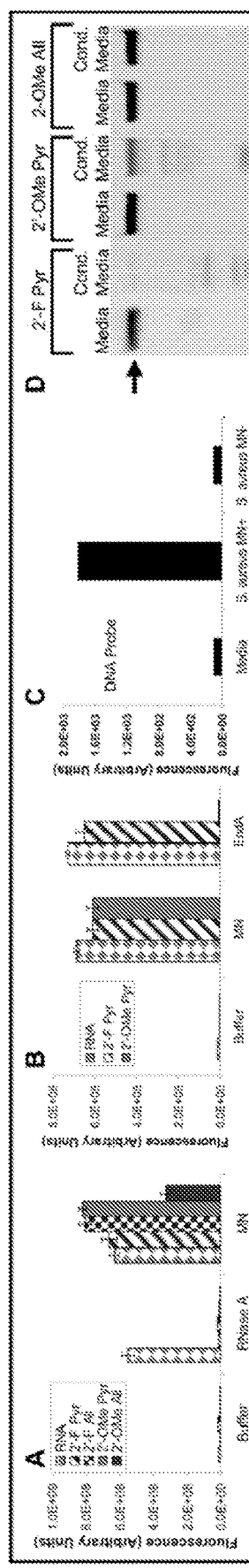
FIGS. 18A-18D. Digestion of various nucleic acids by bacterial nucleases. Incubation of a 12 nucleotide-long RNA oligo (UCUCGUACGUUC (SEQ ID NO:6) with a 5'-Fam and a 3'-Quencher) with the indicated modifications with buffer only, RNAse A (Panel A), MN (1 unit/µl) (Panels A and B) and EndA (20 µM) (Panel B) for 1 hour at 37° C. Panel C shows digestion of a quenched fluorescent DNA oligo with S. aureus culture supernatants (+ or −MN) incubated for 10 minutes at 37° C. Digestion results in florescence increases in each of the experiments in Panels A-C. Panel D shows the PAGE analysis of a 51 nucleotide-long FAM-labeled (3'-end) RNA oligo with the indicated modifications after 1 hour, 37° C. incubation with complete, serum-containing cell culture media or with the same media conditioned by HEK cells contaminated with Mycoplasma fermentans. Arrow indicates full-length RNA. Modified RNAs were not digested in media conditioned with uncontaminated HEK cells.

To measure nuclease activity in vitro quenched fluorescent oligos were used (platereader-based assays shown in FIGS. 18A, B and C) and polyacrylamide gel electrophoresis (PAGE, FIG. 1D). MN digests unmodified RNA, RNA with pyrimidines modified with 2'-F, or 2'-OMe, or fully 2'-F or fully 2'-OMe modified RNA, whereas mammalian RNAse A only digests unmodified RNA (FIG. 18A). EndA (cell-surface nuclease of *Streptococcus pneumoniae*) digests RNA with pyrimidines modified with 2'-F, but not with 2'-OMe (FIG. 18B). EndA and MN thus have different substrate specificities with respect to the modified RNAs, suggesting that chemically modified RNA probes may be used to differentiate between them. For detection of *S. aureus* via MN activity, culture supernatants provide a more clinically relevant preparation. Thus nuclease activity of *S. aureus* culture supernatants (wt and MN-negative (*S. aureus* MN−)) was measured. The clear activity in the MN+ supernatant (DNA probe, FIG. 18C) indicates that such probes can detect the presence of the bacteria via MN activity. A PAGE-based assay, as shown in FIG. 18D for the activity of a *Mycoplasma*-derived nuclease, is a complement to the platereader assay as it provides an assessment of the degradation products. Note the activity of the *Mycoplasma fermentans*-derived nuclease on the 2'-F and 2'-OMe (pyrimidines) modified RNA oligos.

Short oligonucleotides, flanked with a fluorophore (5'-end) and a quencher (3'-end) are useful reagents for evaluating the nuclease susceptibility of oligos with many distinct nucleotide modifications. To test the ability of nucleases derived from pathogenic bacteria to degrade oligonucleotides of different chemical compositions, the nucleases are co-incubated with such oligonucleotide probes, followed by measurement of fluorescence levels in a fluorescence plate reader. Increases in fluorescence beyond levels seen in control oligo incubations in which nucleases are omitted, are indications of oligo degradation. In addition to the simplicity and convenience of this approach, another advantage is that any probes found to specifically detect MN in these assays can be used to instruct the design of in vivo probes for *S. aureus* because the latter probes are also based on oligos with quenched fluorophores. Oligonucleotide compositions found to be specifically susceptible to degradation by MN are further studied by examining the susceptibility of unlabeled (i.e., no fluorophore or quencher) versions of the oligonucleotides with polyacrylamide gel analysis of degradation in place of the plate-reader assay.

The oligonucleotide probes consists of 12 nt-long RNA oligos (5'-UCUCGUACGUUC-3' (SEQ ID NO:6)) flanked by a FAM (5'-end) and fluorescence quenchers, "ZEN" and "Iowa Black" (3'-end). For the degradation assays, 50 pmoles of each oligonucleotide are combined with each sample (e.g., culture supernatant) and incubated at 37° C. for 30 minutes to 4 hours. The purified nucleases are diluted in PBS supplemented with physiological concentrations of calcium and magnesium. Various dilutions of each nuclease are tested to determine the limiting concentration of each. After incubations, the reactions are loaded in triplicate into a 96-well plate. Fluorescence is measured with a microplate reader (Analyst HT; Biosystems). Controls for each experiment include an unmodified RNA probe incubated with buffer (-control) or RNAse A (+control). Each probe is incubated with buffer or culture broth only (to establish background fluorescence levels) in parallel with the nuclease incubations.

Chemical modifications that are tested include various modifications that are known to promote resistance to mammalian nucleases, including: 2'-fluoro-β-D-arabinonucleotide (FANA), Locked Nucleic Acid (LNA), Unlocked Nucleic Acid (UNA), 2'-O-methyl, 2'-fluoro and phosphorothioate (a sugar-phosphate backbone modification) (Behlke, M. A. (2008). Chemical modification of siRNAs for in vivo use. Oligonucleotides 18, 305-319).

Probes are also studied with the following gel-based degradation assay in order to determine the full extent of degradation. These experiments are necessary to distinguish between enzymatic activity that might simply remove a terminal nucleotide or possibly the quencher or fluorophore from a probe as opposed to more thorough nuclease digestion. The former type of degradation may only occur with particular fluorophores or quenchers and thus may not be generally useful for nuclease detection. For each reaction, 50 pmoles of an unlabeled version of the selected oligo is combined with buffer or with the nucleases, culture material or serum samples indicated above and incubated for 0.5 to 4 hours at 37° C. After incubation, samples are resolved on a 7.7M Urea/10% acrylamide gel. Gel images (stained with SYBR Gold) are acquired with uv-light transillumination and a digital camera.

B. Demonstration of the Detection of the *S. aureus* Nuclease (MN) in Mice with Nuclease-Activated Probes.

Activatable imaging probes for non-invasive imaging of various biological phenomena, provide high target-to-background ratios, and are thus actively sought for applications such as cancer imaging. However, activatable imaging probes for focal bacterial infections have not been described. The present experiments demonstrate the feasibility of a novel nucleic acid-based activatable imaging approach for the detection and localization of *S. aureus* associated nuclease activity in mice.

The non-invasive detection of tumors in mice with quenched fluorescent protease substrates was first reported in 1999 (Weissleder, R., et al. (1999). In vivo imaging of tumors with protease-activated near-infrared fluorescent probes. Nat Biotechnol 17, 375-378). These probes detect proteases that are overexpressed by cancer cells. Importantly, the fluorophores used in the probes absorb and emit near-infrared light, which can penetrate tissues much better than light in the visible regions of the spectrum. The initial report of this approach provided the conceptual basis for many subsequent studies describing similar protease substrate-based tumor imaging approaches. Importantly, this approach is not limited to detection of subcutaneously implanted tumors. Bone metastases are among the types of cancers detectable with near-infrared imaging. The activatable imaging probe concept has also been pursued for non-invasive imaging in a variety of forms not involving protease activation due to the high target-to-background ratios achieved with activatable probes.

Activatable molecular imaging approaches have not been developed for imaging bacterial infections. Instead, bacterial infections have been imaged with probes that exhibit greater affinity for the bacteria than for mammalian cells and tissues. As the utility of NIR-based imaging for cancer became clearer, important progress has been made in developing more sophisticated NIR-based imaging instrumentation, including fluorescence tomography for acquisition of 3-dimensional fluorescence images and multispectral imaging approaches for removal of autofluorescence and fluorescence multiplexing. NIR-based imaging technologies have also been introduced into clinical practice. While the depth of light penetration with NIR light is a limitation of NIR-based imaging (estimated to be 7-14 cm), the broad potential of the technology in the clinic is highlighted by a recent study demonstrating the deep-tissue imaging of lymphatic vessels within the leg of a human subject.

Oligonucleotide-based probes with quenched fluorophores have been in common use as tools for various molecular biology methods for over a decade. This robust technology includes Molecular Beacons and TaqMan probes whose fluorescence is unquenched after the probes anneal to a targeted complementary nucleic acid and "RNAse Substrates", which are used to detect the presence of contaminating RNAses in laboratory solutions.

For in vivo applicability of nuclease-activated imaging probes, visible-wavelength fluorophores (e.g., those used in FIGS. 18A-D) are not optimal due to high autofluorescence and light scattering of visible light by tissues. The inventors, therefore, tested nuclease-activated probes with an NIR fluorophore (Cy5.5). A 2'-fluoro pyrimidine modified RNA oligo with 5'-Cy5.5 and 3'-quencher were combined with PBS alone or PBS plus micrococcal nuclease and incubated for 60 minutes at 37° C. prior to imaging. Fluorescence was measured with a Xenogen IVIS small animal imaging system. A quenched Cy5.5 probe composed of RNA with 2'-F modified pyrimidines exhibited a very low level of NIR fluorescence prior to digestion, and a robust (130-fold) increase in fluorescence after MN digestion. To explore the utility of this probe for imaging bacterial nucleases in mice, MN was injected into the leg muscle of a mouse which was subsequently administered 5 nmoles of the probe via tail vein injection. Fluorescence was found to develop initially at the site of MN injection. This signal increased over the next 45 minutes. In addition, a strong fluorescence signal developed in the abdomen, presumably emanating from the liver. Whether this liver-based signal resulted from liver-based digestion of the probe or accumulation of probe fragments of the MN digestion is uncertain. Finally, to evaluate the utility of luciferase-expressing *S. aureus* for multimodal mouse imaging experiments with Cy5.5-labeled probes, a Lux operon was transferred to the Newman strain of *S. aureus* and imaged with bioluminescence and Cy5.5 fluorescence channels of an IVIS system. While the bioluminescence of the Luc+ *S. aureus* was strong, the luciferase-derived light was not seen in the Cy5.5 fluorescence channel, thus indicating the feasibility of Luciferase/Cy5.5 co-localization experiments (i.e., the Luciferase signal does not interfere with Cy5.5 measurements).

To evaluate the ability of quenched fluorescent nuclease substrates to indicate the presence and localization of focal *S. aureus* infections in mice, we will use a probe that yielded promising results in preliminary whole animal optical imaging experiments. This probe, which consists of a short RNA oligonucleotide with 2'-F modified pyrimidines and unmodified purines, is resistant to activation by mammalian nucleases, but susceptible to degradation (and activation) by various bacterial nucleases, including nucleases produced by *S. aureus* (MN), *Streptococcus pneumoniae* and *Mycoplasma fermentans*. The probe is flanked by a near-infrared fluorophore and a fluorescence quencher. To independently measure *S. aureus* localization, luciferase-expressing strains of *S. aureus* will be used in combination with bioluminescence imaging. Co-localization of fluorescence (activated nuclease probe) with luminescence (luciferase) will indicate that the nuclease-detecting approach can serve to detect and localize focal *S. aureus* infections in mice. Focal infections in mice will be induced by intramuscular (leg muscle) injection of *S. aureus*. Imaging and intravenous probe administration will take place 24-48 hours after the bacterial injection.

The oligonucleotide probe is synthesized by Integrated DNA Technologies (IDT; Coralville, Iowa). The probe consists of an 11 nucleotide-long RNA oligo (5'-CUCGUACGUUC-3' (SEQ ID O: 36)) flanked by Cy5.5 (5'-end) and a pair of fluorescence quenchers, "ZEN" and "Iowa Black" (3'-end). Mice are injected (intramuscular, leg muscle) with 100 ul (~4×10$^6$ CFU/injection) methicillin-sensitive *S. aureus* (MSSA) modified with the Lux operon (for Luciferase expression). 24-48 hours after administration of the *S. aureus*, mice are anesthetized with isofluorane and imaged (Xenogen IVIS-200 System) with bioluminescence to assess the degree of infection and with fluorescence (Cy5.5 infrared channel) to establish baseline fluorescence measurements. Then 5-10 nanomoles of the nuclease probe are injected via tail vein and bioluminescence and fluorescence images are acquired every 5-10 minutes for 1-2 hours.

Fluorescence levels above those measured prior to probe administration indicate the presence of activated probe. The contribution of substantial fluorescence from the unactivated probe is not expected as negligible fluorescence of the undigested probe was observed in preliminary studies. The probe is also administered to uninfected mice to determine the dependence of probe activation on the presence of *S. aureus*. To determine the dynamic biodistribution of the probe, control experiments are carried out in which a probe missing the quenchers are administered to infected animals and imaged at various time-points. The complete probe is administered to animals infected with MN-negative *S. aureus* to determine the dependence of *S. aureus* detection on the presence of this nuclease.

Example 9

Nuclease-Activated Probes for Imaging *Staphylococcus aureus* Infections

The inventors surprisingly discovered that "2'-OMe dTT" probe was more sensitive to MN (micrococcal nuclease of *S. aureus*) than the other probes, but was still resistant to degradation in serum. The inventors tested its stability in the supernatants of cultures of other pathogenic bacteria that cause similar problems as *S. aureus* and found that it was not digested by these other species. The 2'-OMe dTT probe thus is specific for *S. aureus*.

Digestion of Oligonucleotide Substrates with Various Concentrations of Micrococcal Nuclease (MN).

Figure 19:
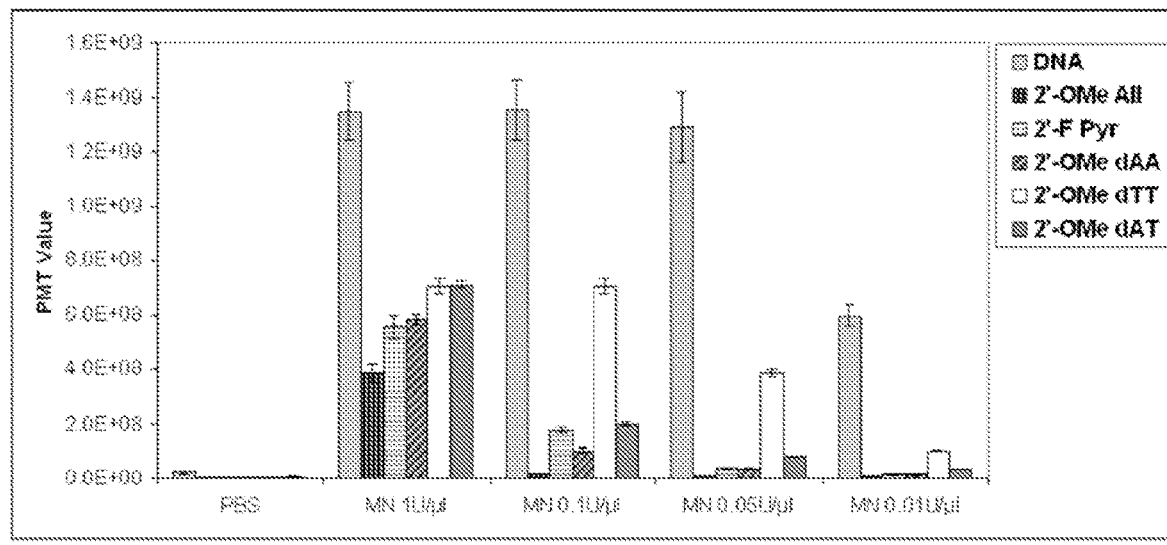
FIG. 19. Digestion of oligonucleotide substrates with various concentrations of micrococcal nuclease (MN).

The degradation profile of 6 oligonucleotide substrates was evaluated using 4 different concentrations of MN (1 U, 0.1 U, 0.05 U and 0.01 U/µl) (FIG. 19). All the sequences are flanked by a FAM at 5'- and a pair of fluorescence quenchers, "ZEN" and "Iowa Black" at the 3'-end. The samples were prepared as follow: PBS, 9 µl of PBS+1 µl of substrate (50 pmoles); Reactions with MN include 8 µl of PBS, 1 µl of substrate (containing 50 pmoles) and 1 µl of appropriately diluted MN. All the samples were incubated at 37° C. for 15 minutes. After the incubation period, 290 µl of PBS supplemented with 10 mM EDTA and 10 mM EGTA was added to each sample and 95 µl of each was then loaded in triplicate into a 96-well plate (96F non-treated black microwell plate (NUNC)). Fluorescence intensity was measured with a fluorescence microplate reader (Analyst HT; Biosystems).

The oligonucleotide molecules are provided in Table 5 below.

Figure 20:
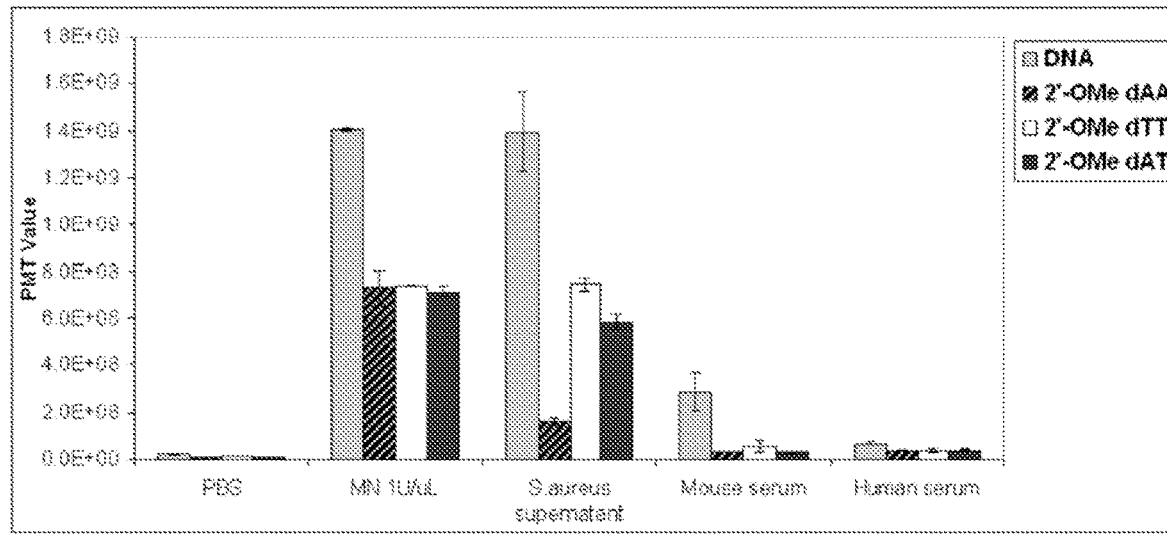
FIG. 20. Oligonucleotide substrate plate-reader assays.

Oligonucleotide Substrate Plate-Reader Assays:

The oligonucleotide substrates were synthesized by Integrated DNA Technologies (IDT; Coralville, Iowa). These probes consist of a 10 (DNA) or 11 nucleotide long (2'-OMe-dAA, 2'-OMe-dTT and 2'-OMe-dAT) oligonucleotide, with the chemical modifications and sequences indicated in Table 1 above. All the sequences are flanked by a FAM at 5'-end and a pair of fluorescence quenchers, "ZEN" and "Iowa Black" at the 3'-end. Five samples were assayed for degradation (FIG. 20). PBS: 1 µl of each substrate (50 picomoles) was combined with 9 µl of PBS (background). Reactions with micrococcal nuclease (MN) served as positive control as the investigators have established that the condition used here yields maximal activation of the probes. These reactions include 1 µl of each substrate (50 picomoles), 8 µl of PBS and 1 µl of MN (10 U/µl). Reactions with *S. aureus* supernatant include 1 µl of each substrate (50 picomoles) and 9 µl of supernatant of a 24-hour culture of *S. aureus*. Reactions with mouse and human serum include 1 µl of each substrate (50 picomoles) combined with 9 µl of mouse or human serum, respectively. All the samples were incubated at 37° C. for 1 hour. After the incubation period, 290 µl of PBS supplemented with 10 mM EDTA and 10 mM EGTA was added to each sample and 95 µl of each was then loaded in triplicate into a 96-well plate (96F non-treated black microwell plate (NUNC)). Fluorescence intensity was measured with a fluorescence microplate reader (Analyst HT; Biosystems).

Figure 21:
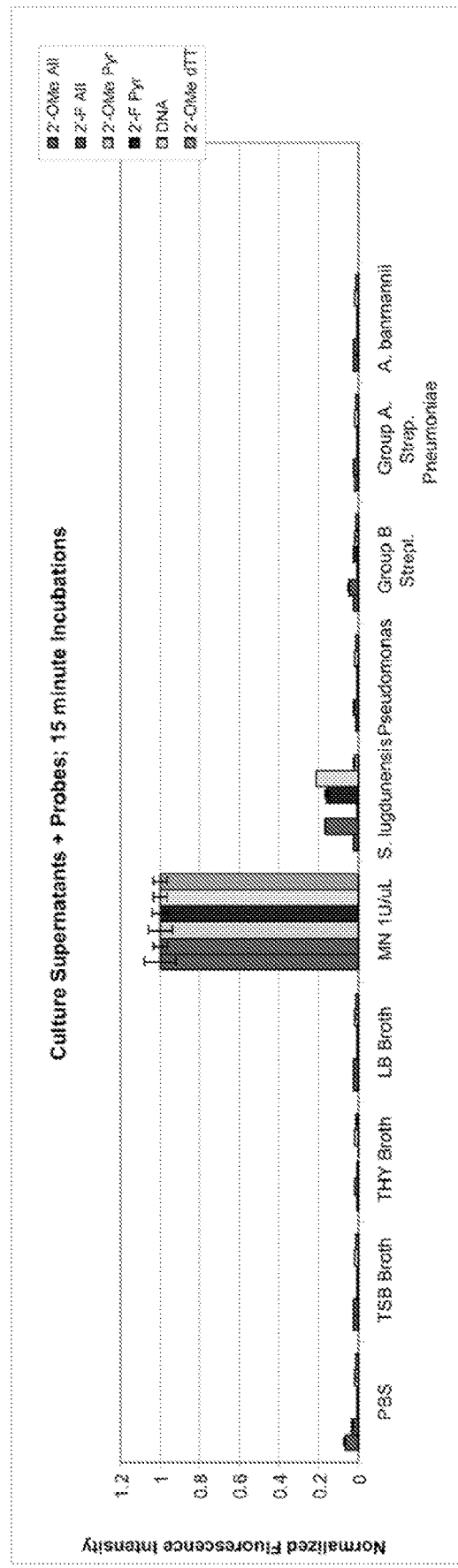
FIG. 21. Cultures of the indicated bacteria were grown to stationary phase. Bacteria were pelleted via centrifugation and nuclease activity of supernatants was measured as described for FIG. 13. To determine background levels of probe fluorescence/activation in each of the bacteria-free culture broth preparations used, probes were combined with each of the indicated broths in addition to PBS and incubated in parallel with the culture supernatant reactions. Incubation time was 15 minutes.

Additional data shows that the "2'-OMe dTT" probe was more sensitive to MN (micrococcal nuclease of *S. aureus*) than other probes, but it was still resistant to degradation in serum (FIGS. 19 & 20). Its stability was then tested in the supernatants of cultures of other pathogenic bacteria that cause similar problems as *S. aureus* and it was found that it was not digested by these other species (FIG. 21). The 2'-OMe dTT probe thus is specific for *S. aureus*.

TABLE 5

| Name | Length | Sequence | SEQ ID NO |
|---|---|---|---|
| DNA | 10 | /56-FAM/TTCCTTCCTC/ZEN//3IAbRQSp/ | SEQ ID NO: 37 |
| 2'-OMe All | 12 | /56-FAM/mUmCmUmCmGmUmAmCmGmUmUmC/ZEN//3IAbRQSp/ | SEQ ID NO: 38 |
| 2'-F Pyr | 12 | /56-FAM/fUfCfUfCrGfUrAfCrGfUfUfC/ZEN//3IAbRQSp/ | SEQ ID NO: 39 |
| 2'-OMe dAA | 11 | /56-FAM/mCmUmCmGAAmCmGmUmUmC/ZEN//3IAbRQSp/ | SEQ ID NO: 40 |
| 2'-OMe dTT | 11 | /56-FAM/mCmUmCmGTTmCmGmUmUmC/ZEN//3IAbRQSp/ | SEQ ID NO: 41 |
| 2'-OMe dAT | 11 | /56-FAM/mCmUmCmGATmCmGmUmUmC/ZEN//3IAbRQSp/ | SEQ ID NO: 42 |

/56-FAM/ FAM fluorophore (fluorescein amidite)
/ZEN/ "ZEN" fluorescence quencher
/3IAbRQSp/ "Iowa Black" fluorescence quencher
mA 2'-O-methyl modified A
mC 2'-O-methyl modified C
mG 2'-O-methyl modified G
mU 2'-O-methyl modified U
fA 2'-fluoro modified A
fC 2'-fluoro modified C
fG 2'-fluoro modified G
fU 2'-fluoro modified U
Nucleotides written in bold are deoxy nucleotides (DNA)

Example 10

Non-Invasive Imaging of *Staphylococcus aureus* Infections with a Nuclease-Activated Probe Diagnosis of focal bacterial infections, such as osteomyelitis, septic joints and pyomyositis initially entails the evaluation of several non-specific symptoms, including pain, swelling and fever. Definitive evidence of infection and identification of the causative bacterial species is only possible with tissue biopsy and culture. While many focal bacterial infections are life-threatening situations in which time is of-the-essence, such diagnostic procedures typically consume many hours to days. Moreover, current diagnostic approaches, including x-ray imaging and biopsy/culture, are prone to false-negatives due to their low sensitivity and susceptibility to missing the infected tissue, respectively.

It has been previously reported that some bacterial nucleases can efficiently digest chemically modified oligonucleotides that are resistant to degradation by mammalian nucleases. Here, it was sought to use this observation to develop a non-invasive molecular imaging approach for *S. aureus*, the most common culprit of many types of focal infections in people. *S aureus* secretes a nuclease known as micrococcal nuclease (MN). A very well-studied enzyme, MN is among the first proteins extensively investigated with structure and folding studies. MN exhibits robust DNase and RNase activities, is active on both single- and double-stranded substrates, and its nuclease activity has been used to classify laboratory bacterial preparations for decades.

A short oligonucleotide substrate that is both sensitive to MN and resistant to serum nucleases was sought. Such an oligonucleotide could form the basis of a quenched fluorescent imaging probe that is specifically activated (fluorescence is unquenched) upon digestion by MN. Because the susceptibility of chemically modified oligonucleotide substrates to MN digestion is poorly understood, the ability of MN to degrade oligonucleotide substrates was tested with a variety of chemical modifications that are known to promote resistance to degradation by mammalian serum nucleases. To facilitate the subsequent development of imaging probes, the various oligo compositions were tested in a quenched fluorescent probe format: short (10-12 mers) oligos flanked with a 5'-fluorophore (FAM) and 3'-quenchers (Zen and Iowa Black RQ).

Figure 22A:
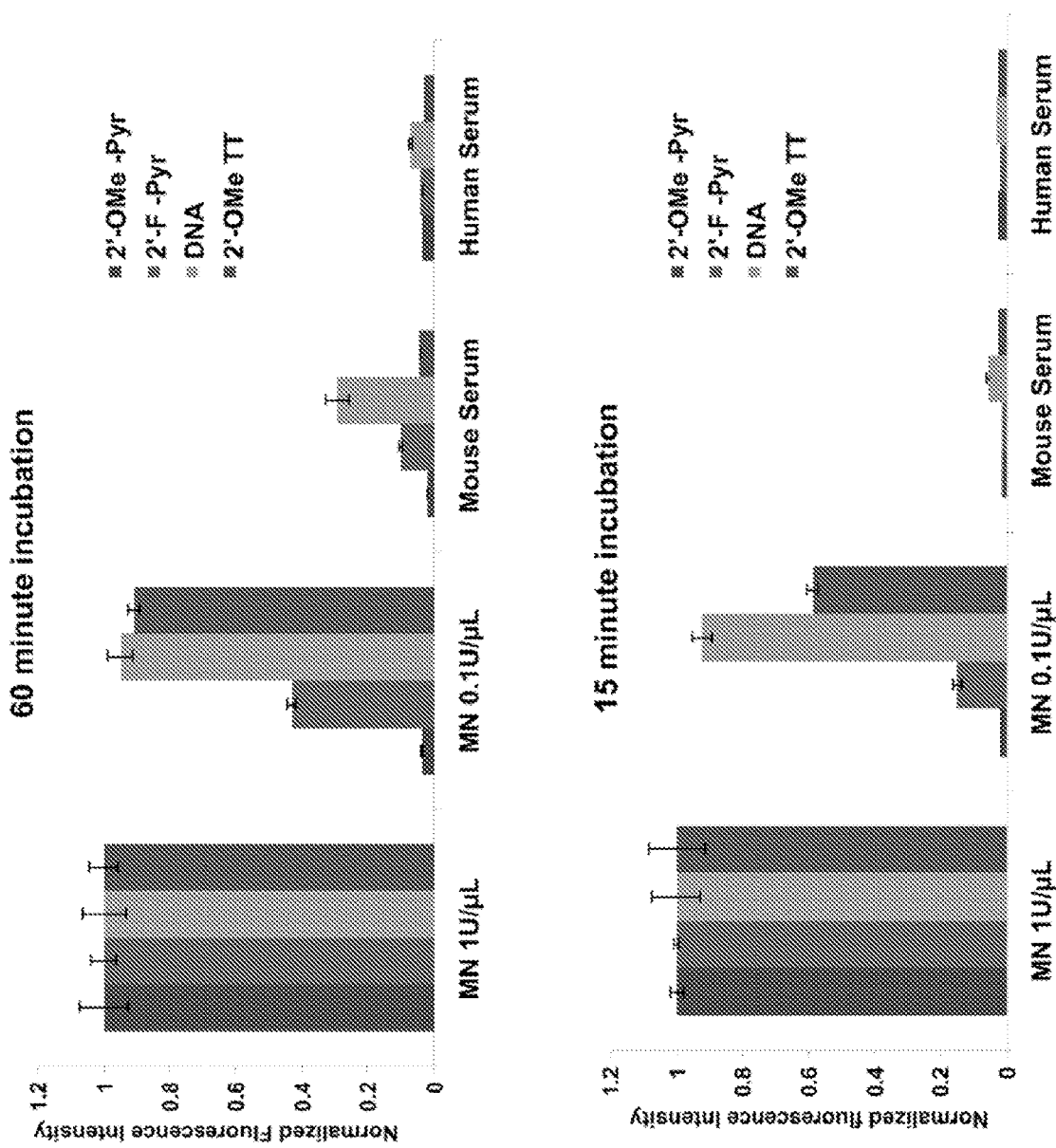
FIGS. 22A-22B. Activation of various nucleic acid probes (see Table 4 for probe details) by MN, mouse and human serum (A), and S. aureus MN-expressing and MN-negative (Newman and UAMS-1 strains) culture supernatants (B). 50 picomoles of each of the indicated probes was incubated with 1 U/µl (positive control) or 0.1 U/µl MN in DPBS (includes physiological levels of calcium and magnesium), or with 90% mouse or human serum (A) or with 90% of culture supernatants of the indicated S. aureus strains (prepared as described in Materials and Methods) for 60 minutes at 37° C. After the incubations, each reaction was divided into 3 volumes which were read in a fluorescence plate-reader. Mean fluorescence values of all reactions with a given probe were normalized to the mean fluorescence measured with digestion of the probe with 1 U/µl MN. Error bars represent standard deviations of the plate-reader values. Background fluorescence subtractions were carried out (prior to normalization) as follows: The fluorescence of each of the probes incubated in DPBS was subtracted from the corresponding MN-containing reactions. The fluorescence of each of the probes incubated in DPBS plus the autofluorescence of each serum (mouse or human) was subtracted from the serum-containing reactions. The fluorescence of each of the probes incubated in unconditioned TSB was subtracted from the corresponding S. aureus culture supernatant reactions.

One such probe, made with an oligo composed exclusively of locked nucleic acid-modified nucleotides, was not digested by MN (FJH, unpublished observations), while oligos composed exclusively of 2'-fluoro- or 2'-O-methyl-modified nucleotides were relatively weak substrates. Next, the MN– and serum nuclease-susceptibility of RNA oligos composed of 2'-fluoro- or 2'-O-methyl-modified pyrimidines and unmodified purines with a DNA oligo were compared, as DNA is the preferred substrate for MN among unmodified nucleic acids (see Table 6 for probe sequences and modifications). Concentrated MN (1 U/µl) yielded complete or near-complete digestion of these oligos after short incubations and was thus used as a normalization control for the assays. More dilute MN (0.1 U/µl) provided an intermediate degree of digestion after 15 or 60 minutes, thus enabling assessment of the relative degree of digestion of the substrates. As shown in FIG. 22A, the DNA probe was digested by MN more efficiently than either the 2'-fluoro- or 2'-O-methyl-modified pyrimidine RNA oligos, but was, as expected, also substantially digested in serum. In contrast, the 2'-fluoro- and 2'-O-methyl-modified pyrimidine RNA oligos were more stable in serum, but less efficiently digested by MN. A second generation probe, composed of a pair of deoxythymidines flanked by several 2'-O-methyl modified nucleotides, was designed to maximize sensitivity to MN, which is known to efficiently digest poly-deoxythymidine oligos, while also resisting degradation by serum nucleases. This "TT probe" was substantially more sensitive to MN digestion than the other chemically modified oligos tested, and also exhibited robust serum stability (FIG. 22A).

Figure 22B:
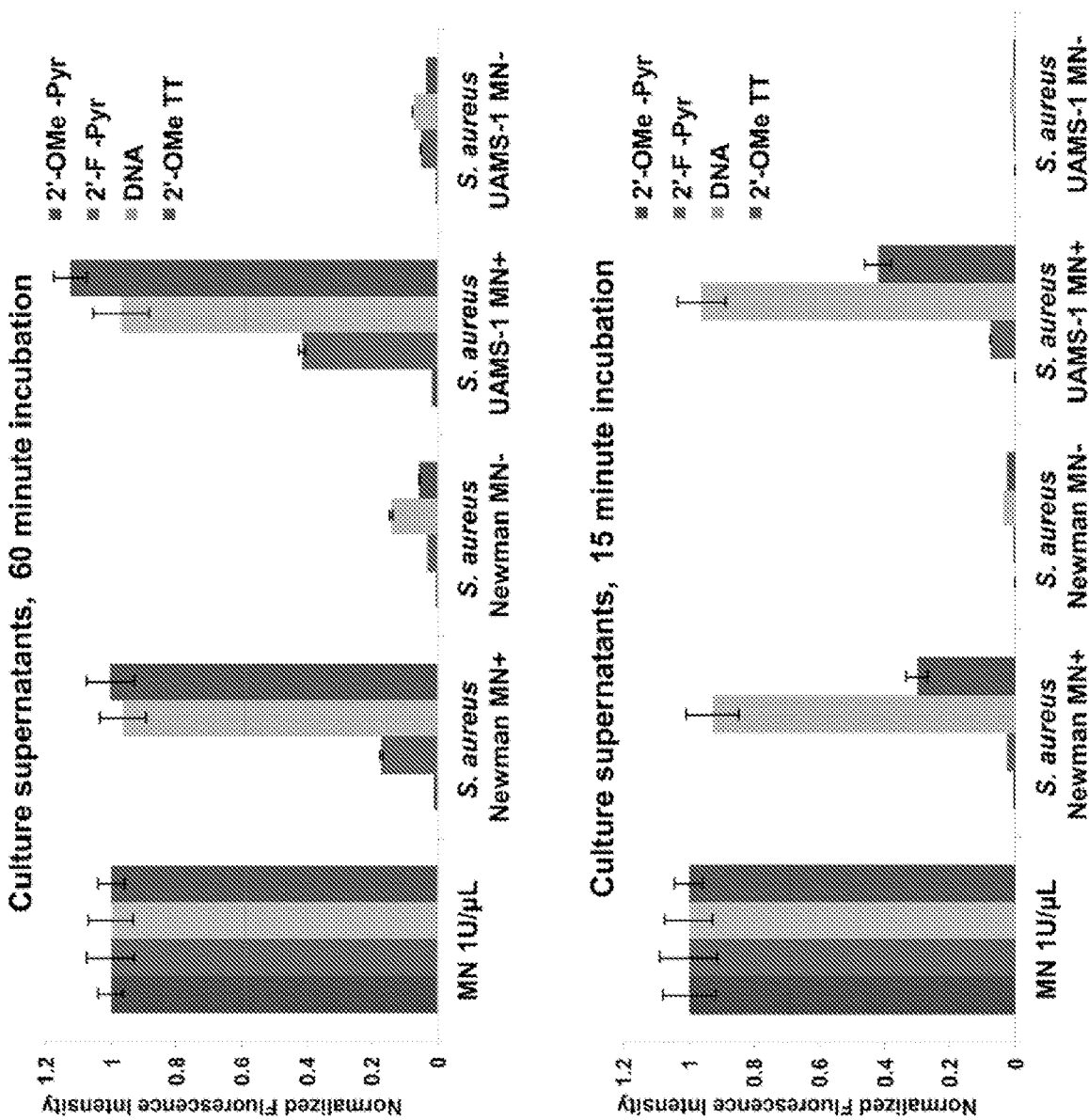

To evaluate the activation of these probes in an environment that more closely models the physiological environment of *S. aureus* infections, the probes were incubated with culture supernatants of the Newman and UAMS-1 strains of *S. aureus* (FIG. 22B). The TT probe was completely digested after a 60-minute incubation in either supernatant (FIG. 22B). The digestion observed here was primarily mediated by MN as incubation of the TT probe in supernatants of MN-negative versions of each strain yielded minimal probe activation (FIG. 22B). In summary, among the serum-nuclease-resistant oligos tested, the TT probe clearly exhibited the greatest sensitivity to digestion by MN, both in purified form and in culture supernatants.

The utility of visible light fluorophores, such as fluorescein, for in vivo imaging is severely limited by tissue autofluorescence and scattering of visible light. In contrast, tissue penetration of near-infrared (NIR) light is much greater and tissue autofluorescence much reduced. Indeed, fluorescence imaging with NIR light is estimated to be feasible at tissue depths of 7-14 centimeters. To prepare an MN-detecting imaging probe based on the TT probe that would be compatible with NIR imaging, Cy5.5, an NIR fluorophore was substituted for the FAM moiety used in the initial TT probe version. The fluorescence of this intact probe was weak, but after digestion with MN, its fluorescence was comparable to that of a control probe, synthesized without fluorescence quenchers.

Next, it was sought to determine whether this probe could enable the detection of a focal *S. aureus* infection in mice. To provide an independent measure of the location and amount of bacteria in infected animals, the lux operon was first incorporated into the Newman strain of *S. aureus* and into an MN-negative modified Newman strain. Mice with unilateral thigh muscle infections (pyomyositis) of these modified bacteria exhibited luminescence that co-localized with gross swelling and, in some animals, externally visible lesions (FIGS. 23C, 23D). Tail vein administration of 3 nanomoles (~1 mg/kg) of Cy5.5-labeled TT probe yielded NIR fluorescence adjacent to the infection site that increased in intensity between 15 and 45 minutes after injection (FIG. 23C). In contrast, injection of the Cy5.5-labeled TT probe into uninfected mice (FIG. 23A) did not yield probe activation in the corresponding regions of these mice. Administration of the unquenched TT probe into uninfected animals resulted in a globally high NIR fluorescence that only began to decline 1-2 hours after injection (FIG. 23B). Finally, the probe activation seen in the *S. aureus*-infected animals that received the TT probe was primarily due to the activity of MN as substantially less TT probe activation was seen adjacent to MN-negative *S. aureus* infections (FIG. 23D). This weak TT probe activation likely results from a distinct *S. aureus* nuclease, TT probe activation has been observed upon incubation with MN-negative *S. aureus* cell suspensions (data not shown).

While these results indicate that the TT probe is specifically activated adjacent to *S. aureus* infection sites by MN in vivo, the reason for the lack of co-localization of the probe activation with the bacterial luminescence was uncertain. A simple and plausible explanation is that the intravenously administered probe may be excluded from the infection site in the setting of our pyomyositis infection model. To address this possibility, the unquenched TT probe was injected into S. aureus-infected mice. The mice were subsequently sacrificed and dissected to provide a clearer picture of the infection sites. As shown in FIG. 23E, the unquenched probe is excluded from direct penetration of the infection site. Activation of the TT probe adjacent to, but not within, the infection site was also observed after sacrifice and dissection, as seen in FIG. 23F. Moreover, histological examination of S. aureus-infected mouse thigh muscles revealed lesions with substantial necrosis, an observation consistent with the notion that the infection sites may have reduced blood perfusion. These results suggest that the probe activation seen in infected animals (FIGS. 23C & 23F) may have resulted from the probe encountering MN that had leaked out of the primary infection site. In any case, the probe was able to detect the presence of the bacteria, despite being excluded from the region where the bacteria, and presumably MN, were most concentrated.

Figure 24A:
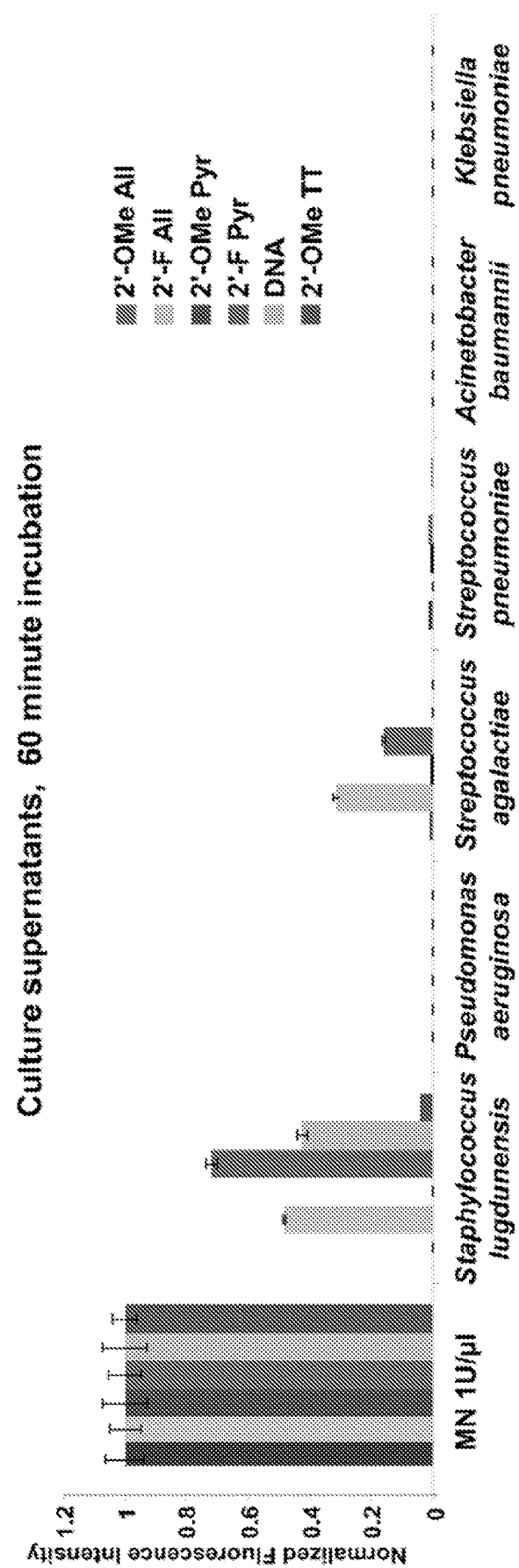
FIGS. 24A-B. Activation of various nucleic acid probes (see Table 4 for probe details) by culture supernatants (A) or cell suspensions (B) of various pathogenic bacterial species. 50 picomoles of each of the indicated probes was incubated with 1 U/µl MN (positive control) in DPBS or with 90% of culture supernatants or concentrated and washed cell suspensions of the indicated bacterial species (prepared as described in Example 6, Materials and Methods) for 60 minutes at 37° C. After the incubations, each reaction was divided into 3 volumes which were read in a fluorescence plate-reader. Mean fluorescence values of all reactions with a given probe were normalized to the mean fluorescence measured with digestion of the probe with 1 U/µl MN. Error bars represent standard deviations of the plate-reader values. Background fluorescence subtractions were carried out (prior to normalization) as follows: The fluorescence of each of the probes incubated in DPBS was subtracted from the corresponding MN-containing reactions. The fluorescence of each of the probes incubated in the appropriate unconditioned culture broth was subtracted from the corresponding culture supernatant reactions. The fluorescence of each of the probes incubated in DPBS plus the autofluorescence of each appropriate bacterial suspension was subtracted from each bacterial suspension reaction.
Figure 24B:
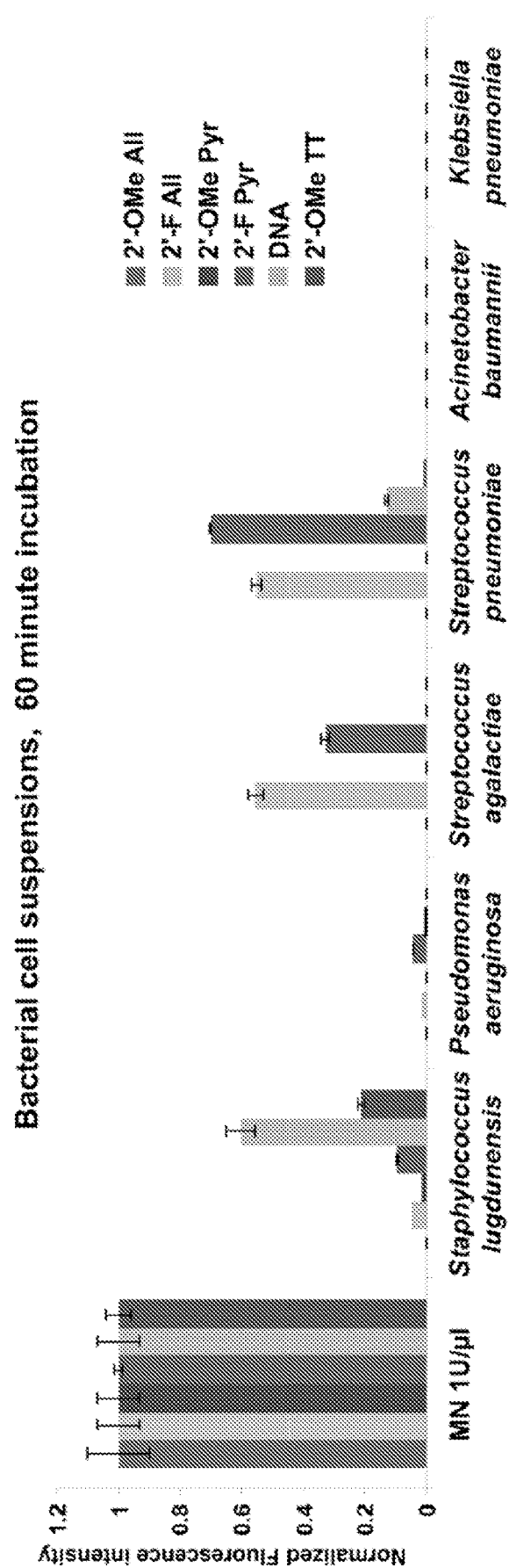
Figure 25:
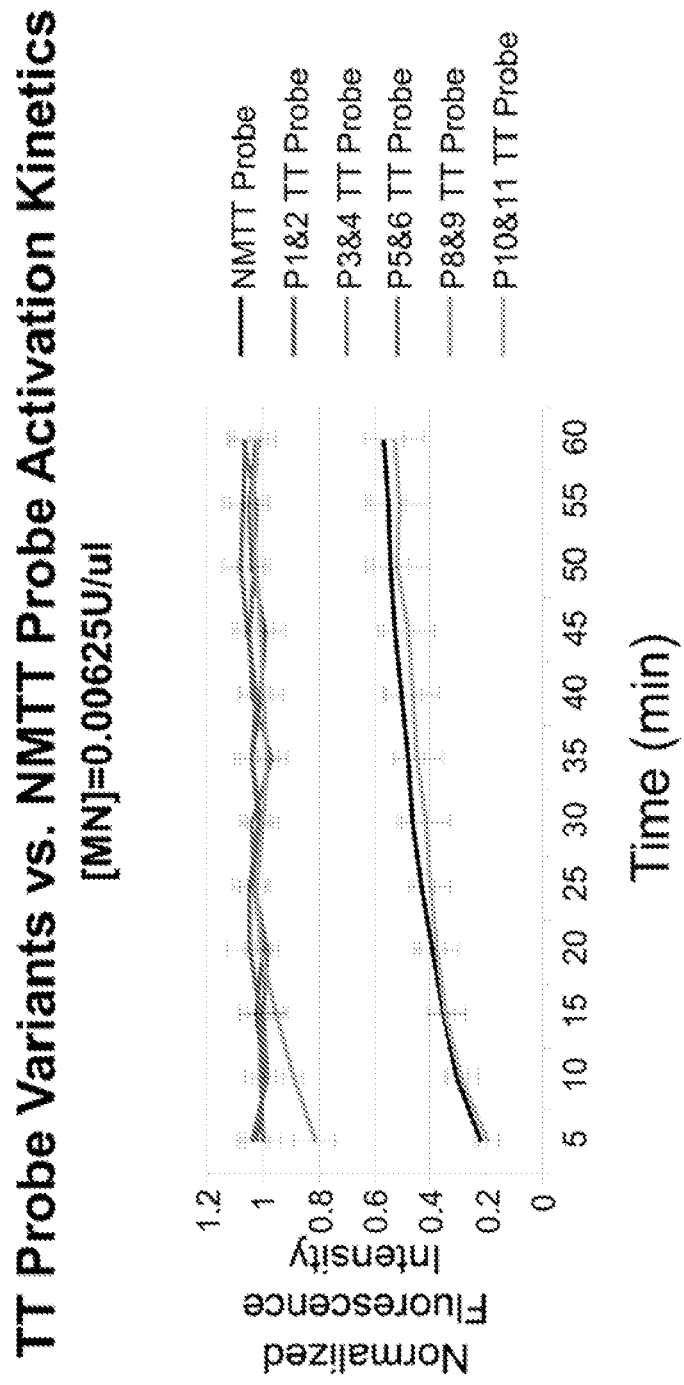
FIG. 25. Comparison of the activation kinetics (digestion with micrococcal nuclease (MN)) of 11 mer quenched fluorescent oligonucleotide probes with a pair of T's in various positions. Note the maximal activation of the probes with the TT closest to the 5'-end of the probe (i.e., positions 1&2, 3&4, 5&6) at the earliest time-point. Also, note that the non-T nucleotides consist of 2'-O-methyl modified U's in all of the probes except the NMTT probe, in which a variety of 2'-O-methyl nucleotides is used. The differences between the NMTT probe and the others could thus be due to these differences in addition to the TT position.
Figure 26:
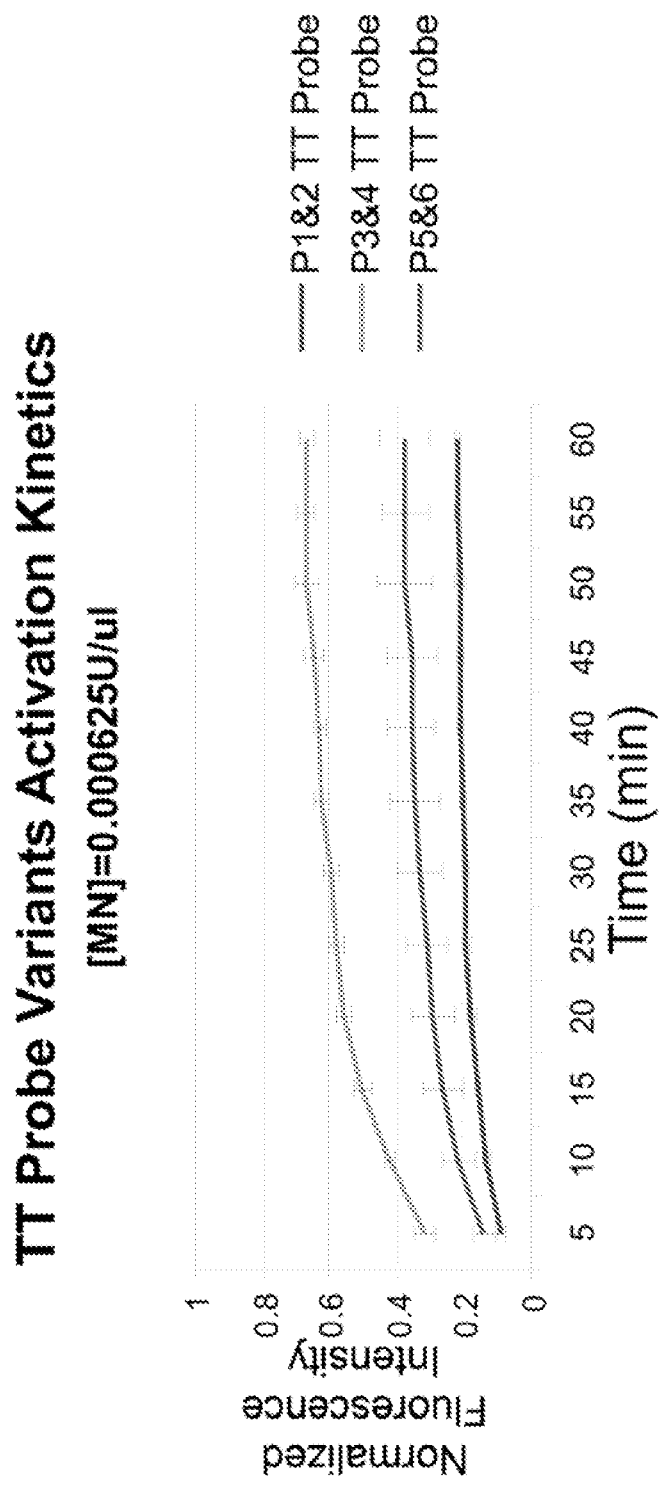
FIG. 26. Comparison of the activation kinetics (digestion with micrococcal nuclease (MN)) of 3×11 mer quenched fluorescent oligonucleotide probes with a pair of T's in different positions. Note that these probes were maximally activated at the earliest time-point measured when a higher concentration of the nuclease (0.00625 U/µl) was used. The 10-fold lower concentration of the enzyme used here provided a means of identifying the most sensitive probe for MN.
Figure 27:
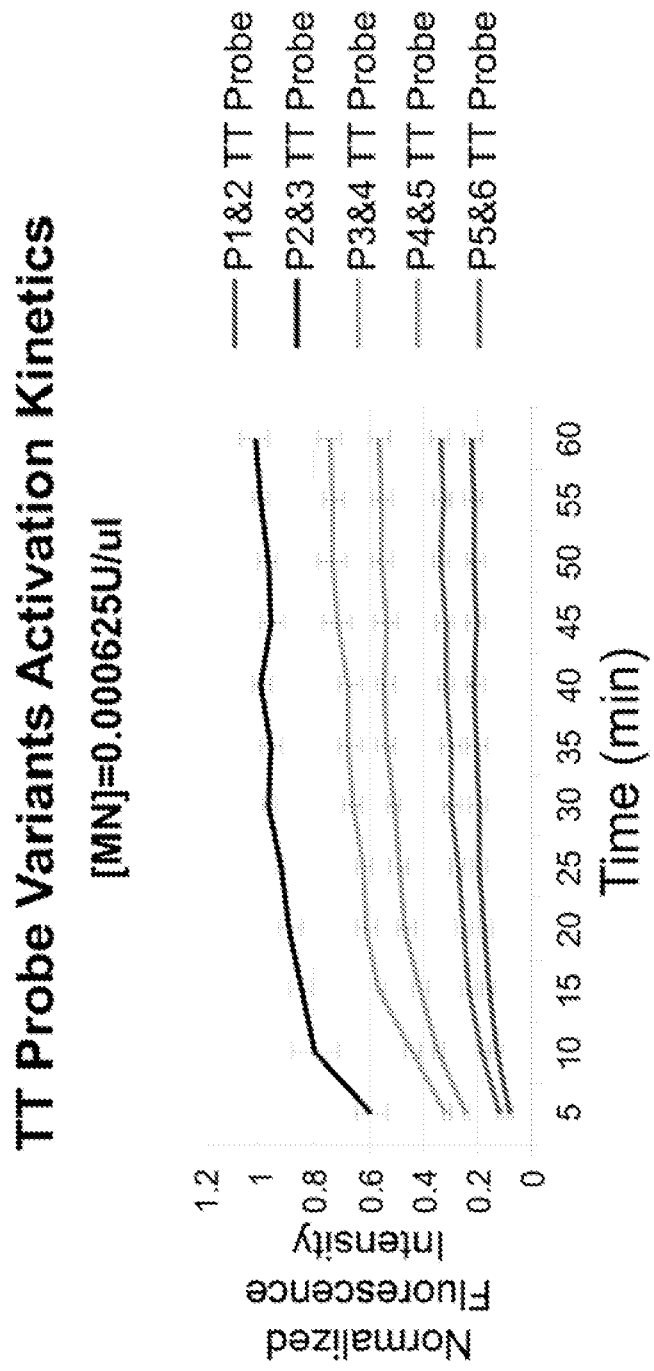
FIG. 27. Comparison of the activation kinetics (digestion with micrococcal nuclease (MN)) of 11 mer quenched fluorescent oligonucleotide probes with a pair of T's in different positions. Inclusion of 2 additional probes with the TT positioned near the 5'-end (P2&3 TT Probe and P4&5 TT Probe) enabled a more precise determination of the optimal position for this pair of nucleotides.
Figure 28:
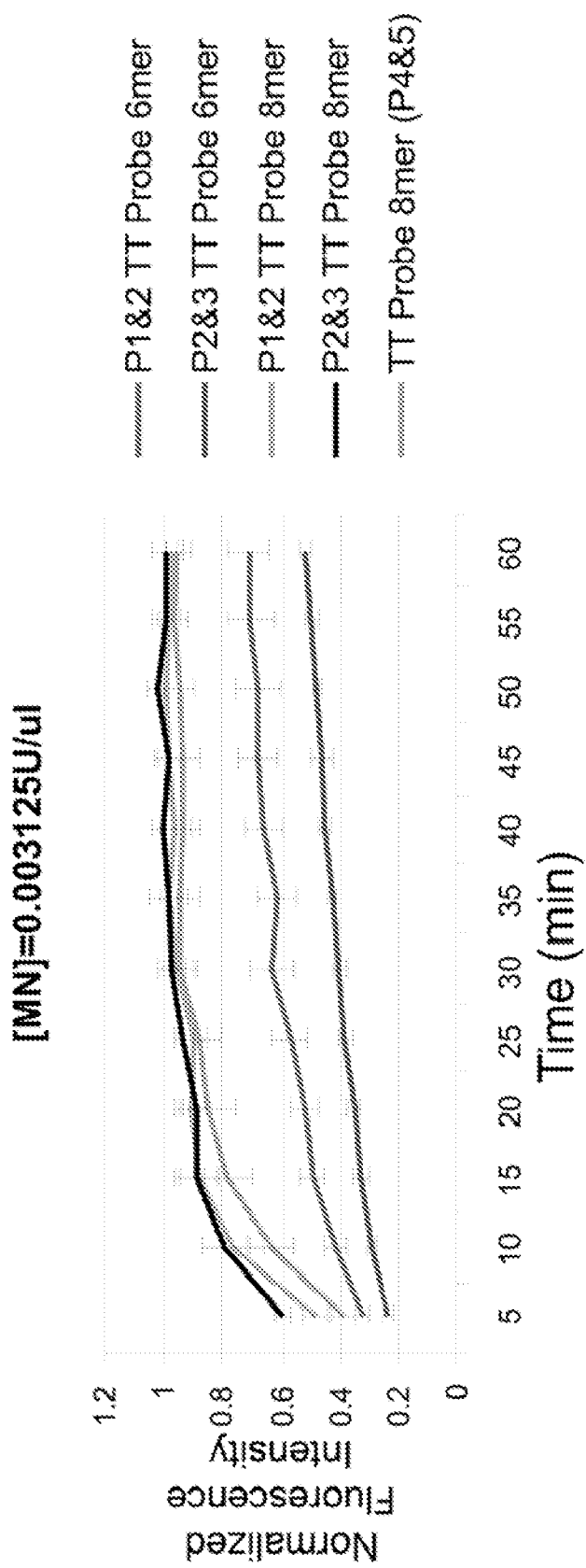
FIG. 28. Comparison of the activation kinetics (digestion with micrococcal nuclease (MN)) of 6 mer and 8 mer quenched fluorescent oligonucleotide probes with a pair of T's in different positions. None of these probes was as sensitive as the best 11 mer probe which yielded similar activation kinetics to the best of these probes when 5-fold less enzyme was used. The optimal position for the TT appears to be 1 &2 for the 6 mer and 2&3 for the 8 mer. Note also that the 8 mers are more sensitive to MN than the 6 mers.
Figure 29:
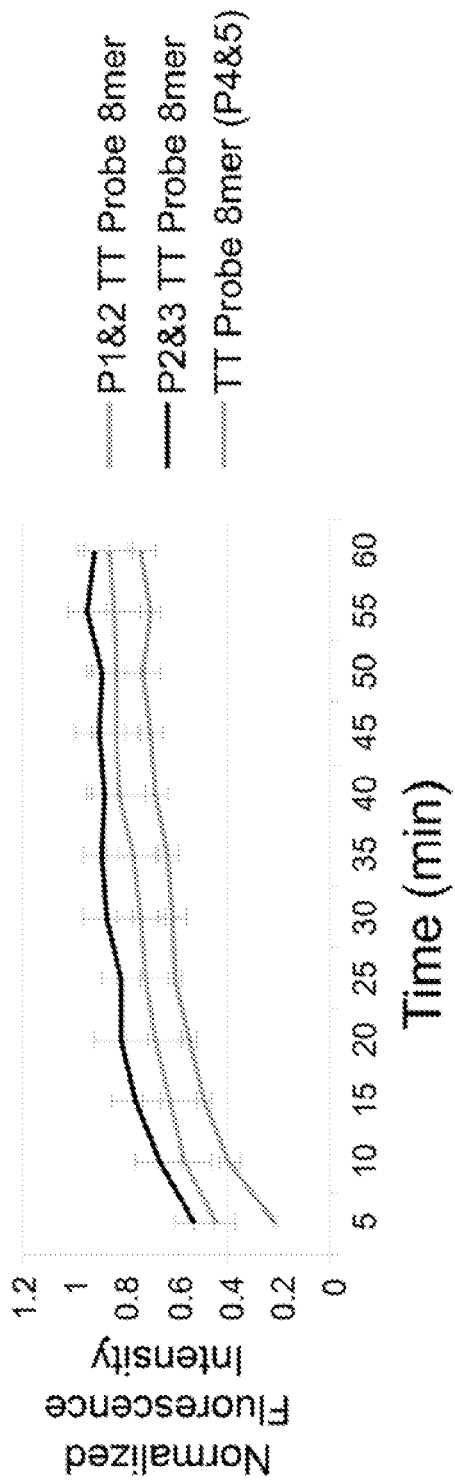
FIG. 29. Comparison of the activation kinetics (digestion with micrococcal nuclease (MN)) of 3×8 mer quenched fluorescent oligonucleotide probes with a pair of T's in different positions. The lower concentration of MN enabled identification of the best of these 3 probes, which were difficult to distinguish when higher concentrations were used. TT positioned in nucleotides 2&3 appears optimal for the 8 mer probe length.

The clinical diagnostic value of assays that non-invasively detect bacteria within infections such as pyomyositis, septic joints, etc., will depend, in part, on their ability to simultaneously identify the type of bacteria that is present. The investigators thus sought to determine whether the TT probe, or any of the others we have tested, might also be activated by nucleases produced by any of a variety of distinct bacterial pathogens that cause some of the same types of infections as S. aureus. Of the culture supernatants of six such bacterial species tested, none substantially digested the TT probe, while Staphylococcus lugdunensis and Streptococcus agalactiae (Group B Streptococcus) supernatants both digested the probes that included 2'-fluoro modified nucleotides (FIG. 24A). Of the bacterial cell suspensions of these cultures, only the Staphylococcus lugdunensis (of the same genus as S. aureus) produced any appreciable digestion (~25%) of the TT probe in a one-hour incubation (FIG. 24B). Bacterial cell suspensions of Streptococcus agalactiae and Streptococcus pneumoniae both digested the probes that included 2'-fluoro modified nucleotides (FIG. 24B). Together, these results demonstrate a high degree of specificity of the TT probe, and suggest that similar probes with specificity for bacterial nucleases of a variety of species of bacterial pathogens may also be identified. Importantly, the oligonucleotide probes digested by the Streptococcus agalactiae and Streptococcus pneumoniae cultures are resistant to serum nucleases; the nucleases of these bacteria thus satisfy a critical requirement for the approach we have developed for S. aureus.

The present study is the first to demonstrate the non-invasive detection of a bacterial infection in animals with an activatable imaging probe. A similar molecular imaging approach to that described here, in which quenched fluorescent peptide-based probes that are activated by tumor-specific proteases, has provided a valuable imaging platform for cancer imaging. Because such activatable probes do not produce fluorescence until the probe encounters its target, the result is a highly sensitive means of target detection. Importantly, while near-infrared fluorescence (NIRF) imaging is currently only used in a limited capacity in the clinic (e.g., retinal angiography, cardiac function, hepatic output, sentinel lymph node dissection and colon polyp identification), advances in NIRF instrumentation are likely to expand its applicability in the near future. These developments include devices such as endoscopes with fluorescence imaging capabilities and external NIRF scanners.

TABLE 6

Nuclease probe sequences and modifications.

| Probe | Sequence | SEQ ID NO |
|---|---|---|
| FAM-Pyr 2'F-ZRQ | FAM-fU fC fU fC rG fU rA fC rG fU fU fC-ZEN-RQ | 43 |
| FAM-Pyr 2'OMe-ZRQ | FAM-mU mC mU mC rG mU rA mC rG mU mU mC-ZEN-RQ | 44 |
| FAM-All 2'F-ZRQ | FAM-fU fC fU fC fG fU fA fC fG fU fU fC-ZEN-RQ | 45 |
| FAM-All 2'OMe-ZRQ | FAM-mU mC mU mC mG mU mA mC mG mU mU mC-ZEN-RQ | 46 |
| FAM-DNA-ZRQ | FAM-T T C C T T C C T C-ZEN-RQ | 47 |
| FAM-2'-OMe + TT-ZRQ_ | FAM-mC mU mC mG T T mC mG mU mU mC-ZEN-RQ | 48 |
| Cy5.5-2'-OMe + TT-ZRQ_ | Cy5.5-mC mU mC mG T T mC mG mU mU mC-ZEN-RQ | 48 |
| Cy5.5-2'-OMe + TT-invT | Cy5.5-mC mU mC mG T T mC mG mU mU mC-InvdT | 50 |

FAM = FAM fluorophore (fluorescein amidite);
ZEN = IDT "ZEN" fluorescence quencher;
RQ = IDT Iowa Black ® RQ fluorescence quencher;
mA = 2'-O-methyl-Adenosine;
mC = 2'-O-methyl-Cytidine;
mG = 2'-O-methyl-Guanosine;
mU = 2'-O-methy-Uridine;
fA = 2'-fluoro-Adenosine;
fC = 2'-fluoro-Cytidine;
fG = 2'-fluoro-Guanosine;
fU = 2'-fluoro-Uridine;
Nucleotides written in bold are deoxy nucleotides (DNA);
InvdT = inverted dT.

Materials and Methods

Oligonucleotide Probe Synthesis and Purification

Oligonucleotide probes were synthesized and purified at Integrated DNA Technologies (IDT), Coralville, Iowa Briefly, all the FAM-labeled probes were synthesized using standard solid phase phosphoramidite chemistry, followed by high performance liquid chromatography (HPLC) purification. For the Cy5.5-labeled probes, the sequences were first synthesized with ZEN and Iowa Black quenchers or inverted dT on the 3'-ends and amine on the 5'-ends using the standard solid phase phosphoramidite chemistry, and purified with HPLC. These purified sequences were then set to react with Cy5.5 NHS ester (GE Healthcare, Piscataway, N.J.) to chemically conjugate the Cy5.5 label on the sequences. The Cy5.5-labeled probes were further purified with a second HPLC purification. All probe identities were confirmed by electron spray ionization mass spectrometer (ESI-MS) using an Oligo HTCS system (Novatia LLC, Princeton, N.J.). The measured molecular weights are within 1.5 Daltons of the expected molecular weights. The purity of the probes was assessed with HPLC analysis and is typically greater than 90%. Quantitation of the probes was achieved by calculating from their UV absorption data and their nearest-neighbor-model-based extinction coefficients at 260 nm. Extinction coefficients of 2'-O-methyl-nucleotides and 2'-fluoro-nucleotides are assumed to be the same as that of RNA.

Fluorescence Plate-Reader Nuclease Assays

Fluorescence plate reader assays were carried out as described (Hernandez et al., 2012). Briefly, for each reaction, 1 µl of a stock solution of each probe (50 µM concentration) was combined with 9 µl of each sample (buffer, buffer plus recombinant nuclease, serum, culture supernatant, culture broth or washed bacteria) and incubated at 37° C. for the time periods indicated in the figures. 290 µl of PBS supplemented with 10 mM EDTA and 10 mM EGTA was then added to each and 95 µl of each diluted reaction was loaded per well into a 96-well plate (96F non-treated black microwell plate (NUNC)). Fluorescence levels were measured with an Analyst HT fluorescence plate reader (LJL Biosystems).

Background fluorescence levels of probes incubated in buffer or broth, and autofluorescence levels of the various preparations were determined and subtracted from the probe-activation reaction values as described in the figure legends. Purified micrococcal nuclease was obtained from Worthington Biochemical Corporation (Lakewood, N.J.). Dulbecco's phosphate-buffered saline (DPBS) containing physiological levels of calcium and magnesium, was obtained from Invitrogen (Carlsbad, Calif.). Human serum was obtained from Sigma-Aldrich (St. Louis, Mo.) and mouse serum (C57BL6) was obtained from Valley Biomedical Inc. (Winchester, Va.).

Bacterial Cultures and Growth Conditions

Bacteria were maintained in tryptic soy broth (TSB), Luria Bertani (LB) or Todd Hewitt+yeast (THY) broth as defined in Table 4 for each strain. To prepare cultures for assays, overnight cultures were sub-cultured 1:500 into 5 ml fresh broth and grown for 24 hr at 37° C. with shaking at 200 rpm. The only exceptions were *Streptococcus pneumoniae* and *Streptococcus agalactiae* (Group B *Streptococcus*), which were grown under static conditions in a 37° C. incubator supplemented with 5.0% $CO_2$. To prepare spent media for nuclease assays, 1 ml of each culture was centrifuged at 6,000×g for 10 min and the supernatant was saved. For preparation of bacteria suspensions for nuclease assays, pelleted bacteria were washed with 1 ml DPBS and re-suspended in 100 µl of DPBS.

Genetic Manipulation of *S. aureus*

Bacteriophage 11 was used to transduce the *P. luminescens* luxABCDE genes from AH1362 into strains Newman and Newman nuc::LtrB as previously described (Novick, R. P. (1991) Genetic systems in staphylococci. Methods Enzymol 204, 587-636.). Transductants carrying the lux genes were selected on tryptic soy agar (TSA) with kanamycin (Kan) supplemented at 50 µg/ml. The resulting strains were confirmed for bioluminescence production (lux+) using a Tecan Infinity 200M plate and saved (see Table 7).

TABLE 7

Bacterial strains

| Strain name | Common name of strain lineage | Genotype | Media used | Reference |
| --- | --- | --- | --- | --- |
| *Staphylococcus aureus* | | | | |
| AH1178 | Newman | Wild type | TSB | (1) |
| AH2495 | Newman | nuc::LtrB | TSB | (2) |
| AH2600 | Newman | luxABCDE-Kan | TSB | This work |
| AH2672 | Newman | nuc::LtrB luxABCDE-Kan | TSB | This work |
| AH759 | UAMS-1 | Wild type | TSB | (3) |
| AH893 | UAMS-1 | Δnuc | TSB | (4) |
| AH1362 | Xen29 | luxABCDE-Kan | TSB | (5) |
| *Staphylococcus lugdunensis* | | | | |
| AH2160 | N920143 | Wild type | TSB | (6) |
| *Streptococcus pneumoniae* | | | | |
| AH1102 | ATCC 6301 | Wild type | THY | ATCC |
| *Streptococcus agalactiae* | | | | |
| AH2771 | MN SI | Wild type | THY | (7) |

TABLE 7-continued

Bacterial strains

| Strain name | Common name of strain lineage | Genotype | Media used | Reference |
|---|---|---|---|---|
| *Acinetobacter baumannii* | | | | |
| AH2669 | M2 | Wild type | LB | (8) |
| *Pseudomonas aeruginosa* | | | | |
| AH71 | PAO1 | Wild type | LB | (9) |
| *Klebsiella pneumoniae* | | | | |
| AH2687 | 43816 | Wild type | LB | (10) |

Table 7 References
(1). Baba, T., Bae, T., Schneewind, O., Takeuchi, F., and Hiramatsu, K. (2008) Genome sequence of *Staphylococcus aureus* strain Newman and comparative analysis of staphylococcal genomes: polymorphism and evolution of two major pathogenicity islands, *J. Bacteriol.* 190, 300-310.
(2). Kiedrowski, M. R., Kavanaugh, J. S., Malone, C. L., Mootz, J. M., Voyich, J. M., Smeltzer, M. S., Bayles, K. W., and Horswill, A. R. (2011) Nuclease modulates biofilm formation in community-associated methicillin-resistant *Staphylococcus aureus*, *PLoS ONE* 6, e26714.
(3). Gillaspy, A. F., Hickmon, S. G., Skinner, R. A., Thomas, J. R., Nelson, C. L., and Smeltzer, M. S. (1995) Role of the accessory gene regulator (agr) in pathogenesis of staphylococcal osteomyelitis, *Infect. Immun.* 63, 3373-3380.
(4). Beenken, K. E., Mrak, L. N., Griffin, L. M., Zielinska, A. K., Shaw, L. N., Rice, K. C., Horswill, A. R., Bayles, K. W., and Smeltzer, M. S. (2010) Epistatic relationships between sarA and agr in *Staphylococcus aureus* biofilm formation, *PLoS ONE* 5, e10790.
(5). Xiong, Y. Q., Willard, J., Kadurugamuwa, J. L., Yu, J., Francis, K. P., and Bayer, A. S. (2005) Real-time in vivo bioluminescent imaging for evaluating the efficacy of antibiotics in a rat *Staphylococcus aureus* endocarditis model, *Antimicrob. Agents Chemother.* 49, 380-387.
(6). Heilbronner, S., Holden, M. T., van Tonder, A., Geoghegan, J. A., Foster, T. J., Parkhill, J., and Bentley, S. D. (2011) Genome sequence of *Staphylococcus lugdunensis* N920143 allows identification of putative colonization and virulence factors, *FEMS Microbiol Lett* 322, 60-67.
(7). Schlievert, P. M., Varner, M., and Galask, R. P. (1983) Endotoxin enhancement as a possible cause of group B streptococcal neonatal sepsis, *Obstet. Gynecol.* 61, 588-592.
(8). Niu, C., Clemmer, K. M., Bonomo, R. A., and Rather, P. N. (2008) Isolation and characterization of an autoinducer synthase from *Acinetobacter baumannii*, *J Bacteriol* 190, 3386-3392.
(9). Stover, C. K., Pham, X. Q., Erwin, A. L., Mizoguchi, S. D., Warrener, P., Hickey, M. J., Brinkman, F. S., Hufnagle, W. O., Kowalik, D. J., Lagrou, M., Garber, R. L., Goltry, L., Tolentino, E., Westbrock-Wadman, S., Yuan, Y., Brody, L. L., Coulter, S. N., Folger, K. R., Kas, A., Larbig, K., Lim, R., Smith, K., Spencer, D., Wong, G. K., Wu, Z., Paulsen, I. T., Reizer, J., Saier, M. H., Hancock, R. E., Lory, S., and Olson, M. V. (2000) Complete genome sequence of *Pseudomonas aeruginosa* PAO1, an opportunistic pathogen, *Nature* 406, 959-964.
(10). Lau, H. Y., Clegg, S., and Moore, T. A. (2007) Identification of *Klebsiella pneumoniae* genes uniquely expressed in a strain virulent using a murine model of bacterial pneumonia, *Microb Pathog* 42, 148-155.

Infection of Mice with *S. aureus*

*S. aureus* cultures were prepared for injection into mice as follows. 5 ml of TSB supplemented with Kan (50 µg/ml) were inoculated with frozen stocks of MN-expressing or MN-negative lux+*S. aureus* of the strain Newman genetic background (Table 6). Cultures were grown overnight at 37° C. with shaking at 200 rpm, and each strain was sub-cultured 1:100 into 5 ml of fresh media and grown for another 12 hr at 37° C. with shaking. Bacteria were washed once with PBS and resuspended in PBS to an approximate cell density of $\sim 2 \times 10^8$ CFU/ml for injection into mice. Bacteria were serially diluted, plated on TSA, and incubated at 37° C. to determine bacterial concentration.

For animal infections, 50 µl of $2 \times 10^8$ CFU/ml ($1 \times 10^7$ CFU total) was injected intramuscularly (thigh muscle) in 6-8 week old C57BL6 female mice under isoflurane anesthesia. Mice were shaved prior to injections. Injection sites were evaluated with bioluminescence imaging immediately thereafter. Mice were imaged or sacrificed for imaging or histology 48 hours after injections.

In Vivo Evaluation of Nuclease-Activated Probes

Luminescence and epifluorescence imaging was performed with a Xenogen IVIS 200 imaging system (Caliper). Mice were anesthetized with 2% isoflurane gas anesthesia and placed on the imaging platform inside the optical system for dorsal imaging. Luminescence images were recorded with a 1 minute exposure time and an open emission filter. Epifluorescence images were acquired with a 1 second exposure time and excitation and emission filters appropriate for the Cy5.5 dye. To avoid saturation, the exposure time for the acquisition of epifluorescence images of the mice injected with the unquenched TT probe was reduced to 0.5 seconds. Bioluminescence images were acquired prior to probe injections. Fluorescence images were acquired prior to and following tail-vein injections (time points are indicated in figures) of the probes. For probe administration, 3 nanomoles of each probe diluted in PBS were injected via tail vein in a total volume of 120λ IVIS 4.2 software was used to perform acquisition, imaging analysis and preparation of pseudocolored overlays of luminescence, fluorescence and grayscale images. Imaging of mice following sacrifice and dissection was carried out as described for the live animal imaging, but with field of view adjusted for image acquisitions.

Histological Analysis of Infected and Uninfected Muscle Tissue

Mice were euthanized via carbon dioxide intoxication and gross lesions were photographed with a digital camera before and after removal of the skin. Soft tissues of the *S. aureus*-infected (right), and the corresponding portion of the uninfected (left) leg were carefully dissected and fixed in 10% neutral buffered formalin for 48 hours at room temperature. The fixed tissues were gross-sectioned and then routinely processed in a series of alcohol and xylene baths, paraffin-embedded, and 4 µm sections were stained with hematoxylin and eosin (HE), or Gram stain as previously described (Stoltz, D A, et al. Cystic Fibrosis Pigs Develop Lung Disease and Exhibit Defective Bacterial Eradication at Birth. Science Translational Medicine, April 28; 2(29): 29ra31, 2010). Slides were examined by a veterinary pathologist (DKM) for histopathologic interpretation. High resolution digital images were acquired with a DP71 camera (Olympus) mounted on a BX51 microscope (Olympus) with MicroSuite Pathology Edition Software (Olympus).

Example 11

TT Probe Optimization

Measurement of Probe Activation Kinetics by Micrococcal Nuclease (MN) of *Staphylococcus aureus*:

Probes were diluted in Dulbecco's Phosphate-Buffered Saline (DPBS) (includes physiological levels of calcium and magnesium) and combined with the indicated amounts of MN and incubated at room temperature for 60 minutes. Fluorescence was measured during incubation time. Fluorescence of each probe incubated with DPBS (without MN added) was also measured and subtracted from the probe+MN values. The fluorescence values of each probe incubated with MN were also normalized to the values of control reactions in which each probe was incubated with a high concentration (1 unit per microliter) of MN (typically yielding complete probe digestion). The graphed kinetics curves thus indicate the progression of probe digestion towards its maximally activated state of 1. Fluorescence levels were measured with an HT Analyst fluorescence plate-reader. (FIGS. 25-29 and 33)

Measurement of Probe Stability and Activation by MN in Mouse Serum:

Probes were incubated in 80% mouse serum for 60 minutes with or without 1 unit/microliter MN at 37° C. Control reactions included digestion of probes in DPBS with 1 unit/microliter MN, also incubated at 37° C. for 60 minutes. After the 60 minute period, the 10 microliter reactions were "stopped" via addition of 290 microliters of a buffer solution containing chelators of divalent cations and fluorescence levels were measured in triplicate. Fluorescence ratios of each probe incubated in serum (with or without MN) divided by each probe incubated in DPBS were then plotted. Ratios of each probe incubated in serum with MN divided by each probe incubated in serum alone were also plotted. Fluorescence levels were measured with an HT Analyst fluorescence plate-reader. (FIGS. 30-32, 34 and 35)

Figure 36:
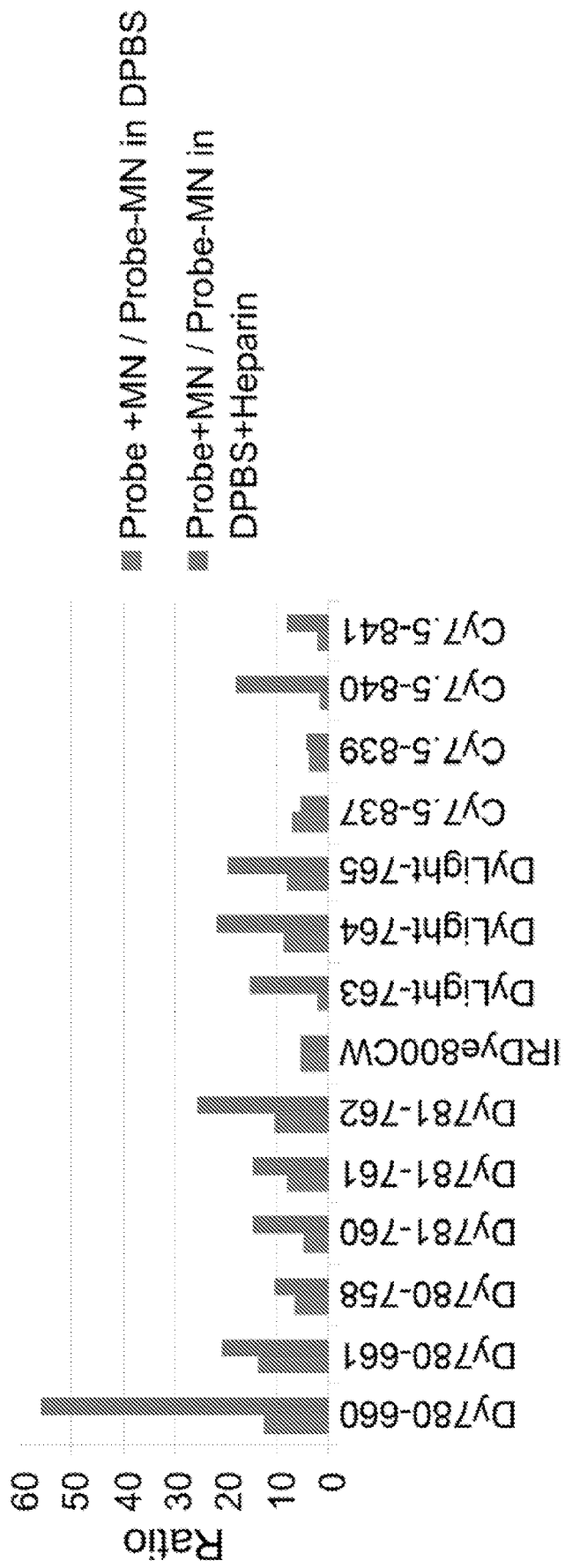
FIG. 36. Digestion of TT probes (oligonucleotide portion is identical to the NMTT probe) in which the indicated NIR fluorophores are used in place of FAM and the QC-1 quencher is used at the 3'-end. Probes were incubated in buffer only or buffer plus nuclease and ratio of digested versus buffer only fluorescence is plotted. Digests were carried out with or without heparin to examine the effect of this compound prior to measurement of probe digestion in heparinized blood. Note that all ratios indicate some degree of probe activation via digestion. (3-digit numbers following some of the probe names indicate synthesis variants of the probes. Upon purification of the probes with HPLC, different purification peaks were separately collected and assigned these numbers.)
Figure 37:
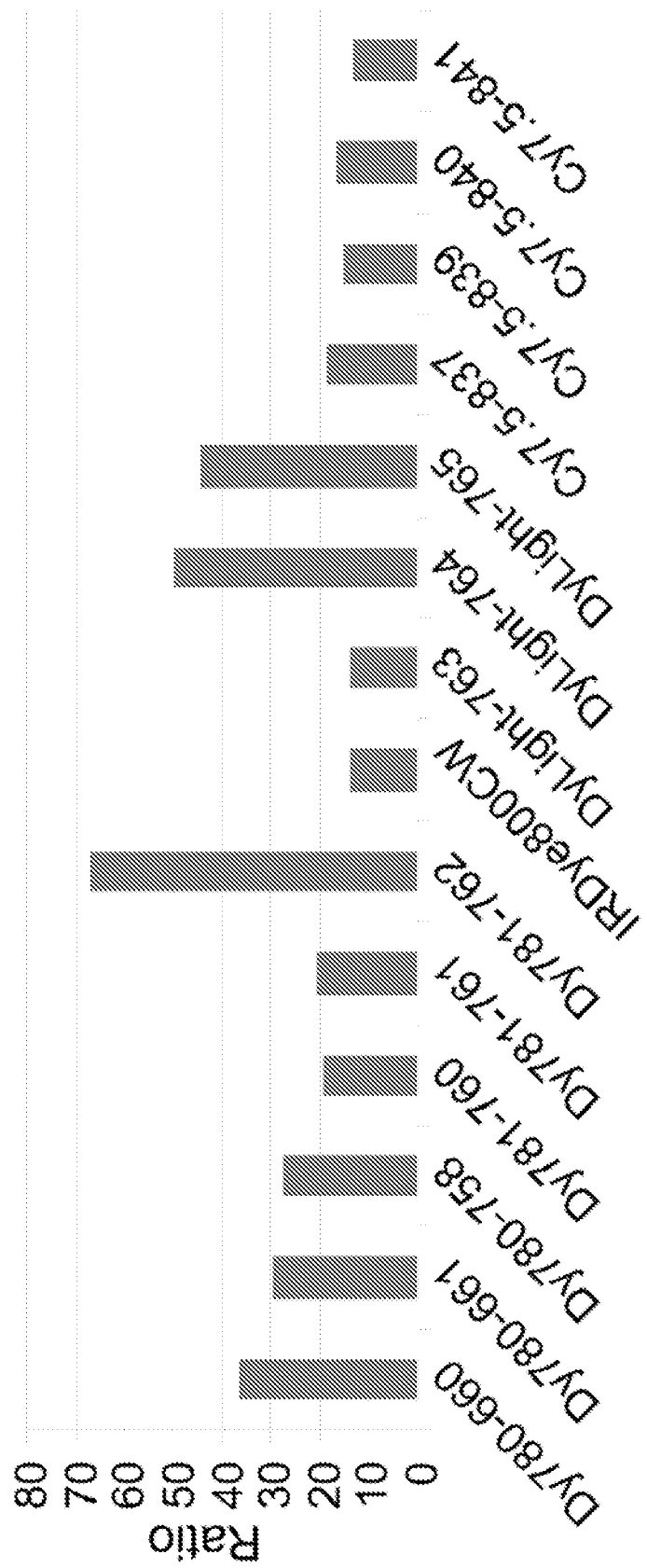
FIG. 37. Activation of near-infrared probes in whole blood. Ratios of fluorescence of probe incubated in whole mouse blood plus micrococcal nuclease for 60 minutes divided by fluorescence of probe incubated in whole mouse blood without nuclease for 1 minute. Higher ratios indicate better probe performance.
Figure 38:
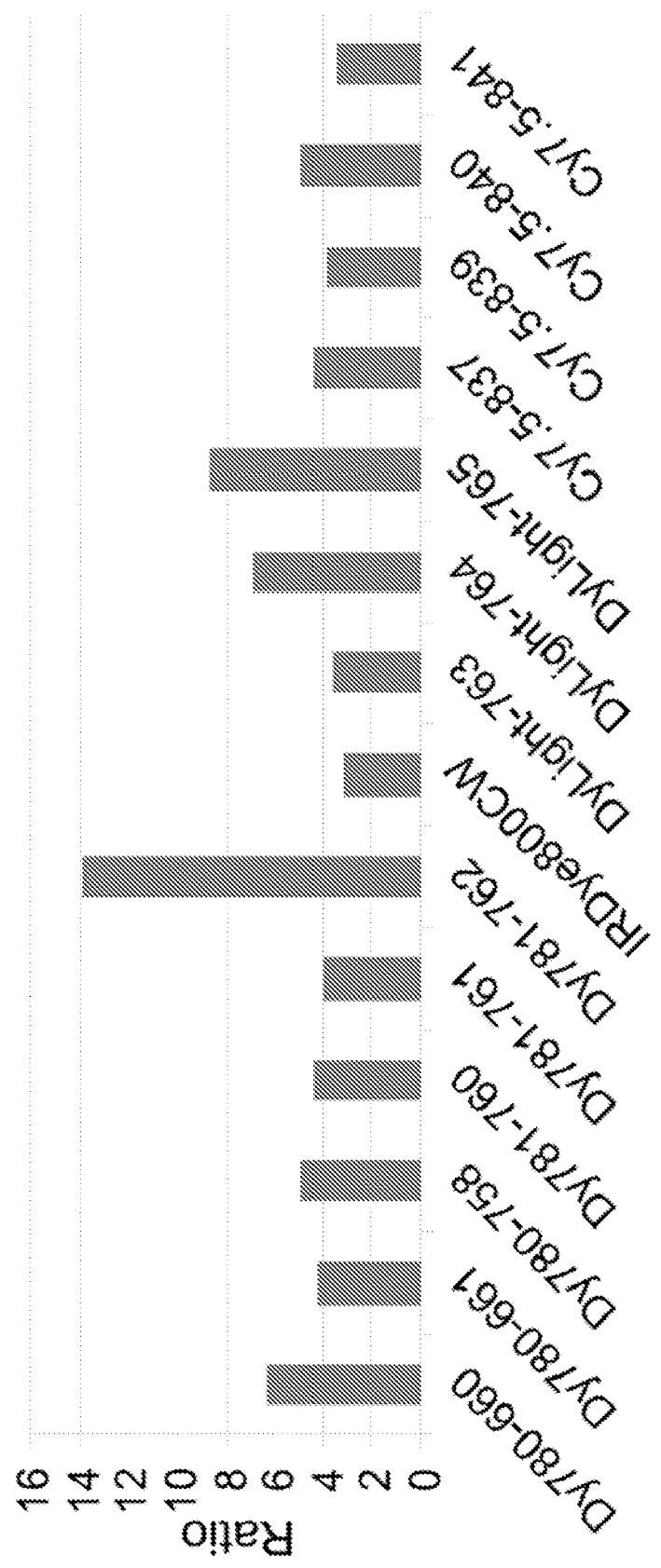
FIG. 38. Fluorescence Ratios of TT Probes (with NIR fluorophore/quencher pairs) incubated in blood for 60 minutes versus 1 minute. As no nuclease was added, this is just a measure of probe stability in blood. The lower the ratio, the greater the stability.

Measurements of Near-Infrared Fluorophore-Labeled Probes in Buffer and Heparinized Mouse Blood:

Probes were incubated in DPBS, with or without 1 unit per microliter MN or in 88% heparinized mouse blood with or without 1 unit per microliter MN for 1 hour at 37° C. Control reactions included incubation of probes in 88% heparinized DPBS with or without 1 unit per microliter MN for 1 hour at 37° C. and incubation in 88% heparinized mouse blood for 1 minute at room temperature. The fluorescence levels were measured with a LI-COR Odyssey near-infrared fluorescence scanner. (FIGS. 36-38)

Table 6 below provides a list of probes and their various sequences, fluorophores and fluorescence quenchers used in this work.

Key findings of this work include the following:

The position of the TT within the oligonucleotide portion of the probes has a substantial impact the sensitivity of the probe to digestion by MN, with TT positions close to the 5'-end yielding the greatest sensitivity to MN. In particular, TT located at positions 2 and 3 was optimal in 8 mer and 11 mer oligonucleotides (FIGS. 27 and 29) and TT located at positions 1 and 2 of 6 mer oligonucleotides (FIG. 28) yielded the highest MN sensitivity.

In these studies the TT consists of unmodified deoxythymidines.

Figure 34:
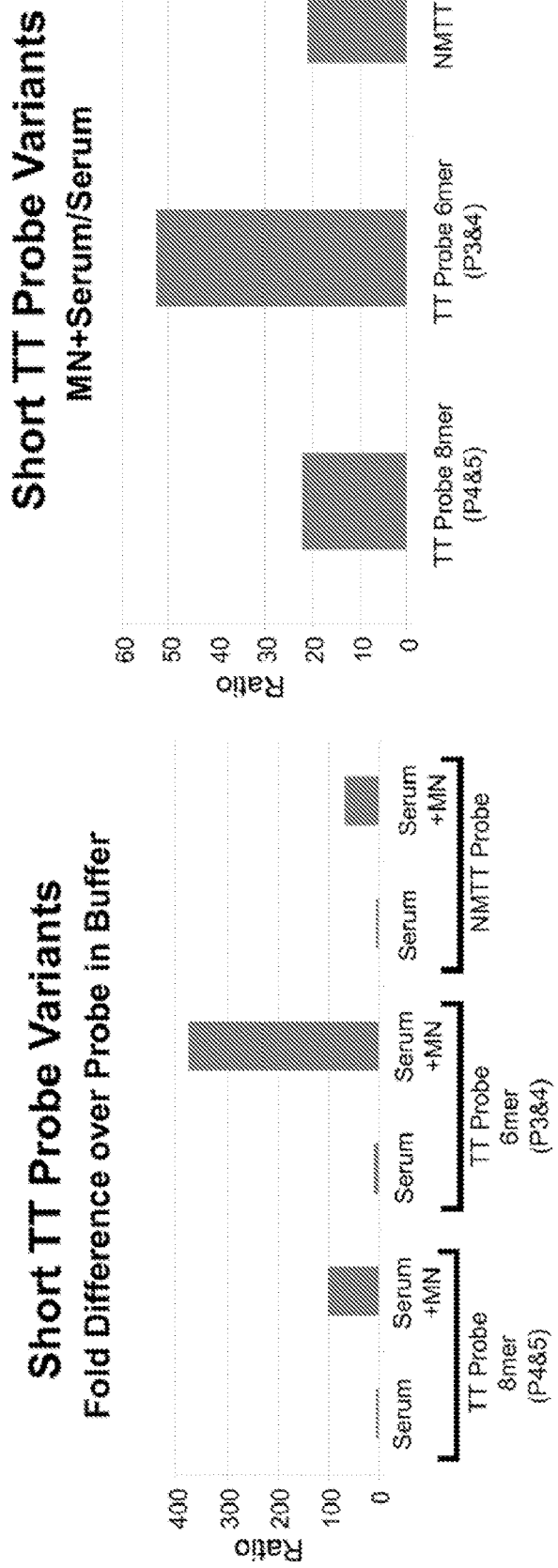
FIG. 34. Serum stability and activation by MN in serum of the NMTT probe (included as a control) and 2 probes of variable length composed of TT flanked by several 2'-O-methyl U's. Note the greater than ~50-fold ratio of the MN-digested (in serum) versus serum-only fluorescence of the TT Probe 6 mer (right panel). While this ratio is superior to that of the NMTT probe, the TT Probe 6 mer, like the other short probes, was found to be less sensitive than the NMTT probe to micrococcal nuclease digestion in kinetics assays.
Figure 35:
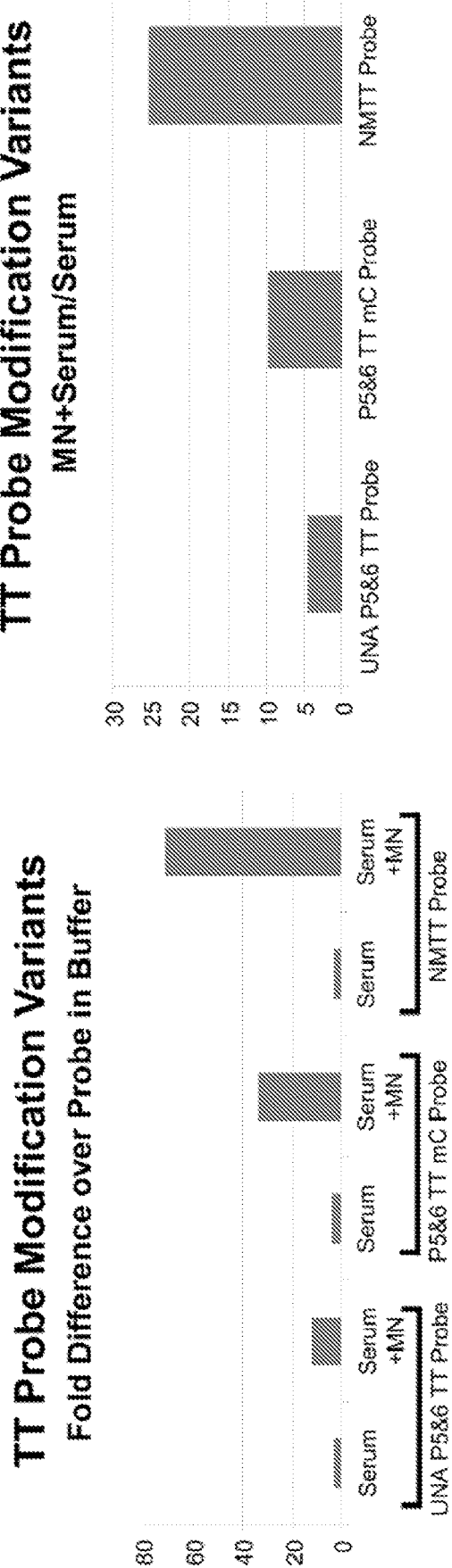
FIG. 35. Serum stability and activation by MN in serum of the NMTT probe (included as a control) and 2 probes with a TT flanked by several 2'-O-methyl C's (P5&6 TT mC Probe) or by several unlocked nucleic acid U's (UNA P5&6 TT Probe). Both of these alternative probe configurations is digested by MN in serum. However, neither performs as well as the NMTT probe in this assay.

A 6 nucleotide long oligonucleotides (TT Probe 6 mer) yielded greater stability in serum than the well-characterized NMTT Probe. (FIG. 34)

Figure 32:
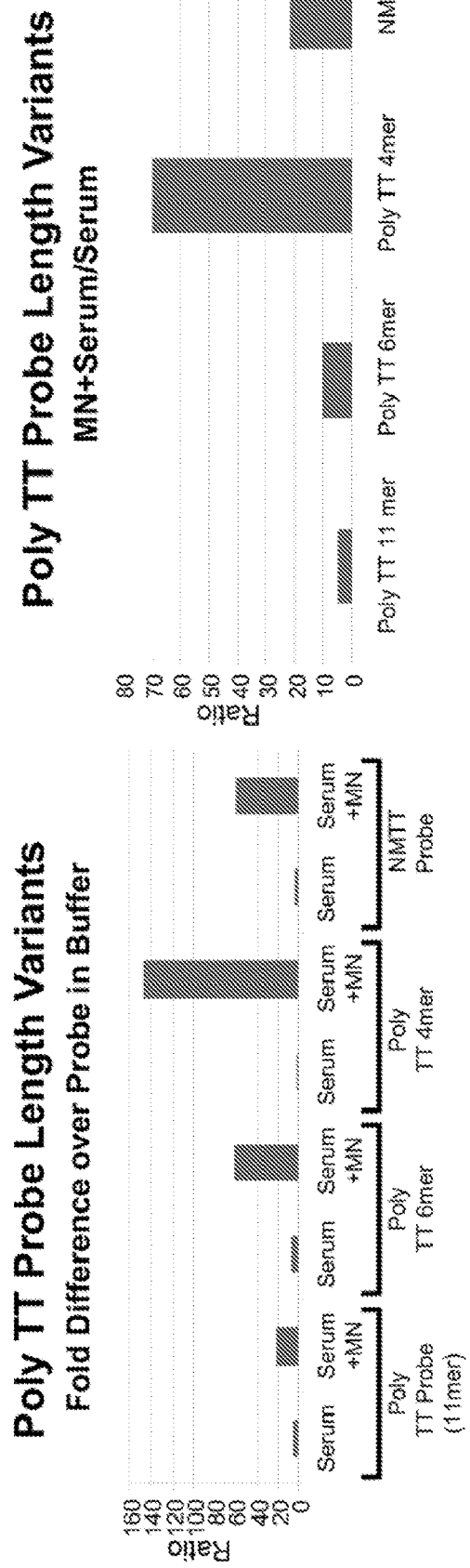
FIG. 32. Serum stability and activation by MN in serum of the NMTT probe (included as a control) and 3 probes of variable length composed of a string of T's. Note the ~70-fold ratio of the MN-digested (in serum) versus serum-only fluorescence of the Poly TT 4 mer (right panel). Despite the fact that the oligonucleotide portion of this probe consists of unmodified nucleotides (DNA T's), it is very stable in serum (left panel).
Figure 33:
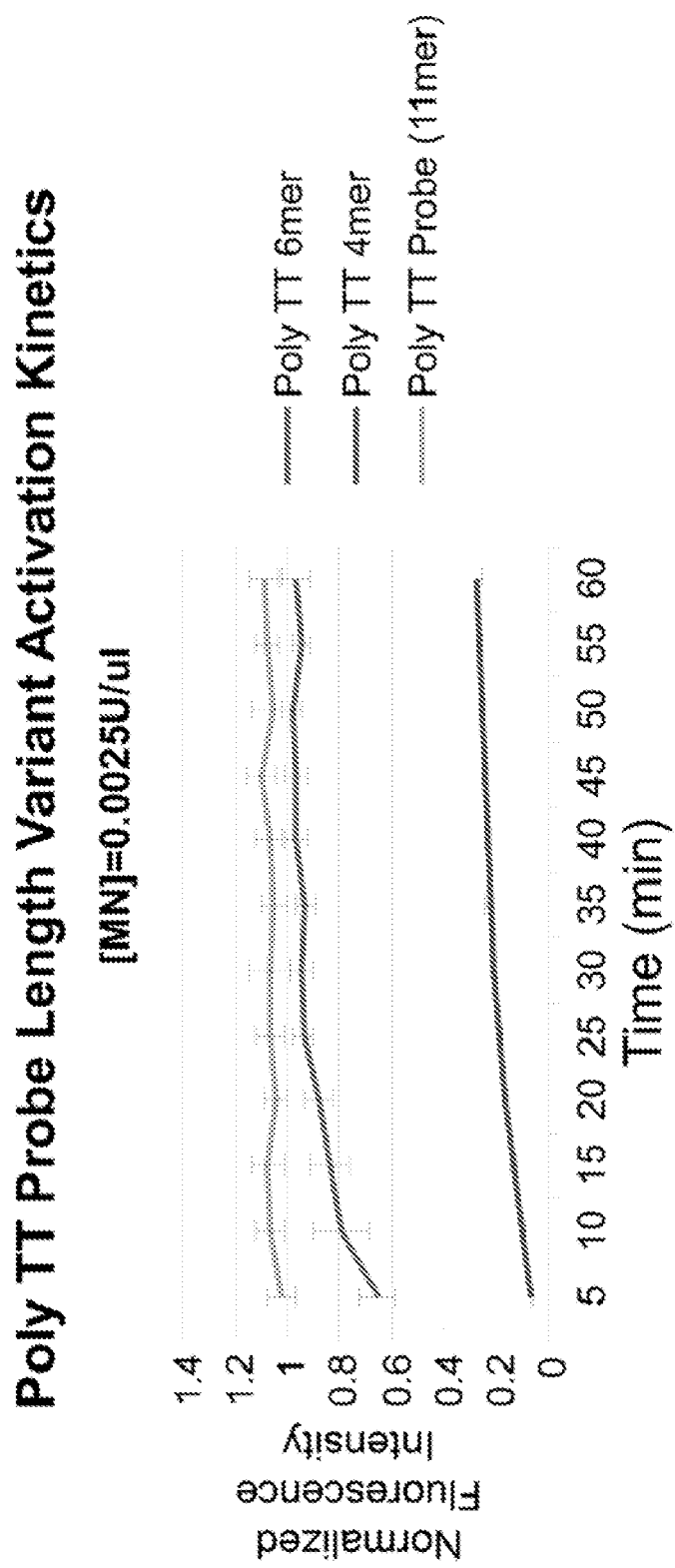
FIG. 33. Comparison of the activation kinetics (digestion with micrococcal nuclease (MN)) of 3 quenched fluorescent oligonucleotide probes of variable length composed of a string of T's. Note: the shorter the probe, the less sensitive it is to MN.

Probes consisting of unmodified deoxythymidines (the Poly TT probes) were highly sensitive to MN (FIG. 33). As the length of these probes was reduced, they exhibited reduced sensitivity to MN, but increased serum stability (FIGS. 32 and 33).

Figure 30:
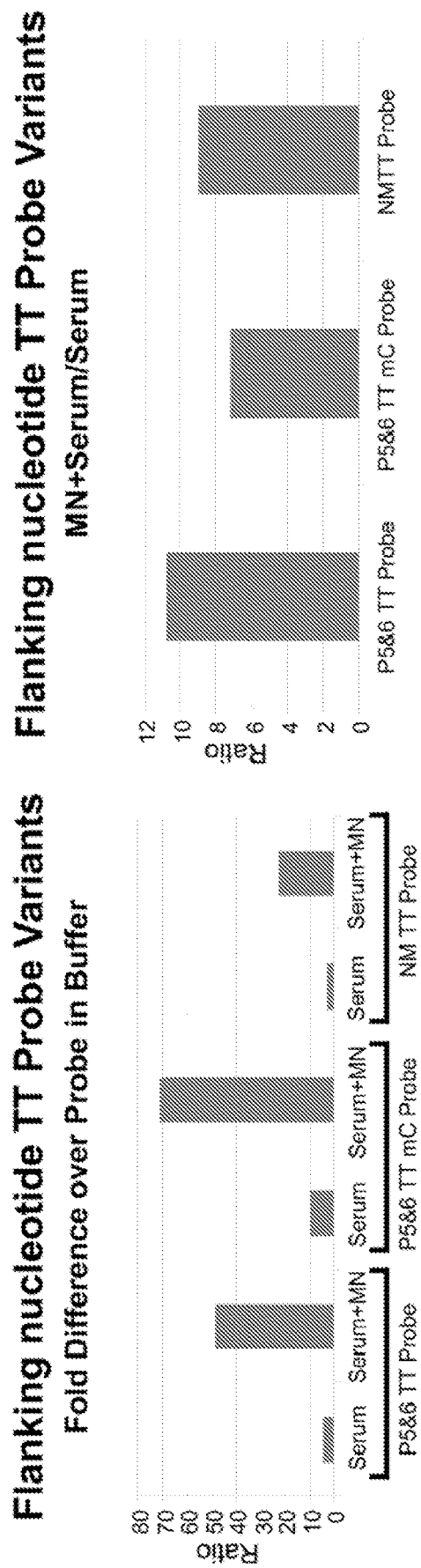
FIG. 30. Serum stability and activation by MN in serum of the NMTT probe and 2 probe variants. All 3 probes are 11 mers with TT in positions 5 & 6. The additional nucleotide positions are different, but all of these additional nucleotides are 2'-O-methyl modified. The ratios between fluorescence of probes digested by MN in serum versus that of probes incubated in serum without MN (right panel) are a measure of signal to background. These results do not show a substantial difference among the probes. This data suggests that the additional, non-T nucleotides do not have an important impact on this measure of probe performance.
Figure 31:
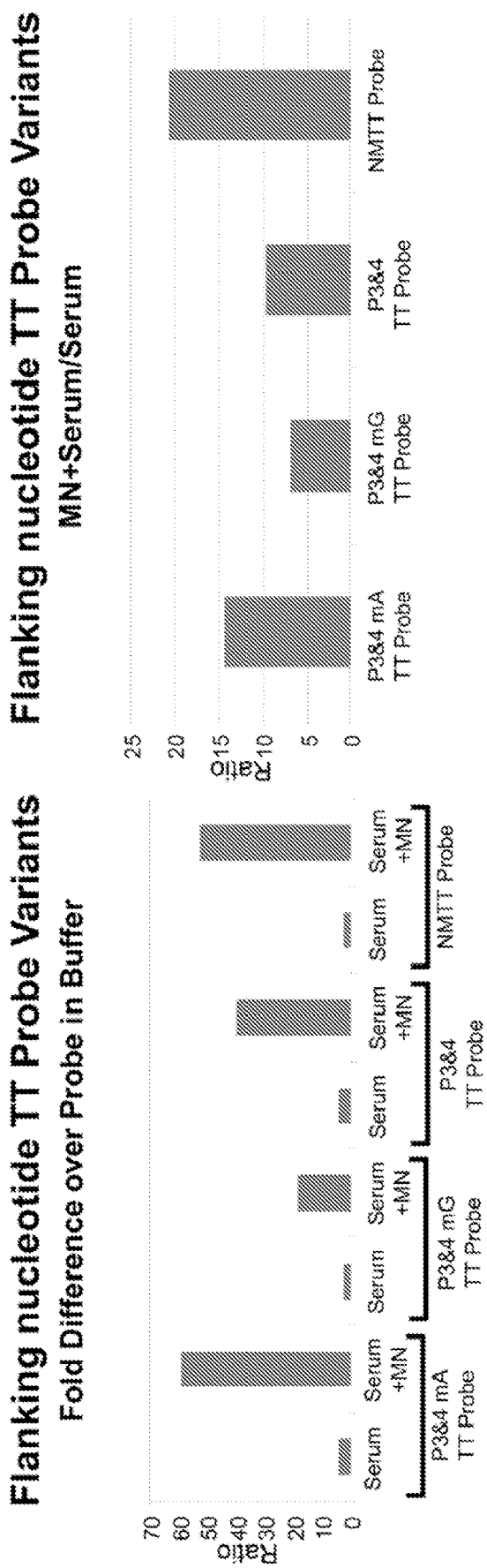
FIG. 31. Serum stability and activation by MN in serum of the NMTT probe (included as a control) and 3 probe variants in which the nucleotides immediately flanking the TT are variable (the remaining nucleotides in all 3 of these probes are 2'-O-methyl U's). Among the 3 probes with variable flanking nucleotides, the ratios of fluorescence of MN-digested versus serum only incubation ranged from ~7 to ~14. These flanking nucleotides could therefore have an impact on this measure of probe performance.

The nucleotides flanking the TT portion of TT probes have only a modest impact on serum stability (FIGS. 30 and 31). MN digestions of probes that include a TT flanked by modified (2'-O-methyl) A, C, G, and U have been studied (FIGS. 30 and 31). Also digestion by MN of probes that consist only of Ts (the "poly TT" probes) has been observed (FIG. 19). The serum stability differences that can be attributed to the flanking nucleotides are modest (FIGS. 30 and 31).

Probes made with the TT Probe (also referred to as the NMTT Probe) oligonucleotide sequence and a variety of near-infrared fluorophores (on the 5'-end) and the QC-1 fluorescence quencher (on the 3'-end) exhibited fluorescence quenching in DPBS, DPBS plus heparin and heparinized mouse blood, that was released (i.e., probe activation was seen) upon incubation with MN (FIGS. 36 and 37).

TABLE 8

| | Sequence: | SEQ ID NO |
|---|---|---|
| FAM Probe List: | | |
| P1&2 TT Probe | FAM- T T mU mU mU mU mU mU mU mU mU -ZEN-RQ | 7 |
| P3&4 TT Probe | FAM- mU mU T T mU mU mU mU mU mU mU -ZEN-RQ | 8 |
| P5&6 TT Probe | FAM- mU mU mU mU T T mU mU mU mU mU -ZEN-RQ | 9 |
| P8&9 TT Probe | FAM- mU mU mU mU mU mU mU T T mU mU -ZEN-RQ | 10 |
| P10&11 TT Probe | FAM- mU mU mU mU mU mU mU mU mU T T -ZEN-RQ | 11 |
| TT Probe 8mer | FAM- mU mU mU T T mU mU mU -ZEN-RQ | 12 |
| TT Probe 6mer | FAM- mU mU T T mU mU -ZEN-RQ | 13 |
| NMTT Probe | FAM- mC mU mC mG T T mC mG mU mU mC -ZEN-RQ | 51 |
| UNA P5&6 TT Probe | FAM- UNA-U UNA-U UNA-U UNA-U T T UNA-U UNA-U UNA-U UNA-U UNA-U -ZEN-RQ | 14 |

TABLE 8-continued

| | Sequence: | SEQ ID NO |
|---|---|---|
| P5&6 TT mC Probe | FAM- mC mC mC mC T T mC mC mC mC mC -ZEN-RQ | 15 |
| P2&3 TT Probe | FAM- mU T T mU mU mU mU mU mU mU mU -ZEN-RQ | 16 |
| P4&5 TT Probe | FAM- mU mU mU T T mU mU mU mU mU mU -ZEN-RQ | 17 |
| P3&4 mG TT Probe | FAM- mU mG T T mG mU mU mU mU mU -ZEN-RQ | 18 |
| P3&4 mA TT Probe | FAM- mU mA T T mA mU mU mU mU mU -ZEN-RQ | 19 |
| P1&2 TT Probe 6mer | FAM- T T mU mU mU mU -ZEN-RQ | 20 |
| P1&2 TT Probe 8mer | FAM- T T mU mU mU mU mU mU -ZEN-RQ | 21 |
| P2&3 TT Probe 6mer | FAM- mU T T mU mU mU -ZEN-RQ | 22 |
| P2&3 TT Probe 8mer | FAM- mU T T mU mU mU mU mU -ZEN-RQ | 23 |
| Poly TT Probe | FAM- T T T T T T T T T T -ZEN-RQ | 24 |
| Poly TT 6mer | FAM- T T T T T T-ZEN-RQ | 25 |
| Poly TT 4mer | FAM-T T T T -ZEN-RQ | 26 |
| NIR Probes: | | |
| IRDye800CW | IRDye800CW- mC mU mC mG TT mC mG mU mU mC -3IRQC1N | 52 |
| Dy780 | Dy780- mC mU mC mG TT mC mG mU mU mC -3IRQC1N | 53 |
| Dy781 | Dy781- mC mU mC mG TT mC mG mU mU mC -3IRQ1CN | 54 |
| DyLight 800 | DyLight 800- mC mU mC mG TT mC mG mU mU mC -3IRQ1CN | 55 |
| Cy7.5 | Cy7.5- mC mU mC mG TT mC mG mU mU mC -3IRQ1CN | 23 |

Abbreviations:
FAM = FAM fluorophore (fluorescein amidite);
IRDye800CW = IRDye 800CW fluorophore of LI-COR Biosciences, Inc.;
Dy780 = Dy780 fluorophore of Dyomics;
Dy781 = Dy781 fluorophore of Dyomics;
DyLight 800 = DyLight 800 fluorophore of Pierce (Thermo Scientific);
Cy7.5 = Cy7.5 fluorophore of Lumiprobe Corporation;
3IRQ1CN = QC-1 quencher of LI-COR Biosciences, Inc.;
ZEN = IDT "ZEN" fluorescence quencher;
RQ = IDT Iowa Black RQ fluorescence quencher;
mA = 2'-O-methyl Adenosine;
mC = 2'-O-methyl-Cytidine;
mG = 2'-O-methyl-Guanosine;
mU = 2'-O-methyl-Uridine;
UNA-U = unlocked nucleic acid Uridine;
UNA- Nucleotides written in bold are deoxy nucleotides (DNA);
InvdT = inverted dT.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of detecting a microbial infection of a sample comprising measuring fluorescence of a sample that has been contacted with a probe for detecting a microbial endonuclease comprising an oligonucleotide of 2-30 nucleotides in length, a fluorophore operably linked to the oligonucleotide, and a quencher operably linked to the oligonucleotide, wherein the oligonucleotide is capable of being cleaved by a microbial nuclease, and has a DNA TT di-nucleotide, DNA AT di-nucleotide, DNA AA di-nucleotide or DNA TA di-nucleotide positioned at nucleotides 1 and 2, 2 and 3, or 3 and 4 as measured from the 5'-end of the oligonucleotide, and wherein the oligonucleotide comprises one or more modified nucleotides, wherein a fluorescence level that is greater than the fluorescence level of an uninfected control indicates that the sample has a microbial infection.

2. The method of claim 1, wherein the at least one fluorophore is selected from the group consisting of the fluorophores Hydroxycoumarin, Alexa fluor, Aminocoumarin, Methoxycoumarin, Cascade Blue, Pacific Blue, Pacific Orange, *Lucifer* yellow, Alexa fluor 430, NBD, R-Phycoerythrin (PE), PE-Cy5 conjugates, PE-Cy7 conjugates, Red 613, PerCP, Cy2, TruRed, FluorX, Fluorescein, FAM, BODIPY-FL, TET, Alexa fluor 532, HEX, TRITC, Cy3, TMR, Alexa fluor 546, Alexa fluor 555, Tamara, X-Rhodamine, Lissamine Rhodamine B, ROX, Alexa fluor 568, Cy3.5 581, Texas Red, Alexa fluor 594, Alexa fluor 633, LC red 640, Allophycocyanin (APC), Alexa fluor 633, APC-Cy7 conjugates, Cy5, Alexa fluor 660, Cy5.5, LC red 705, Alexa fluor 680, Cy7, and IRDye 800 CW.

3. The method of claim 1, wherein the at least one fluorescence quencher is selected from the group consisting of the fluorescence quenchers DDQ-I, Dabcyl, Eclipse, Iowa Black FQ, BHQ-1, QSY-7, BHQ-2, DDQ-II, Iowa Black RQ, QSY-21, BHQ-3, IRDye QC-1, and ZEN.

4. The method of claim 1, wherein the oligonucleotide is 8-15 nucleotides in length and the DNA TT di-nucleotide is positioned at nucleotides 2 and 3.

5. The method of claim 1, wherein the oligonucleotide is 4-6 nucleotides in length and the DNA TT di-nucleotide is positioned at nucleotides 1 and 2.

6. The method of claim 1, wherein the DNA TT di-nucleotide consists of unmodified deoxythymidines.

7. The method of claim 1, wherein the oligonucleotide has between 0-50% purines.

8. The method of claim 1, wherein the oligonucleotide comprises one or more modified pyrimidines, wherein one or more of the pyrimidines other than the DNA TT di-nucleotide, DNA AT di-nucleotide, DNA AA di-nucleotide or DNA TA di-nucleotide are chemically modified.

9. The method of claim 8, wherein one or more of the pyrimidines are 2'-O-methyl modified or are 2'-fluoro modified.

10. The method of claim 1, wherein the oligonucleotide comprises one or more purines, and wherein one or more of the purines are chemically modified.

11. The method of claim 10, wherein one or more of the purines are 2'-O-methyl modified or are 2'-fluoro modified.

12. The method of claim 1, wherein the oligonucleotide is single-stranded.

13. The method of claim 1, wherein the oligonucleotide comprises both RNA and DNA.

14. The method of claim 1, wherein the microbial infection is a *Staphylococcus aureus* or a *Streptococcus pneumoniae* infection.

15. The method of claim 1, wherein the fluorophore is FAM, TET, HEX, JOE, MAX, Cy3, TAMRA, ROX Texas Red, Cy5, Cy5.5, Cy7, Licor IRDye 700, Cy7.5, Dy780, Dy781, DyLight 800, Licor IRDye 800 CW, or Alexa Fluor 647, 660, 680, 750, or 790.

16. The method of claim 1, wherein the quencher is IBFQ, BHQ1, BHQ2, IBRQ, ZEN or Licor IRDye QC-1.

17. A method of detecting a microbial infection of a sample, comprising:

(a) contacting the test sample with a probe for detecting a microbial endonuclease comprising an oligonucleotide of 2-30 nucleotides in length, a fluorophore operably linked to the oligonucleotide, and a quencher operably linked to the oligonucleotide, wherein the oligonucleotide comprises one or more modified nucleotides, is capable of being cleaved by a microbial nuclease, and has a DNA TT di-nucleotide, DNA AT di-nucleotide, DNA AA di-nucleotide or DNA TA di-nucleotide positioned at nucleotides 1 and 2, 2 and 3, or 3 and 4 as measured from the 5'-end of the oligonucleotide to form a digested probe, and (b) measuring the fluorescence emitted by the digested probe.

18. The method of claim 17, wherein the test sample comprises a biological sample and calcium chloride.

19. The method of claim 18, wherein the biological sample is a blood sample.

20. The method of claim 18, wherein the calcium chloride is at a concentration of about 5 to 20 mM.

21. The method of claim 17, wherein the sample has been heated at 55-100° C. for 10 seconds to 20 hours to form a heat-treated test sample prior to testing, and wherein an endonuclease present in the heat-treated test sample has been concentrated prior to testing.

22. The method of claim 21, wherein the concentration is by means of immunoprecipitation.

23. The method of claim 22, wherein the immunoprecipitated endonuclease remains bound to an antibody used in the immunoprecipitation during contact with the probe.

24. The method of claim 22, wherein the immunoprecipitation is by means of anti-micrococcal nuclease antibody-coupled magnetic beads.

25. The method of claim 22, wherein the immunoprecipitation is specific for a particular microbe.

26. The method of claim 17, wherein the endonuclease is a *Staphylococcal aureus* endonuclease and the probe is NMTT FAM-mC mU mC mG T T mC mG mU mU 5 mC-ZEN-RQ.

\* \* \* \* \*